(12) United States Patent
Crowder et al.

(10) Patent No.: US 11,478,642 B2
(45) Date of Patent: *Oct. 25, 2022

(54) SEIZURE ONSET CLASSIFICATION AND STIMULATION PARAMETER SELECTION

(71) Applicant: NeuroPace, Inc., Mountain View, CA (US)

(72) Inventors: Tara Leigh Crowder, Woodside, CA (US); Sharanya Arcot Desai, Sunnyvale, CA (US); Martha Jo Morrell, Portola Valley, CA (US); Thomas Kim Tcheng, Pleasant Hill, CA (US); Ritu Kapur, San Francisco, CA (US)

(73) Assignee: NeuroPace, Inc., Mountain View, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/706,136

(22) Filed: Dec. 6, 2019

(65) Prior Publication Data

US 2020/0108253 A1 Apr. 9, 2020

Related U.S. Application Data

(60) Continuation of application No. 16/152,111, filed on Oct. 4, 2018, now Pat. No. 10,543,368, which is a
(Continued)

(51) Int. Cl.
*A61N 1/36* (2006.01)
*A61B 5/00* (2006.01)
(Continued)

(52) U.S. Cl.
CPC .......... *A61N 1/36064* (2013.01); *A61B 5/374* (2021.01); *A61B 5/4094* (2013.01);
(Continued)

(58) Field of Classification Search
CPC ............ A61N 1/36064; A61N 1/36139; A61N 1/0529; A61N 1/37241; A61N 1/37247;
(Continued)

(56) References Cited

U.S. PATENT DOCUMENTS 6,016,449 A 1/2000 Fischell
6,161,045 A * 12/2000 Fischell ................. A61B 5/378
607/45

(Continued)

FOREIGN PATENT DOCUMENTS

WO 2016154298 A1 9/2016

OTHER PUBLICATIONS

Russakovsky et al., "ImageNet Large Scale Visual Recognition Challenge", International Journal of Computer Vision, available online Apr. 11, 2015, published Dec. 2015; vol. 115, Issue 3, DOI 10.1007/s11263-015-0816-; pp. 211-252.
(Continued)

*Primary Examiner* — Mallika D Fairchild
(74) *Attorney, Agent, or Firm* — Loza & Loza, LLP; David S. Sarisky

(57) ABSTRACT

A neurostimulation system senses electrographic signals from the brain of a patient, extracts features from the electrographic signals, and when the extracted features satisfy certain criteria, detects a neurological event type. A mapping function relates the detected neurological event type to a stimulation parameter subspace and a default stimulation parameter set where the values of the stimulation parameters define an instance of stimulation therapy for the patient. The decision whether to implement a stimulation parameter subspace or a default stimulation parameter set may be informed by integrating other information about a state of the patient. A stimulation parameter subspace or stimulation parameter set may optimized by testing it against
(Continued)

various thresholds until certain effectiveness criteria is satisfied. The neurological event type may be one of several electrographic seizure onset types.

21 Claims, 27 Drawing Sheets

Related U.S. Application Data division of application No. 15/040,932, filed on Feb. 10, 2016, now Pat. No. 10,130,813.

(60) Provisional application No. 62/114,529, filed on Feb. 10, 2015, provisional application No. 62/114,520, filed on Feb. 10, 2015.

(51) Int. Cl.
A61B 5/374 (2021.01)
A61N 1/05 (2006.01)
A61N 1/372 (2006.01)

(52) U.S. Cl.
CPC ........ *A61B 5/4836* (2013.01); *A61N 1/36139* (2013.01); *A61B 5/7264* (2013.01); *A61B 5/7282* (2013.01); *A61N 1/0529* (2013.01); *A61N 1/37241* (2013.01); *A61N 1/37247* (2013.01)

(58) Field of Classification Search
CPC ..... A61B 5/374; A61B 5/4094; A61B 5/4836; A61B 5/7264; A61B 5/7282
See application file for complete search history.

(56) References Cited

U.S. PATENT DOCUMENTS

| | | | |
|---|---|---|---|
| 6,480,743 B1 | 11/2002 | Kirkpatrick et al. | |
| 6,810,285 B2 * | 10/2004 | Pless | A61B 5/7264 600/544 |
| 7,209,787 B2 | 4/2007 | DiLorenzo | |
| 7,231,254 B2 | 6/2007 | DiLorenzo | |
| 7,242,984 B2 | 7/2007 | DiLorenzo | |
| 7,277,758 B2 | 10/2007 | DiLorenzo | |
| 7,280,867 B2 | 10/2007 | Frei | |
| 7,324,851 B1 | 1/2008 | DiLorenzo | |
| 7,403,820 B2 | 7/2008 | DiLorenzo | |
| 7,529,582 B1 | 5/2009 | DiLorenzo | |
| 7,542,803 B2 | 6/2009 | Heruth | |
| 7,599,736 B2 | 10/2009 | DiLorenzo | |
| 7,623,928 B2 | 11/2009 | DiLorenzo | |
| 7,676,273 B2 | 3/2010 | Goetz | |
| 7,747,325 B2 | 6/2010 | DiLorenzo | |
| 7,822,481 B2 | 10/2010 | Gerber | |
| 7,853,322 B2 | 12/2010 | Bourget | |
| 7,853,329 B2 | 12/2010 | DiLorenzo | |
| 7,894,903 B2 | 2/2011 | John | |
| 7,899,545 B2 | 3/2011 | John | |
| 7,930,035 B2 | 4/2011 | DiLorenzo | |
| 7,957,797 B2 | 6/2011 | Bourget | |
| 7,957,809 B2 | 6/2011 | Bourget | |
| 7,966,073 B2 | 6/2011 | Pless | |
| 7,974,696 B1 | 7/2011 | DiLorenzo | |
| 8,027,730 B2 | 9/2011 | John | |
| 8,126,567 B2 | 2/2012 | Gerber | |
| 8,543,214 B2 | 9/2013 | Osorio | |
| 8,543,217 B2 | 9/2013 | Stone | |
| 8,694,115 B2 | 4/2014 | Goetz | |
| 8,706,237 B2 | 4/2014 | Giftakis et al. | |
| 8,731,656 B2 | 5/2014 | Bourget | |
| 8,903,486 B2 | 12/2014 | Bourget | |
| 10,123,717 B2 | 11/2018 | Tcheng | |
| 2003/0018367 A1 | 1/2003 | DiLorenzo | |
| 2003/0171789 A1 | 9/2003 | Malek | |
| 2004/0199217 A1 | 10/2004 | Lee | |
| 2004/0199218 A1 | 10/2004 | Lee | |
| 2004/0215286 A1 | 10/2004 | Stypulkowski | |
| 2004/0267330 A1 | 12/2004 | Lee | |
| 2005/0021103 A1 | 1/2005 | DiLorenzo | |
| 2005/0021104 A1 | 1/2005 | DiLorenzo | |
| 2005/0060007 A1 | 3/2005 | Goetz | |
| 2005/0060008 A1 | 3/2005 | Goetz | |
| 2006/0265022 A1 * | 11/2006 | John | A61N 1/3614 607/45 |
| 2007/0073355 A1 | 3/2007 | DiLorenzo | |
| 2007/0142862 A1 | 6/2007 | DiLorenzo | |
| 2007/0142874 A1 | 6/2007 | John | |
| 2007/0162086 A1 | 7/2007 | DiLorenzo | |
| 2007/0167991 A1 | 7/2007 | DiLorenzo | |
| 2007/0208212 A1 | 9/2007 | DiLorenzo | |
| 2007/0287931 A1 | 12/2007 | DiLorenzo | |
| 2008/0058773 A1 | 3/2008 | John | |
| 2008/0061961 A1 * | 3/2008 | John | A61B 5/4809 340/539.12 |
| 2008/0071314 A1 | 3/2008 | John | |
| 2008/0109005 A1 | 5/2008 | Trudeau | |
| 2008/0119900 A1 | 5/2008 | DiLorenzo | |
| 2009/0018609 A1 | 1/2009 | DiLorenzo | |
| 2010/0023089 A1 | 1/2010 | DiLorenzo | |
| 2010/0217348 A1 | 8/2010 | DiLorenzo | |
| 2010/0241183 A1 | 9/2010 | DiLorenzo | |
| 2010/0249859 A1 | 9/2010 | DiLorenzo | |
| 2011/0040353 A1 * | 2/2011 | Gerber | A61N 1/36146 607/59 |
| 2011/0307030 A1 | 12/2011 | John | |

OTHER PUBLICATIONS

Lecun et al., "Deep Learning", Nature, May 27, 2015, vol. 521; DOI:10.1038/nature14539; pp. 436-444.

Xu et al., "Survey of Clustering Algorithms", IEEE Transactions on Neural Networks, vol. 16, No. 3, May 1, 2005; 35 pages.

Krizhevsky et al., "ImageNet Classification with Deep Convolutional Neural Networks", NIPS'12 Proceedings of the 25th International Conference on Neural Information Processing Systems—vol. 1, pp. 1097-1105, Dec. 3, 2012.

Ling, Zhen-Huia et al. "Waveform Modeling and Generation Using Hierarchical Recurrent Neural Networks for Speech Bandwidth Extension", IEEE/ACM Transactions on Audio, Speech, and Language Processing, vol. 26, No. 5, pp. 883-894, May 2018.

Zeiler, Matthew D. et al. "Visualizing and Understanding Convolutional Networks", ArXiv:1311.2901v3, Nov. 28, 2013, pp. 1-11.

Ali Hossam Shoeb, and John GuttaAg: "Application of Machine Learning to Epileptic Seizure Detection", Appearing in the Proceedings of the 27th International Conference on Machine Learning, Haifa, Israel 2010, Copyright 2010.

Spencer, S. S., Guimaraes, P., Katz, A., Kim, J., and Spencer, D.: "Morphological patterns of seizures recorded intracranially," Epilepsia, 33:537-545 (1992).

Lee, S. A., Spencer, D. D., and Spencer, S. S.: "Intracranial EEG seizure-onset patterns in neocortical epilepsy," Epilepsia, 41:297-307 (2000).

Langan, Y., Nashef, L., and Sander, J. W.: "Case-control study of SUDEP," Neurology, 64:1131-1133 (2005).

Bateman, L. M., Li, C. S., Lin, T. C., and Seyal, M.: "Serotonin reuptake inhibitors are associated with reduced severity of ictal hypoxemia in medically refractory partial epilepsy," Epilepsia, 51:2211-2214 (2010).

Schiller, Y., Cascino, G. D., Busacker, N. E., and Sharbrough, F. W.: "Characterization and comparison of local onset and remote propagated electrographic seizures recorded with intracranial electrodes," Epilepsia,39:380-388 (1998).

Perucca, P., Dubeau, F., and Gotman, J.: "Intracranial electroencephalographic seizure-onset patterns: effect of underlying pathology," Brain Journal of Neurology, 137:183-196 (2014).

Tass, P. A., Qin, L., Hauptmann, C., Dovero, S., Bezard, E., Boraud, T., and Meissner, W. G.: "Coordinated reset has sustained aftereffects in Parkinsonian monkeys," Ann. Neurol, 72:816-820 (2012).

(56) References Cited

OTHER PUBLICATIONS

Lysyansky, B., Popovych, O. V., and Tass, P. A.: "Optimal number of stimulation contacts for coordinated reset neuromodulation," Front Neuroeng.,6:5 (2013).
Colom, L. V.: "Septal networks: relevance to theta rhythm, epilepsy and Alzheimer's disease," J Neurochem., 96:609-623 (2006).
Miller, J. W., Turner, G. M., and Gray, B. C.: "Anticonvulsant effects of the experimental induction of hippocampal theta activity," Epilepsy Res., 18:195-204 (1994).
Crespel, A., Coubes, P., and Baldy-Moulinier, M.: "Sleep influence on seizures and epilepsy effects on sleep in partial frontal and temporal lobe epilepsies," M. Clin.Neurophysiol.,111 Suppl 2:S54-S59 (2000).
Herman, S. T., Walczak, T. S., and Bazil, C. W.: "Distribution of partial seizures during the sleep-wake cycle: differences by seizure onset site," Neurology,56:1453-1459 (2001).
Minecan, D., Natarajan, A., Marzec, M., and Malow, B.: "Relationship of epileptic seizures to sleep stage and sleep depth," Sleep,25:899-904 (2002).
Malow, B. A.: "The interaction between sleep and epilepsy," Epilepsia, 48 Suppl 9:36-38 (2007).
Ng, M. and Pavlova: "Why are seizures rare in rapid eye movement sleep? Review of the frequency of seizures in different sleep stages," M. Epilepsy Res.Treat.,2013:932790 (2013).
Welsh, D. K., Richardson, G. S., and Dement, W. C.: "A circadian rhythm of hippocampal theta activity in the mouse," Physiol.Behav, 35:533-538 (1985).
Cantero, J. L., Atienza, M., Stickgold, R., Kahana, M. J., Madsen, J. R., and Kocsis, B.: "Sleep-dependent theta oscillations in the human hippocampus and neocortex,", J Neurosci, 23:10897-10903 (2003).
Soodman, J. H., Berger, R. E., and Tcheng, T. K.: "Preemptive low-frequency stimulation decreases the incidence of amygdala-kindled seizures," Epilepsia, 46:1-7 (2005).
Carrington, C. A., Gilby, K. L., and Mcintyre, D. C.: "Effect of focal low-frequency stimulation on amygdala-kindled afterdischarge thresholds and seizure profiles in fast- and slow-kindling rat strains," Epilepsia, 48:1604-1613 (2007).
Chan, A. M., Sun, F. T., Boto, E. H., and Wingeier, B. M.: "Automated seizure onset detection for accurate onset time determination in intracranial EEG," Clin.Neurophysiol., 119:2687-2696 (2008).
Brinkmann, B. H., Patterson, E. E., Vite, C., Vasoli, V. M., Crepeau, D., Stead, M., Howbert, J. J., Cherkassky, V., Wagenaar, J. B., Litt, B., and Worrell, G. A.: "Forecasting Seizures Using Intracranial EEG Measures and SVM in Naturally Occurring Canine Epilepsy," G. A. PLoS.One.,10:e0133900 (2015).
Van Putten, M. J., Kind, T., Visser, F., and Lagerburg, V.: "Detecting temporal lobe seizures from scalp EEG recordings: a comparison of various features," Clin.Neurophysiol.,116:2480-2489 (2005).
Wackermann, J.: "Beyond mapping: estimating complexity of multichannel EEG recordings," Acta Neurobiol.Exp. (Wars.), 56:197-208 (1996).
Ogren, Jennifer A., Bragin, Anatol, Wilson, Charles L., Hoftman, Gil D., Lin, Jack J., Dutton, Rebecca A., Fields, Tony A., Toga, Arthur W., Thompson, Paul M., Engel, Jr., Jerome, Staba, Richard J.: "Three-dimensional hippocampal atrophy maps distinguish two common temporal lobe seizure-onset patterns," Epilepsia, 50(6):1361-1370 (2009).

Ivan Osorio, Mark G. Frei and Steven B. Wilkinson: "Real-Time Automated Detection and Quantitative Analysis of Seizures and Short-Term Prediction of Clinical Onset", Epilepsia, 39(6):615-627 (1998).
Lojini Logesparan, Alexander J. Casson and Esther Rodrigufz-Villegas: "Optimal features for online seizure detection", Medical & Biological Engineering & Computing, 50.7 (2012): 659-669, and Supplementary Material relating to article.
Ali Hossam Shoeb: Thesis "Application of Machine Learning to Epileptic Seizure Onset Detection and Treatment", Submitted to Harvard-MIT Div. of Health Sciences re Dr. of Philosophy in EE and Med Engineering at MIT, Sep. 2009.
Maryann D'Alessandro, George Vachtsevanos, Rosana Esteller, Javier Echauz, Stephen Cranstoun, Greg Worrell, Landi Parish and Brian Litt: "A multi-feature and multi-channel univariate selection process for seizure prediction", Clinical Neurophysiology 116 (2005) 506-516.
Isa Conradsen, Student Member; IEEE, Sándor Beniczky, Karsten Hoppe, Peter Wolf and Helge B. D. Sorensen Member, IEEE: "Automated algorithm for generalised tonic-clonic epileptic seizure onset detection based on sEMG zero-crossing rate", IEEE Transactions on Biomedical Engineering, Copyright IEEE 2011, pubs-permissions@ieee.org.
Brian Litt, Rosana Esteiler, Javier Echauz, Maryann D'Alessandro, Rachel Shor, Thomas Henry, Page Pennell, Charles Epstein, Roy Bakay, Marc Dichter, and George Vachtsevanos: "Epileptic Seizures May Begin Hours in Advance of Clinical Onset: A Report of Five Patients", Neuron, vol. 30, 51-64, Apr. 2001.
Alaa Kharbouch, Ali Shoeb, John Guttag, and Sydney S. Cash: "An algorithm for seizure onset detection using intracranial EEG," Epilepsy Balmy. Dec. 2011; 22(01): S29-S35.
Yusuf U Khan, Omar Farooq and Priyanka Sharma: "Automatic Detection of Seizure Onset in Pediatric EEG", International Journal of Embedded Systems and Applications (IJESA) vol. 2, No. 3, Sep. 2012.
Yizhuo Zhang, Guanghua Xu, Jing Wang, Lin Liang: "An automatic patient-specific seizure onset detection method in intracranial EEG based on incremental nonlinear dimensionality reduction", Computers in Biology and Medicine 40 (2010) 889-899.
P. A. Tass, A. N. Silchenko, C. Hauptmann, U. B. Barnikol, and E.-J Speckmann: "Long-lasting desynchronization in rat hippocampal slice induced by coordinated reset stimulation", Physical Review F 80, 011902 (2009).
Oleksandr V. Popovych and Peter A. Tass: "Desynchronizing Electrical and Sensory Coordinated Reset Neuromodulation", Frontiers in Human Neuroscience, Mar. 20, 2012, vol. 6, Article 58.
Antonio García-Hernández, Brian H. Bland, Julio Facelli, and C. Luis V. Colom: "Septo-hippocampal networks in chronic epilepsy", EAT Neurol. Mar. 2010; 222(1): 86-92.
A.J. Gabor, R.R. Leach, and F.U. Dowla: "Automated Seizure Detection Using a Self-Organizing Neural Network", Dept. of Neurology, University of CA, Davis Medical Center, Jan. 5, 1996; Published Apr. 15, 1996, Electroencephalography and Clinical Neurophysiology 99 (1996) 257-266.
A.J. Gabor: "Automated Seizure Detection Using a Self-Organizing Neural Network, Validation and Comparison with Other Detection Strategies", Dept. of Neurology, University of CA, Davis Medical Center, Accepted for Publication Feb. 28, 1998, Electroencephalography and Clinical Neurophysiology 107 (1998) 27-32.

* cited by examiner

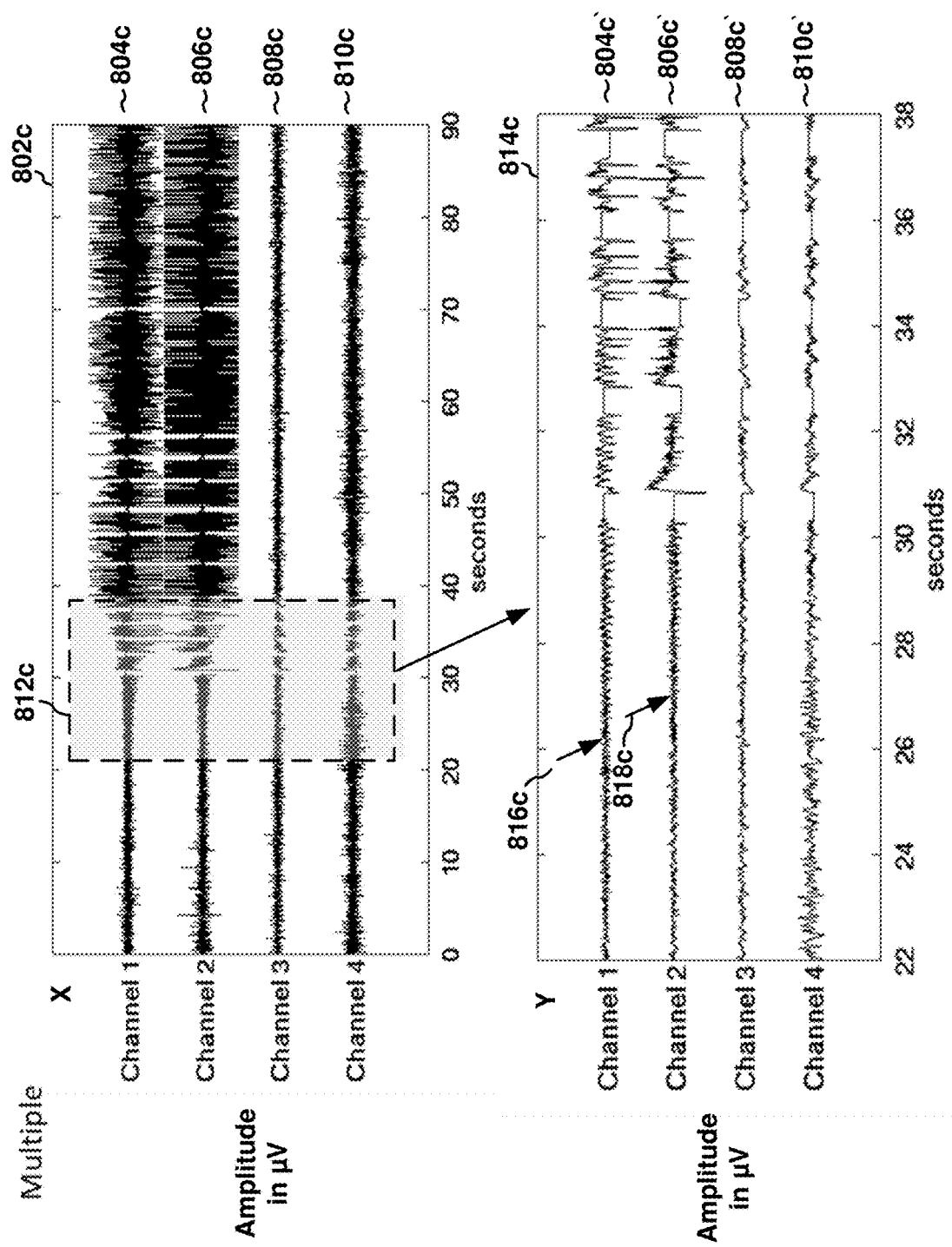

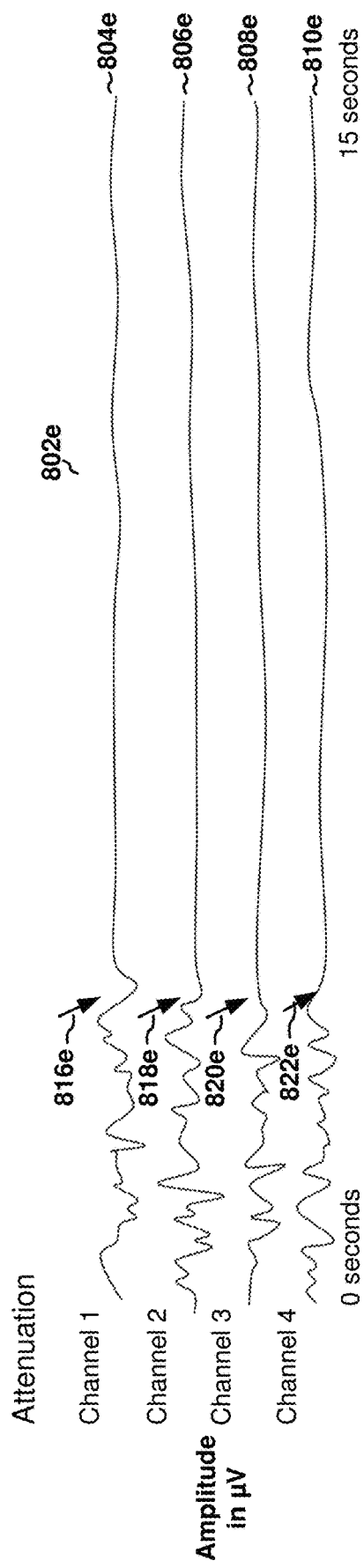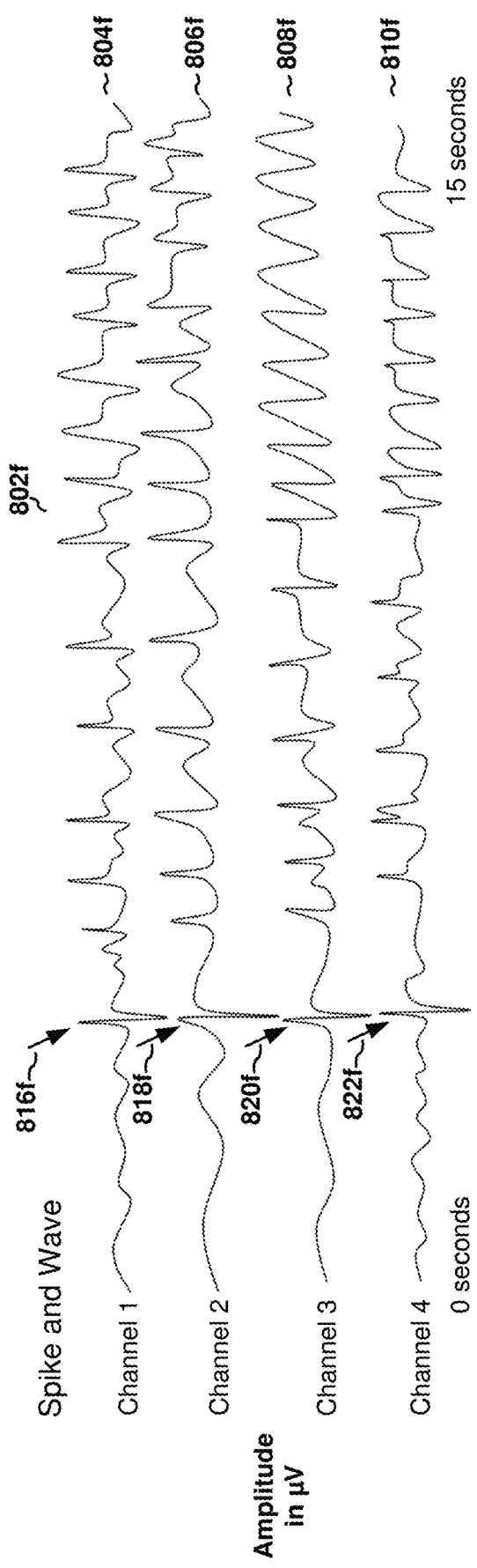

different occurrences of an onset, on the same channel (CH1), for the same patient

1202 (step 720) ECoG1 CH1

| probability | Onset type |
|---|---|
| 0.8 | Hypersynchronous |
| 0.1 | Low voltage fast |
| 0.05 | High voltage beta |
| 0.05 | Multiple |

1204 (step 720) ECoG2 CH1

| probability | Onset type |
|---|---|
| 0.85 | Hypersynchronous |
| 0.1 | Low voltage fast |
| 0.05 | High voltage beta |
| 0.00 | Multiple |

1206 (step 720) ECoG3 CH1

| probability | Onset type |
|---|---|
| 0.85 | Hypersynchronous |
| 0.05 | Low voltage fast |
| 0.05 | High voltage beta |
| 0.05 | Multiple |

1208 (step 720) ECoG4 CH1

| probability | Onset type |
|---|---|
| 0.85 | Hypersynchronous |
| 0.05 | Low voltage fast |
| 0.05 | High voltage beta |
| 0.05 | Multiple |

1210 (step 722)

| probability | Onset type |
|---|---|
| 0.85 | Hypersynchronous |
| 0.075 | Low voltage fast |
| 0.0375 | High voltage beta |
| 0.0375 | Multiple |

1212 (step 724)
⇒ Dominant onset type on channel 1: Hypersynchronous

1214 (step 726)

| Effective stim parameters in patient X, channel Y (Amp, Freq, Pulse Width, Burst Duration) | Sz reduction % |
|---|---|
| 1 mA, 7 Hz, 200 μs, 2 seconds | 100 |
| 0.8 mA, 6 Hz, 200 μs, 2.5 seconds | 90 |
| 1 mA, 10 Hz, 150 μs, 3 seconds | 80 |
| 1.5 mA, 7 Hz, 150 μs, 3 seconds | 75 |

Dominant onset type in patient X, channel 1: Hypersynchronous

FIG. 12

Onset type: Hypersynchronous

1302 (step 726) Patient 1 Channel 1

| Effective stim parameters | Sz reduction% |
|---|---|
| 1 mA, 7 Hz, 200 µs | 100 |
| 0.8 mA, 6 Hz, 200 µs | 90 |
| 1 mA, 10 Hz, 150 µs | 80 |
| 1.5 mA, 7 Hz, 150 µs | 75 |

1302a, 1302b, 1302c, 1302d

1304 (step 726) Patient 2 Channel 2

| Effective stim parameters | Sz reduction% |
|---|---|
| 1.2 mA, 7 Hz, 170 µs | 100 |
| 0.9 mA, 10 Hz, 200 µs | 95 |
| 1.1 mA, 9 Hz, 150 µs | 85 |
| 1.2 mA, 8 Hz, 160 µs | 80 |

1304a, 1304b, 1304c, 1304d

1306 (step 726) Patient 3 Channel 1

| Effective stim parameters | Sz reduction% |
|---|---|
| 1.5 mA, 10 Hz, 180 µs | 100 |
| 0.95 mA, 9 Hz, 200 µs | 90 |
| 1.2 mA, 7 Hz, 200 µs | 85 |
| 1.1 mA, 10 Hz, 200 µs | 80 |

1306a, 1306b, 1306c, 1306d

1308 (step 728) Clustering algorithm

| Default | Amp, Freq, PulseWidth, BurstDuration |
|---|---|
| | 1.2 mA, 7 Hz, 200 µs, 3 seconds |
| Effective stimulation subspace(s) | 0.8 – 1.5 mA, 6-10 Hz, 150 – 200 µs, 2-3.5 seconds |

1310, 1312

Onset type: Hypersynchronous

1314 Onset type: Low Voltage Fast

| Default | 3 mA, 100 Hz, 500 µs, 400 ms |
|---|---|
| Effective stimulation subspace(s) | 2.5 – 4 mA, 80-120 Hz, 450-600 µs, 250-500 ms |

1316 Onset type: High Voltage Beta

| Default | 0.8 mA, 200 Hz, 180 µs, 200 ms |
|---|---|
| Effective stimulation subspace(s) | 0.5-1 mA, 180-250 Hz, 70-110 µs, 80-250 ms |

FIG. 13

SEIZURE ONSET CLASSIFICATION AND STIMULATION PARAMETER SELECTION

CROSS-REFERENCE TO RELATED APPLICATIONS

This application is a continuation application of U.S. patent application Ser. No. 16/152,111, filed Oct. 4, 2018, now U.S. Pat. No. 10,543,368, for "Seizure Onset Classification and Stimulation Parameter Selection," which is a divisional application of U.S. patent application Ser. No. 15/040,932, filed Feb. 10, 2016, now U.S. Pat. No. 10,130,813, for "Seizure Onset Classification and Stimulation Parameter Selection," which claims the benefit of U.S. Provisional Application Ser. No. 62/114,529, entitled "Seizure Onset Classification and Stimulation Parameter Selection," and U.S. Provisional Application Ser. No. 62/114,520, entitled "Seizure Onset Classification and Stimulation Parameter Mapping and Selection," both filed Feb. 10, 2015, all of which are incorporated herein by reference in their entirety.

BACKGROUND

Technical Field

The present disclosure relates to systems, devices and methods for treating neurological disorders, e.g., epilepsy, with closed-loop (responsive) neurostimulation. More particularly, the disclosed embodiments relate to systems, devices and methods for defining the stimulation to be delivered based at least in part on one or more of a type of neurological event detected, a state of a patient measured from physiological data elements; and comparison to the clinical effectiveness of a prior course of stimulation therapy, such that the therapeutic benefit of the stimulation therapy can be optimized for the patient.

Background

Neurostimulation therapy, increasingly that which is delivered by an implanted pulse generator or neurostimulator, is being used for various chronic diseases and neurological disorders, such as epilepsy, pain management, and movement disorders such as Parkinson's disease. An objective of the stimulation is to modulate the patient's neural tissue in some desired way to either treat the disease or disorder itself or to change a symptom of the disease or disorder. For example, for epilepsy, an objective may be to reduce the number of seizures the patient experiences, and for a movement disorder, an objective may be to reduce tremor. Depending on the objective, the stimulation may be intended to increase neural activity or inhibit it. Metrics relative to the objective of the therapy can be used to measure the effectiveness of the therapy.

In an implantable neurostimulator, stimulation therapy typically involves generating a train of pulses of electrical stimulation (current-controlled or voltage-controlled) and applying them in a "burst" to neural tissue of the patient through electrodes. The pulses are usually "charge balanced" for safety, to minimize an undesirable build-up of charge at the electrode-to-tissue interface. The therapy is characterized by parameters, the values of which define what each instance of therapy will comprise. For example, the parameters may include the magnitude of the pulse, or pulse amplitude, the width of the pulse, and the time between bursts of pulses. The neurostimulator will allow each of these parameters to have a value in a range of values. Collectively, parameters and the range of possible values for each may be referred to as the "parameter space" for the stimulation the neurostimulator is configurable to deliver. When a value is specified for each parameter in the parameter space, this is referred to herein as a "stimulation parameter set."

Implantable neurostimulators are known that not only generate stimulation according to stimulation parameter sets and then deliver it through electrodes, but also sense and monitor electrographic signals from the patient. These neurostimulators can be configured to look for certain patterns in the sensed signals and, if one of those patterns is detected, use the fact of detection as a trigger to generate and deliver the stimulation. NeuroPace, Inc. (Mountain View, Calif.) manufactures and sells one such neurostimulator under the trade name "RNS" for treating epilepsy. The neurostimulator subjects the sensed signals to one or more tools or processes which extract features and analyze the extracted features, alone or in combination, to determine when one of the patterns should be deemed to have been detected as a neurological event. Each pattern can be classified as a different neurological event type. The neurostimulator can be configured to deliver stimulation according to a particular stimulation parameter set whenever a neurological event is detected.

In epilepsy, it is generally desirable to treat a seizure at or near the time it begins electrographically, or at or during its onset. Accordingly, it is desirable to configure a neurostimulator to detect neurological events that comprise a type of seizure onset for the patient. When stimulation therapy is applied to neural tissue that is evidencing a type of electrographic seizure onset, the stimulation may interrupt the developing seizure and either arrest it altogether or reduce its severity, improving the overall condition of the patient. Thus, the overall condition of the patient also can be used as a measure of the clinical effectiveness of a stimulation therapy delivered by an implantable neurostimulator. Similarly, a metric that can be used as a measure of the clinical effectiveness of the therapy may be the percent reduction in the number of frequency of seizures experienced by the patient. These seizures may counted based on reports of seizures by the patient or the patient's caregiver (e.g., a seizure 'diary' for the patient), or they may be counted using some proxy for a seizure, such as the length of time electrographic activity measured from a patient and corresponding to a seizure persists.

When the parameter space for the stimulation is relatively large, then choosing values for each stimulation parameter to create a parameter set can be challenging. Even when there is a reliable way of detecting the neurological event type to be used to trigger delivery of stimulation, determining which stimulation parameter is optimal for that event type has been an empirical process, involving a lot of trial and error.

Finding a parameter set that optimizes the clinical effectiveness of a stimulation therapy for a patient can be challenging. Sometimes a patient has to visit the physician many times to try new parameter sets before identifying one that is effective (e.g. reduces the frequency of reported seizures by ≥50%). Unless the patient happens to experience one of the neurological events the neurostimulator is configured to detect when the patient is in the doctor's office, then the process involves adjusting the parameter set, sending the patient home to see how he does for a while, then bringing him back in. If the patient has not been doing well, further adjustments will be made—that is, a new stimulation parameter set will be tried—and so on and so forth until a parameter set is arrived at that seems to work well (be clinically effective). The time between visits is usually at least a few weeks or longer. Thus this empirical process is not ideal and, for some patients, it may take a long period of trying many different stimulation parameter sets before arriving at one that works well. Moreover, since it is practically impossible to try out every available stimulation parameter subspace and stimulation parameter sets within a subspace, an optimal subspace or set for a patient may never be discovered. Thus, being able to automatically identify an optimal stimulation subspace or stimulation parameter set for a patient would be a significant improvement over the currently available responsive neurostimulation systems.

SUMMARY

Disclosed herein are systems, devices, and methods relating to a neurostimulation system with implantable and external components configured to sense electrographic activity from a patient, analyze the electrographic activity by extracting features from it, and detect neurological events in the electrographic activity. Each detected neurological event may be categorized as a neurological event type. Each neurological event type may be mapped to a collection of stimulation parameters, each with a range of values, from which a stimulation parameter set can be derived. (This collection of parameters and ranges of parameter values is referred to herein as a "stimulation parameter subspace" since it represents a subset of the maximum possible ranges or each of the parameters in the collection, i.e., a subset of the entire "stimulation parameter space"). An implanted neurostimulator component of the neurostimulation system can create and then deliver, through stimulation elements (e.g., electrodes) an instance of stimulation therapy to a patient in accordance with the stimulation parameter set. Each neurological event type also may be mapped to a default stimulation parameter set by the mapping function.

The mapping function may be created using data obtained about the therapeutic effect of stimulation parameter sets when delivered in response to the detection of the same type of neurological event, either in the particular patient or across a particular patient population (e.g., as may be collected in a clinical investigation). The neurological event type of interest may be the onset of an electrographic seizure (seizure onset), for example, human-defined types of seizure onset, or seizure onset types determined by a machine, such as by a clustering process.

In some embodiments, the neurostimulation system may integrate information other than the information proposed or recommended by the mapping function in deciding whether to use a stimulation parameter subspace from which to derive a stimulation parameter set to apply an instance of stimulation therapy or whether to use a default stimulation parameter set. Such integrated information may include, for example, the present stimulation parameter set with which the neurostimulator is delivering instances of stimulation therapy, the history of stimulation parameter sets used with the patient, the time since the stimulation parameter set was changed last (e.g., has the present stimulation parameter set had time to work); and various metrics relating to how well the patient is doing (e.g., pH, tissue oxygenation, neurotransmitter levels, number of reported clinical seizures (e.g., based on the patient's seizure diary), the rate at which neurological events are being detected, the occurrence (or lack thereof) of various proxies for electrographic seizures (e.g., "long episodes" and "saturations", the power change in various frequency bands, and evoked potential amplitude). If the patient is doing well based on one or more of these other data elements, then even when the mapping function proposes or recommends a change to a stimulation parameter subspace or to a particular stimulation parameter set (e.g., a default stimulation parameter set), the neurostimulation system may determine not to make the change.

In other embodiments, the neurostimulation system may test a stimulation parameter set against criteria designed to provide information about the clinical effectiveness of the stimulation parameter set, and if the criteria suggests the stimulation therapy is less than optimal, adjust one or more values of the stimulation parameter set until effectiveness is improved. In some embodiments, if no stimulation parameter sets derived from a particular stimulation parameter subspace yield effective results for the patient, the neurostimulation system may propose using a different stimulation parameter subspace from which to derive stimulation parameter sets.

Embodiments of the neurostimulation system may comprise configurations in which (1) all of the functions or elements described above are carried out in implantable components, with inputs originating internally, externally of the patient, or both; and (2) some of the functions or elements described above are carried out in implantable components, with input internally, externally of the patient, or both and some are carried out in external components.

BRIEF DESCRIPTION OF THE DRAWINGS

Aspects, features, benefits and advantages of the embodiments described herein will be apparent with regard to the following description, appended claims and accompanying drawings where:

FIG. 8C is an illustration of a waveform set corresponding to a multiple seizure onset.

FIG. 8E is an illustration of a waveform set corresponding to an attenuation seizure onset.

FIG. 8F is an illustration of a waveform set corresponding to a spike and waveform seizure onset.

FIGS. 10, 11, 12 and 13 are illustrations of an example process flow associated with the method of FIG. 7A and FIG. 7B.

DETAILED DESCRIPTION

Embodiments disclosed herein relate to systems, devices and methods for treating neurological diseases and disorders, e.g., epilepsy, with an implantable neurostimulator configured to apply an electrical stimulation therapy to the neural tissue of a patient. The stimulation is applied according to the values of various parameters which collectively define the therapy, such as how strong it will be, how much of it will be delivered per instance of therapy and how much time will elapse between instances of therapy. A patient's electrographic activity is analyzed to identify one or more neurological event types, and then, based on the neurological event type(s), embodiments automatically select a range of possible values for each stimulation parameter as well as a discrete value within each range for each parameter. A stimulation parameter set to define the therapy for future instances of stimulation can be derived automatically or based in part on input from a clinician treating the patient, based on the selected range of possible values or discrete values. Other embodiments provide information in addition to the range of possible values and the discrete values that can be integrated into the decision whether to use a particular stimulation parameter set with a particular patient. This information may include physiological information about a state of the patient, or other information that is understood to be related to a state of the patient, as will be explained in more detail below.

Still other embodiments are configured to use measures of clinical effectiveness of a stimulation therapy to optimize the values in a stimulation parameter set to achieve the best result for the patient. Embodiments are described primarily with reference to epilepsy as the neurological disorder of interest, different types of onsets of an epileptic seizure as the neurological event types of interest, and patient states and measures of clinical effectiveness that are related to epilepsy.

Figure 1A:
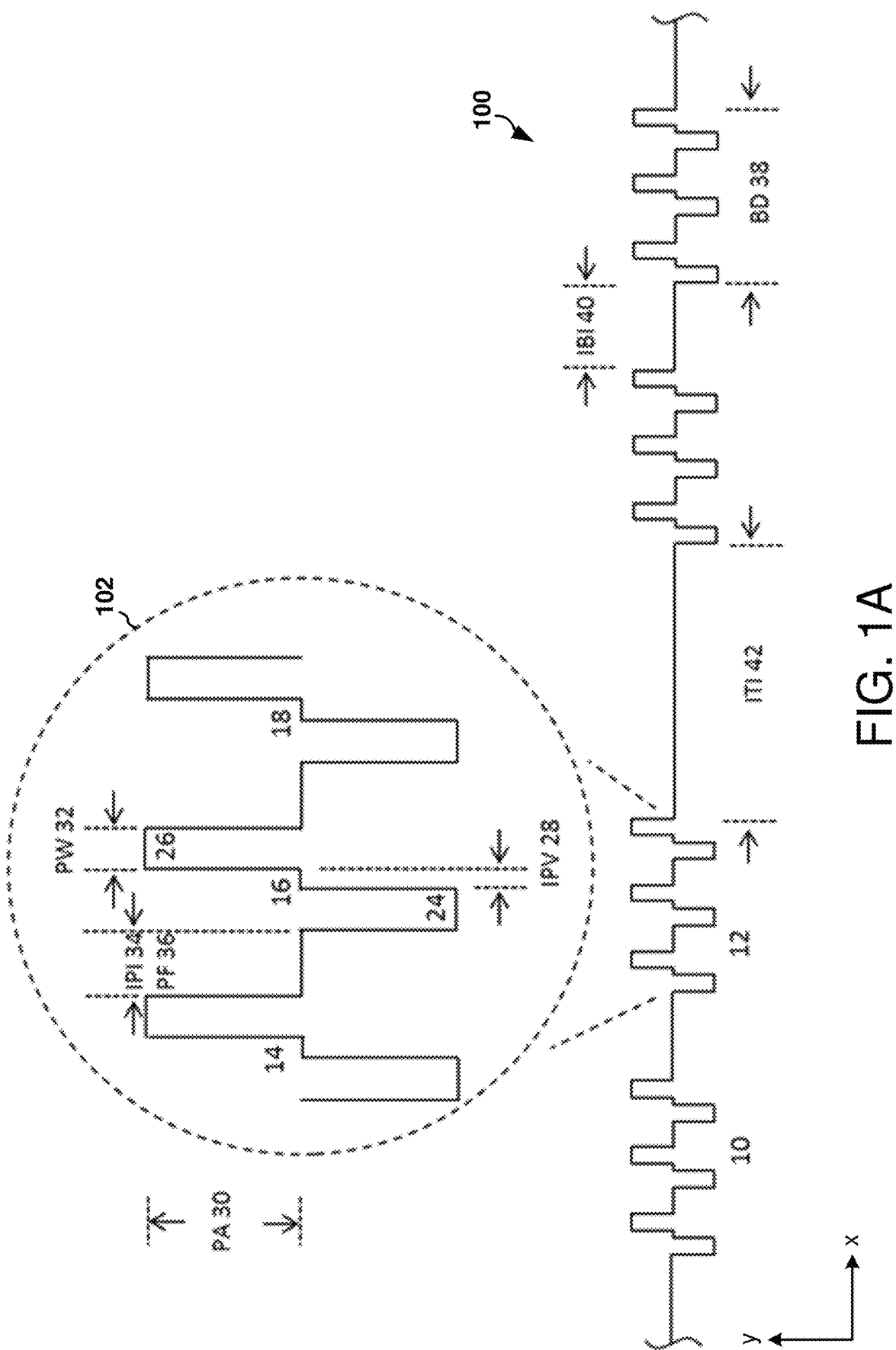
FIG. 1A is a graph of an instance of pulsatile electrical stimulation.
Figure 1B:
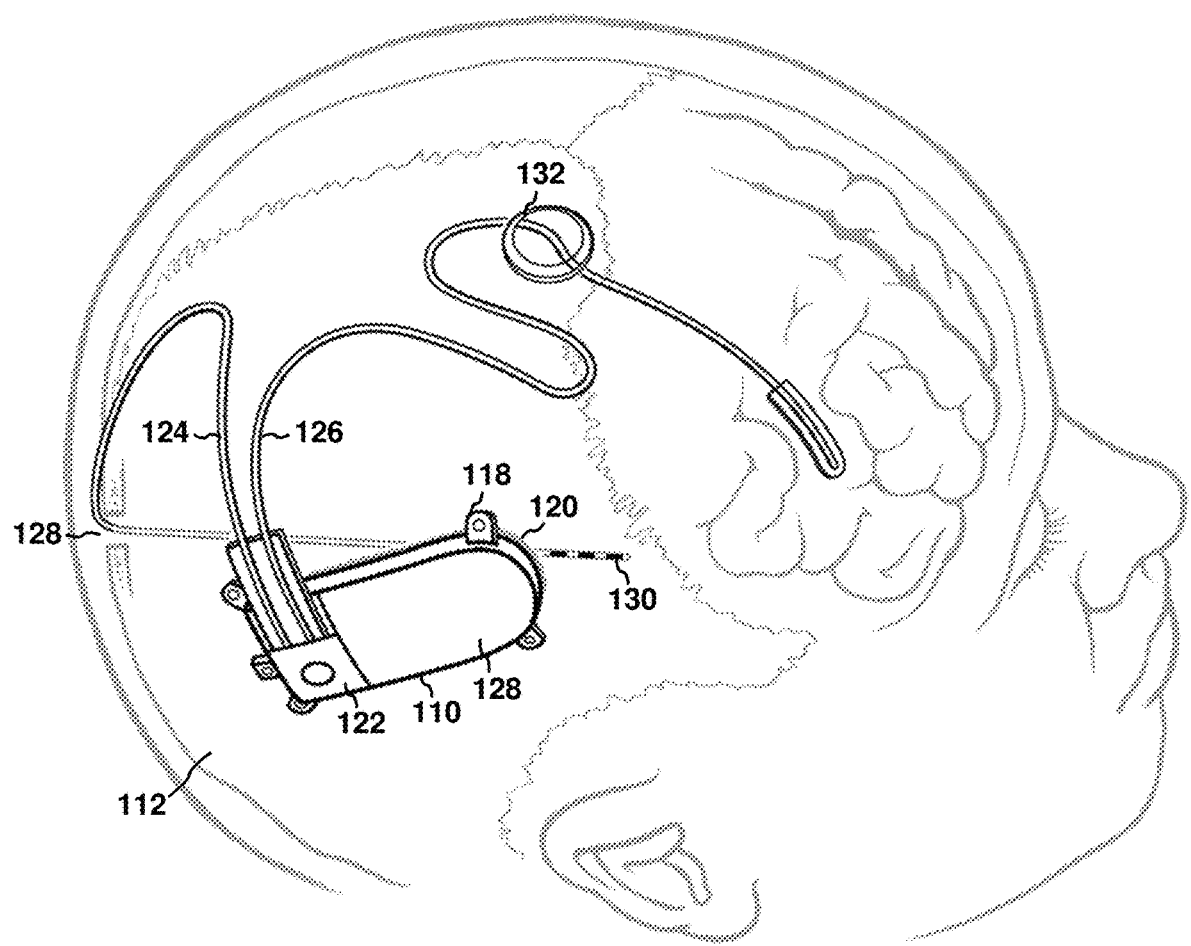
FIG. 1B is a perspective schematic view of a patient's cranium showing the placement of a neurostimulator, including leads extending to the patient's brain.

It will be appreciated that embodiments may be beneficially applied whenever a stimulation therapy is being applied to neural tissue to treat virtually any neurological disorder or condition, such as pain management, movement disorders including Parkinson's disease, psychological disorders, headaches, and for stroke recovery and Alzheimer's disease. Other disorders that for which implantable neurostimulation systems may be applied include tic disorders, such as Tourette's disorder; mood disorders, such as major depressive disorder and bipolar disorder; and anxiety disorders, such as obsessive-compulsive disorder Some parameters that may characterize an instance of stimulation therapy delivered by an implanted neurostimulator to the neural tissue of a patient will now be described with reference to FIG. 1A. This particular form of stimulation is pulsatile, charge-balanced, current-controlled electrical stimulation. The graph 100 is a time series representation of a series of pulses, delivered in a pair of "bursts" 10 and 12, with time on the horizontal x axis and amplitude, in milliamps, on the vertical y axis. The exploded view of the area 102 on the graph 100 represents one of the bursts (burst 12) comprised of a total three pulses 14, 16, and 18, each with a negative-going pulse portion 24 and a positive-going pulse portion 26. There is an interphase interval (IPV) 28, separating each negative-going and positive-going pulse portion 24, 26. Each pulse 14, 16, 18 is further characterized by a pulse amplitude, (PA) 30, and a pulse phase width (PW) 32. Between each pulse 14, 16, 18 is an inter-pulse interval (IPI) 34, the inverse of which corresponds to the frequency at which the pulses in the burst 12 are delivered, pulse frequency (PF) 36. The time it takes to deliver the three pulses 14, 16, 18 in the burst 12 is the burst duration (BD) 38. The time between bursts is the inter-burst interval (IBI) 40. The time between instances of therapy, which in the example shown in FIG. 1A is the time between each pair of bursts, is the inter-therapy interval (ITI) 42.

It will be appreciated that the range of possible values for each of the stimulation parameters described herein is established in part by the design constraints of the implantable pulse generator or neurostimulator. For the sake of discussion here, assume the following: The range of possible values for the interphase interval IPV 28 parameter is 0 to 1,000 ms; the range of possible values for the pulse amplitude PA 30 parameter is 0 to 12 milliamps (mA); the range of possible values for the pulse phase width PW 32 parameter is 40 to 1000 microseconds (μS); the range of possible values for the pulse frequency PF 36 parameter, which corresponds to the inverse of the inter-pulse interval IPI 34 is 1 to 333 Hz; the range of possible values for the burst duration BD 38 parameter is 10-5,000 milliseconds (ms); the range of possible values for the inter-burst interval IBI 40 parameter is 0 to 5,000 ms; and the range of possible values for the inter-therapy interval ITI 42 parameter is 0 to 60,000 ms. Collectively, these parameters and the range of possible values for each comprise the "parameter space" for this particular type of stimulation therapy.

In this description, "parameter subspace" refers to a collection of parameters and a range of possible values for each parameter where each range is something less than the full possible range for the parameter. A parameter subspace for the parameter space described above with reference to FIG. 1A may comprise a range of possible values for the pulse amplitude PA 30 parameter of 2.5 to 4.0 mA; a range of possible values for the pulse phase width PW 32 parameter of 450 to 600 μs; a range of possible values for the pulse frequency PF 36 parameter of 80 to 120 Hz; a range of possible values for the burst duration BD 38 parameter of 250 to 500 ms; a range of possible values for the inter-burst interval IBI 40 parameter of 100 to 200 ms; and a range of possible values for the inter-therapy interval ITI 42 parameter of 100 to 5,000 ms.

In this description, "stimulation parameter set" refers to a set of discrete values for each parameter in a parameter space (or parameter subspace). With reference to the parameters shown in FIG. 1A, a stimulation parameter set may comprise a pulse amplitude PA 30 of 3.0 mA; a pulse phase width, PW 32, of 500 μs; a pulse frequency, PF 36, of 100 Hz; a burst duration, BD 38, of 400 ms; an inter-burst interval, IBI 40, of 150 ms; and an inter-therapy interval, ITI 42, of 2,000 ms.

A neurostimulator may be programmed to deliver stimulation through one or more stimulation elements or stimulators, for example, electrodes, to a particular nerve or region of neural tissue patient's brain based on the type of disorder or disease. In epilepsy, for example, an objective may be to deliver stimulation to a location in the brain that is believed to be a focus of the patient's seizures, or to a pathway or circuit in the brain that is believed to be involved in the patient's seizures. The stimulation therapy may be delivered continuously over a period of time (all day, during the day, at night), on a scheduled basis (five times an hour, twice a day, for three hours every night), or in response to a trigger, such as a change in a state or condition of the patient. When stimulation therapy is delivered continuously or according to a schedule, it is sometimes referred to as "open-loop" stimulation. When it is delivered in response to a trigger, it is sometimes referred to as "responsive" or "closed-loop" stimulation. Depending on its design and capabilities, a single neurostimulator may be configured to deliver all three types of stimulation: continuous, scheduled, and responsive.

Epilepsy is characterized by episodic attacks often associated with abnormal behavior, symptoms and sensations, including for example, loss of consciousness, abnormal motor phenomena, psychic or sensory disturbances, or the perturbation of the autonomic nervous system. The disorder is a result of disturbances in the activity of the nerve cells or neural tissue, of the brain, which manifests in abnormal electrographic activity, which is sometimes referred to as "epileptiform activity". The abnormal activity can encompass any electrographic activity associated with the disorder, including that which occurs during a seizure ("ictal activity"), as a seizure is beginning (seizure onset), and even before seizure onset, which sometimes referred to as "precursor" activity, between seizures ("interictal activity"); and after a seizure ("post-ictal activity").

Electrographic activity can be measured in various ways. For example, a common way is to measure changes in field potential between electrodes to acquire a signal or waveform. These changes correspond to the aggregate activity of the neurons or nerve cells in the path of the electrodes. When field potential measurements result in what is often referred to as electroencephalographic signals or an electroencephalogram (EEG). Sometimes, when the source of the field potential measurements is electrodes implanted in the brain or on or under a surface of the brain (the dura mater), the result is referred to as electrocorticographic signals or an electrocorticogram (ECoG). Thus, an ECoG is a type of EEG, and either term may be used herein to refer to electrographic activity sensed from a patient's neural tissue.

It is generally preferable to be able to detect and treat a seizure at or near the point it begins electrographically (i.e., the electrographic seizure onset), or even before it begins. There is a distinction between an electrographic seizure onset and a clinical seizure onset. A "clinical seizure onset" refers to the time when symptoms of a seizure occur that are observable by a human being (i.e., a clinician (the patient's doctor or nurse), the patient's caregiver, or the patient himself). These symptoms may include involuntary muscle movements (ranging from twitching or tics to tonic/clonic movements) and neurophysiological effects such as lack of responsiveness (staring absently into space or loss of consciousness). An "electrographic seizure onset" refers to the time when a seizure begins in an ECoG or EEG. A patient's electrographic seizure onset does not always occur before the clinical seizure onset. However, if an electrographic seizure onset does occur before the corresponding clinical seizure onset, and the electrographic seizure onset is detected and effectively treated (for example, with stimulation therapy) then, the stimulation therapy may avoid or reduce the severity of the clinical symptoms of the seizure. For simplicity and readability, "seizure onset" will be used herein to mean "electrographic seizure onset", unless otherwise expressly noted.

Thus, a seizure onset is a neurological event that is particularly relevant to treatment of epilepsy, especially if the occurrence of the seizure onset can be used as a trigger to deliver stimulation therapy to the patient. A neurostimulation system manufactured by NeuroPace, Inc. (Mountain View, Calif.) under the trade name "RNS" can be configured to analyze the features of electrographic signals and recognize patterns in the signals, including patterns that may correspond to seizure onsets. The neurostimulator further can be configured to "detect" each pattern as an "event" when it occurs. Event detection then can trigger the neurostimulator to generate stimulation therapy (instances of which are defined in accordance with a stimulation parameter set) and deliver it through stimulators (e.g., electrodes) in response to the seizure onset. The NeuroPace, Inc. neurostimulation system is described, among other places, in U.S. Pat. No. 6,016,449, issued Jan. 18, 2000 to Fischell et al., entitled "System for the Treatment of Neurological Disorders." The disclosure of U.S. Pat. No. 6,016,449 is incorporated by reference herein in the entirety.

There are, however, different types of seizure onsets, and a single patient may experience more than one of them. Described in more detail below are (1) various ways in which seizure onsets are classified (e.g., by morphology of the characteristic waveform, presence or absence of rhythmic activity in the waveform, location in the brain from which the waveform is acquired) and (2) several seizure onset types (e.g., low voltage fast onset, high voltage beta onset, hypersynchronous onset, and spike and wave onset).

In addition, for two patients experiencing the same type of seizure onset, there may be variations in the features in the relevant ECoGs. For example, any of the morphology, rhythmicity, frequency or amplitude of an ECoG for one patient may be somewhat different than those same features in an ECoG of another patient reflecting the same seizure onset type. Thus, determining the probability that an event the responsive neurostimulator is configured to detect is a particular type of seizure onset can be challenging.

Similarly, it can be challenging to identify which stimulation parameter set is the most effective in treating a particular type of seizure onset. Indeed, there are many more stimulation parameter sets than there are identified seizure onset types. Assuming for the sake of illustration, a stimulation parameter space comprises the following: a pulse amplitude in the range of 0.5-5 mA, a pulse phase width in the range of 5-500 μS, a pulse frequency in the range of 1-250 Hz. With just those three parameters and those parameter value ranges, there are a staggering 5.5 million possible combinations for defining an instance of stimulation. Further, as a practical matter, a typical parameter space for a stimulation therapy would include more parameters and a wider range of possible values than used in this illustration.

Complicating matters further, not every patient with a certain type of seizure onset will respond the same to an instance of stimulation therapy. So a stimulation parameter set that works well in response to a certain type of seizure onset in Patient A may not work so well in response to the same type of seizure onset in Patient B.

In light of the foregoing, it would be desirable to configure a neurostimulation system that can: (1) assess the probability that a detected event corresponds to one of a plurality of seizure onset types; and (2) select a parameter subspace and a default stimulation parameter set based on the probability that the detected event is a particular seizure onset type. It further would be desirable to configure a neurostimulation system to integrate other data about a state of the patient in determining whether to (a) apply a stimulation parameter set within the parameter subspace or (b) apply the default stimulation parameter set, such that the neurostimulator will generate a stimulation therapy based on the applied stimulation parameter set and apply through stimulators (e.g., electrodes) to the patient's neural tissue. It would be still further desirable to assess whether a stimulation parameter set selected from within a parameter subspace may be adjusted, for example, by changing one or more values, to achieve a superior therapeutic result, thus optimizing the therapy for the patient. Embodiments of the neurostimulation system, components thereof, and method for using it described herein include these desirable features.

Seizure Onset Classification and Effectiveness of Stimulation Therapy

A patient can experience multiple types of seizures at different times, with different patterns of electrographic changes present at each seizure onset. Even though patients may not experience seizures identically, and therefore the changes in the electrographic signals in these patients at the onset of a seizure may not be identical, often the changes are similar enough to allow seizure onsets to be categorized into types. When appropriate, the seizure onset types that have been classified based on human observations, may be referred to herein as "human-defined seizure onset types" types" in order to distinguish them from seizure onset types that are created by a machine (e.g., using a clustering process).

These seizure onset types have also been observed in the data collected during clinical investigations. By way of example, the types of human-defined seizure onsets include but are not limited to: hypersynchronous seizure onset, low voltage fast seizure onset, spike and wave seizure onset, high voltage semi-rhythmic spiking (high voltage beta), hypersynchronous, attenuation, spike and wave, as well as onsets that contain multiple types of activity, e.g. delta brush, that will be referred to here as a multiple seizure onset.

Several human-defined seizure onset types are described in "Morphological patterns of seizures recorded intracranially," Spencer, S. S., Guimaraes, P., Katz, A., Kim, J., and Spencer, D. Epilepsia, 33:537-545 (1992) and "Intracranial EEG seizure-onset patterns in neocortical epilepsy," Lee, S. A., Spencer, D. D., and Spencer, S. S. Epilepsia, 41:297-307 (2000). It should be understood that these broad seizure onset types may be broken down into individual components for classification. In other words, each seizure onset type may be identified by combining distinct set of features occurring in the electrographic activity, such as features comprising or relating to the shape of the waveform(s) represented in the electrographic activity (e.g. sharp or round), and the rhythmicity, frequency, and relative amplitude of the electrographic activity.

Seizure onsets may be classified into types based on the morphology (i.e. the combination of the waveform shape, rhythmicity, frequency and relative amplitude) of the electrographic signal or ECoG. Six of these types are referred to herein as the "hypersynchronous seizure onset," the "high voltage beta seizure onset", the "multiple seizure onset", the "low voltage fast seizure onset," the "spike and wave seizure onset, and the "attenuation seizure onset".

Figure 8A:
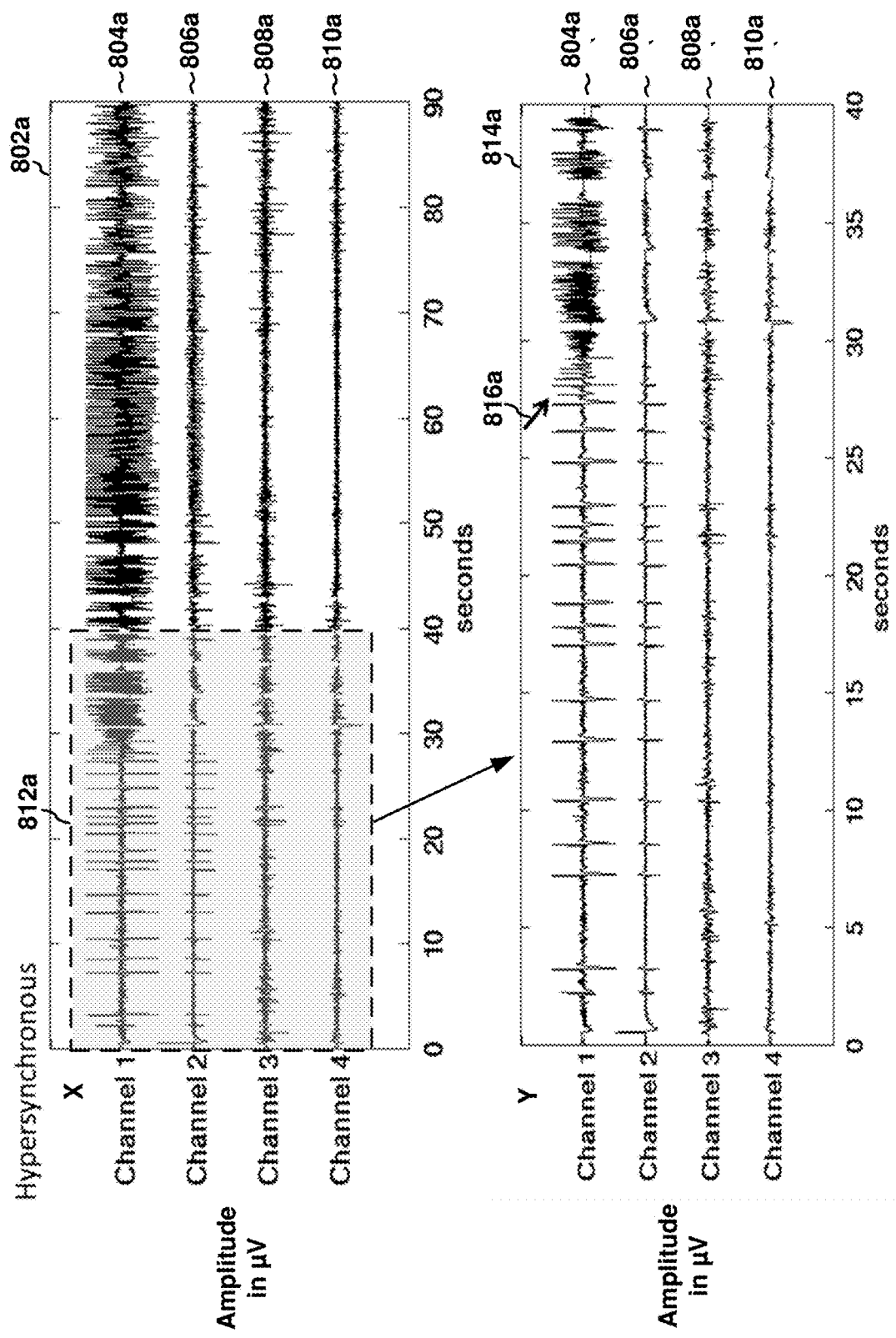
FIG. 8A is an illustration of a waveform set corresponding to a hypersynchronous seizure onset.

Referring now to FIG. 8A, the electrographic signal that embodies the hypersynchronous seizure onset type evidences high voltage spiking lasting for more than 5 seconds. The top graph X shows the electrographic signal or ECoG recorded simultaneously on each of four sensing channels from a patient, namely, electrographic signals 804a, 806a, 808a, and 810a. In the case of the neurostimulation system for epilepsy described in these embodiments where the electrographic signals are field potential measurements, a sensing channel in the neurostimulator receives a bipolar signal representative of the difference in electrical potential between two electrodes. Which two electrodes comprise which channels may be a programmable feature of the neurostimulation system. The bottom graph Y of FIG. 8A is a detail of section 812a of the graph X, in which one of the four electrographic signals 804a', 806a', 808a', and 810a' evidences a hypersynchronous seizure onset.

More particularly, the "hypersynchronous" activity is deemed to occur when spiking at high voltage (generally 5 to 7 times the amplitude of the baseline activity) is clearly evident in an electrographic signal, and such activity lasts for more than about 5 seconds. In the example of FIG. 8A, a hypersynchronous seizure onset 816a is evident in the waveform 804a, 804a' comprising the electrographic signal recorded on the top channel (i.e., Channel 1).

Stimulation therapy for hypersynchronous seizure onsets can be effective when it comprises either theta burst stimulation or desynchronizing stimulation. Theta burst stimulation is a type of stimulation generally defined when the following stimulation parameters have the following general ranges of values: pulse amplitude: 0.8-1.5 mA; frequency: 6-10 Hz; interburst interval: 2-5 ms; pulse phase width: 200-400; and burst duration: 3-5 seconds). Desynchronizing stimulation is a category of stimulation generally defined when the following stimulation parameters have the following ranges of values: pulse amplitude: 0.8-1.5 mA; pulse frequency: 100-150 Hz; inter-burst interval: 100-166 ms; pulse width: 75-150 µs; and burst duration: 0.5-2 seconds.

Figure 8B:
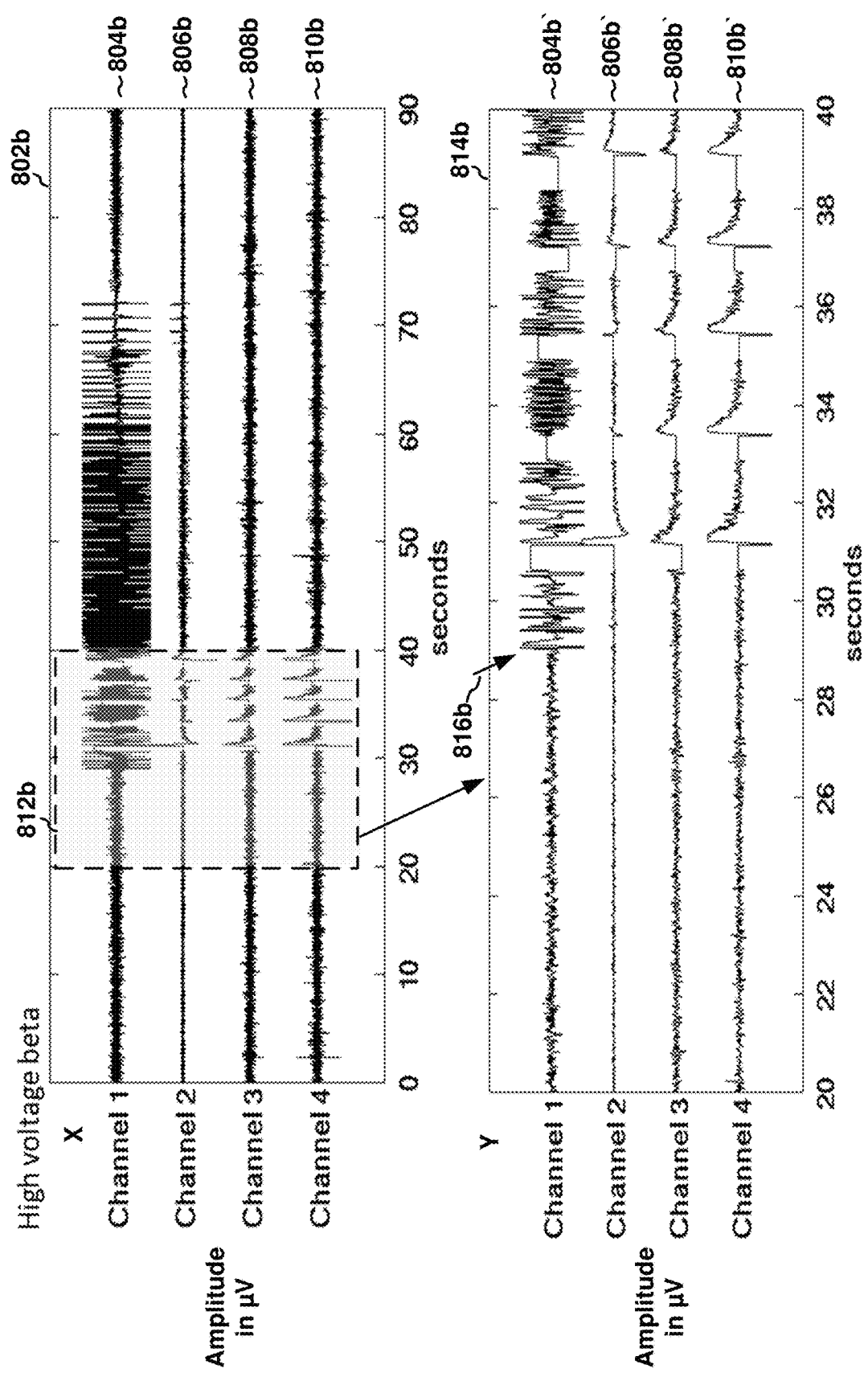
FIG. 8B is an illustration of a waveform set corresponding to a high voltage beta seizure onset.

Referring now to FIG. 8B, the electrographic signal that embodies the high voltage beta seizure onset type evidences a burst of repetitive high voltage spikes. The top graph X shows the ECoG recorded simultaneously on each of four sensing channels from a patient, namely, electrographic signals 804b, 806b, 808b, and 810b. The bottom graph Y of FIG. 8B is a detail of section 812b of the graph X, in which one of the four electrographic signals 804b', 806b', 808b', and 810b' evidences a high voltage beta seizure onset.

More particularly, "high voltage beta" activity comprises regular rhythmic activity, generally in the range of about 13-30 Hz. In the example of FIG. 8B, such regular rhythmic activity is evident in the ECoG 804b, 804b' of Channel 1.

Stimulation therapy for high voltage beta seizure onsets can be effective when it comprises biphasic stimulation delivered at a very high frequency (greater than or equal to about 200 Hz).

Referring now to FIG. 8C, the electrographic signal that embodies the multiple seizure onset type evidences rhythmic slow waves on which higher frequency activity is superimposed. The top graph X shows the ECoG recorded simultaneously on each of four sensing channels from a patient, namely, electrographic signals 804c, 806c, 808c, and 810c. The bottom graph Y of FIG. 8C is a detail of section 812c of the graph X, in which one of the four electrographic signals 804c', 806c', 808c', and 810c' evidences rhythmic waves less than or equal to 8 Hz on which activity at a frequency of greater than 20 Hz is superimposed. The waveform 804c' including the seizure onset 816c corresponds to Channel 1. Similar seizure onset activity is also present in the waveform 806c' at 818c, but the seizure onset appears earliest on Channel 1.

Stimulation therapy for multiple seizure onsets can be effective when it comprises voltage-controlled stimulation (the other examples of stimulation therapy mentioned in this section refer to current-controlled stimulation), particularly, voltage-controlled stimulation delivered as a 1 Hz square wave for about a minute for each instance of stimulation therapy.

Figure 8D:
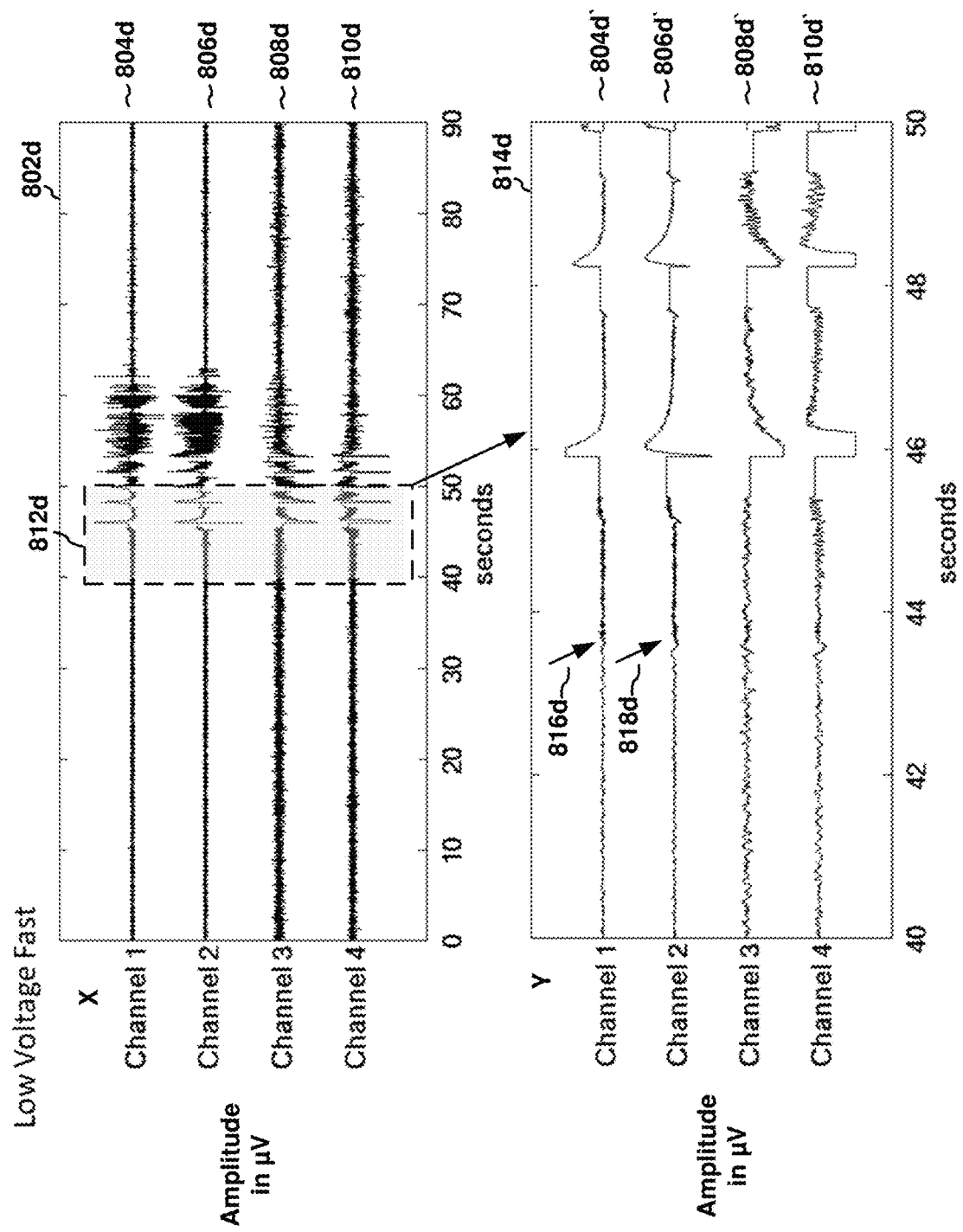
FIG. 8D is an illustration of a waveform set corresponding to a low voltage fast seizure onset.

Referring now to FIG. 8D, the electrographic signal that embodies the low voltage fast seizure onset type evidences low amplitude high frequency, quasi-sinusoidal, or relatively rounded, waveforms. The top graph X shows the electrographic signal or ECoG recorded simultaneously on each of four sensing channels from a patient, namely, electrographic signals 804d, 806d, 808d, and 810d. The bottom graph Y of FIG. 8D is a detail of section 812d of the graph X, in which some of the four electrographic signals 804d', 806d', 808d', and 810d' evidence a low voltage fast seizure onset.

More particularly, the "low voltage fast" activity is deemed to occur when rhythmic activity greater than about 13 Hz is clearly evident in an electrographic signal, and the amplitude either decreases compared to baseline or remains similar to baseline activity when the rhythmic activity begins. In the example of FIG. 8D, seizure onsets 816d, 818d are evident in the waveforms 804d', 806d' comprising the electrographic signals recorded on the top two channels of graph A (i.e., Channels 1 and 2). The earliest seizure onset is evident simultaneously on both Channels 1 and 2.

Stimulation therapy for low voltage fast seizure onsets can be effective when it comprises short bursts (≤200 ms) of high frequency (≥100 Hz) pulses and the bursts are applied to the brain at or near the focus of the electrographic activity (i.e., where the neural tissue from which the low voltage fast seizure onset arises).

Referring now to FIG. 8E, the electrographic signal that embodies the attenuation seizure onset type evidences a flattening of the amplitude of the ECoG accompanied by a loss of content across all frequency bands lasting for a period of time greater than or equal to about 30 seconds. The attenuation seizure onset 816e is marked on Channel 1 in the set 802e of ECoGs in FIG. 8E. The attenuation seizure onset can also be seen simultaneously on the three other channels and are marked as 818e, 820e, 822e in the set 802e of ECoGs in FIG. 8E.

Stimulation therapy for attenuation seizure onsets can be effective when it comprises an instance of stimulation delivered at a high amplitude, such as at a high current when the stimulation is current-controlled stimulation. In some cases, since attenuation of electrographic activity in general can be associated with death, an objective of such therapy may be to alert a relevant portion of the patient's brain to avoid death.

Attenuation of electrographic activity can also occur after a seizure or seizures (post-ictally). Post-ictal attenuation is thought to be associated with sudden unexplained death in epilepsy (SUDEP) in some patients. Peri-ictal interventions (i.e., interventions around the time of an attenuation seizure onset) may prevent or at least reduce the risk of SUDEP. The interventions may include administering oxygen, oropharynygeal suction, and turning the patient to the lateral recumbent position. (In this study, there was no significant difference between the intervention methods with respect to the duration of the post-ictal attenuation, suggesting that all of the interventions were equally beneficial.) These interventions may reduce the duration of post-ictal attenuation and thus avoid SUDEP.

Another study by "Case-control study of SUDEP," Langan, Y., Nashef, L., and Sander, J. W. Neurology, 64:1131-1133 (2005) supports the hypothesis that prompt intervention in response to post-ictal attenuation, particularly when the seizure(s) that result in the attenuation occur at night (nocturnally), can reduce the risk of SUDEP.

Thus, being able to detect attenuation in electrographic activity may be beneficial other than just when the attenuation comprises an attenuation seizure onset type. A neurostimulation system may be configured to trigger an output other than stimulation therapy in response to detection of attenuation in ECoGs, such as an alert to a caregiver so that the caregiver can intervene. Additionally or alternatively, when attenuation of electrographic activity is detected, a neurostimulation system may be configured to send a trigger to another component, either of the neurostimulation system or otherwise, implantable or external, to provide an intervention, such as a diaphragm stimulator to stimulate respiration or a cardiac device to restore a regular cardiac rate and rhythm.

A neurostimulation system further may be configured to respond to prolonged attenuation of electrographic activity with stimulation therapy, such as in the form of high amplitude stimulation, which is designed to produce a sensation for the patient that might be arousing in some way, e.g., will cause pain or a visual experience.

Still another intervention when post-ictal attenuation in electrographic activity is detected may be a form of drug therapy. Respiratory dysfunction may occur in epilepsy patients during a seizure, and this may contribute to SUDEP. Selective serotonin reuptake inhibitors (SSRIs) can reduce the severity of ictal oxygen desaturation in patients with partial onset epilepsy "Serotonin reuptake inhibitors are associated with reduced severity of ictal hypoxemia in medically refractory partial epilepsy," Bateman, L. M., Li, C. S., Lin, T. C., and Seyal, M. Epilepsia, 51:2211-2214 (2010). Increasing serotonergic tone may enhance brainstem respiratory center excitability. Therefore, upon detecting post-ictal attenuation of electrographic activity or a physiological condition related to post-ictal attenuation is detected (such as oxygen desaturation), a neurostimulation system may be configured to stimulate an area of the brain comprising an arousal regions (e.g. serotonergic nuclei) to prevent SUDEP.

Referring now to FIG. 8F, the electrographic signal that embodies the spike and wave seizure onset type evidences sharp, spiky high amplitude low frequency waveforms. FIG. 8F shows a waveform set 802f comprising electrographic signals 804f, 806f, 808f, and 810f recorded from a patient simultaneously on four sensing channels (Channels 1-4).

More particularly, the "spike and wave" activity is deemed to occur when spike-and-wave complexes, typically occurring at a frequency of 2-4 Hz, are evident in an electrographic signal, and the amplitude is medium to high voltage relative to baseline (e.g. an increase in amplitude of 3-5 times compared to baseline activity). In the example of FIG. 8F, the criteria for a spike-and-wave complex is met simultaneously in the waveforms 804f, 806f, 808f, 810f on Channels 1-4, at 816f, 818f, 820f, 822f.

In contrast to the case with low voltage fast seizure onsets, spike and wave seizure onsets often do not respond well to short bursts of high frequency electrical pulses. Rather, stimulation therapy for spike and wave seizure onsets can be effective when it comprises long bursts (≥3000 ms) of relatively low-frequency (≤7 Hz) sinusoidal stimulation.

In addition to the human-defined seizure onset types, a seizure onset type may be determined by a machine using a clustering approach, described in more detail below, where ECoG records are clustered into groups based on similarity between the extracted features. These will likely be distinct from the human-defined seizure onset types.

Factors in addition to the type of seizure onset may be relevant to whether stimulation therapy defined in accordance with a particular parameter set is effective. For example, knowing from where in the brain the electrographic activity evidencing the seizure onset originates can be relevant to which stimulation therapy will work well for the patient. A stimulation parameter set for a hypersynchronous seizure onset that is effective when the electrographic activity originates from the temporal lobe may not be as effective when the electrographic activity originals extratemporally.

Whether the electrographic activity that evidences a seizure onset originates near to or remotely from the sensors (e.g., sensing electrodes) may also influence which stimulation parameter sets are effective for the patient. For example, if the sensing and stimulating electrodes are remote from the seizure onset, a higher stimulation pulse amplitude (e.g. >2 mA) may be preferred. It may be possible in some circumstances to differentiate local epileptiform from that which has been propagated from somewhere else in the brain remote from the sensor, based on characteristics observed in the recorded electrographic activity. See, e.g., "Characterization and comparison of local onset and remote propagated electrographic seizures recorded with intracranial electrodes," Schiller, Y., Cascino, G. D., Busacker, N. E., and Sharbrough, F. W. Epilepsia, 39:380-388 (1998) (examining local and remote electrographic patterns relating to both mesiotemporal and neocortical seizure onsets). In particular, when rhythmic rounded theta-delta (up to about 7.5 Hz) waveforms are observed in electrographic activity, the electrographic activity is generally deemed to comprise propagated activity.

In addition, differences in the underlying pathology may also influence the effectiveness of a particular parameter set. For instance, the hippocampus of a patient with a lot of sclerotic tissue may not respond the same as the hippocampus of a patient without sclerosis. Similarly whether the patient has a dysplastic lesion, encephalomalacia or other anatomical abnormality may influence the type of stimulation that will be effective in reducing the frequency of their seizures. Furthermore, the type of underlying tissue pathology may influence the electrographic seizure onset activity "Intracranial electroencephalographic seizure-onset patterns: effect of underlying pathology," Perucca, P., Dubeau, F., and Gotman, J. Brain, 137:183-196 (2014).

Thus, it will be appreciated that being able to classify electrographic activity into a seizure onset type and knowledge of other information, such as that concerning the origin or other characteristics of the electrographic activity comprising the seizure onset type, may enable selection of parameter values for a stimulation parameter set that will lead to effective stimulation therapy for a patient.

Figure 3:
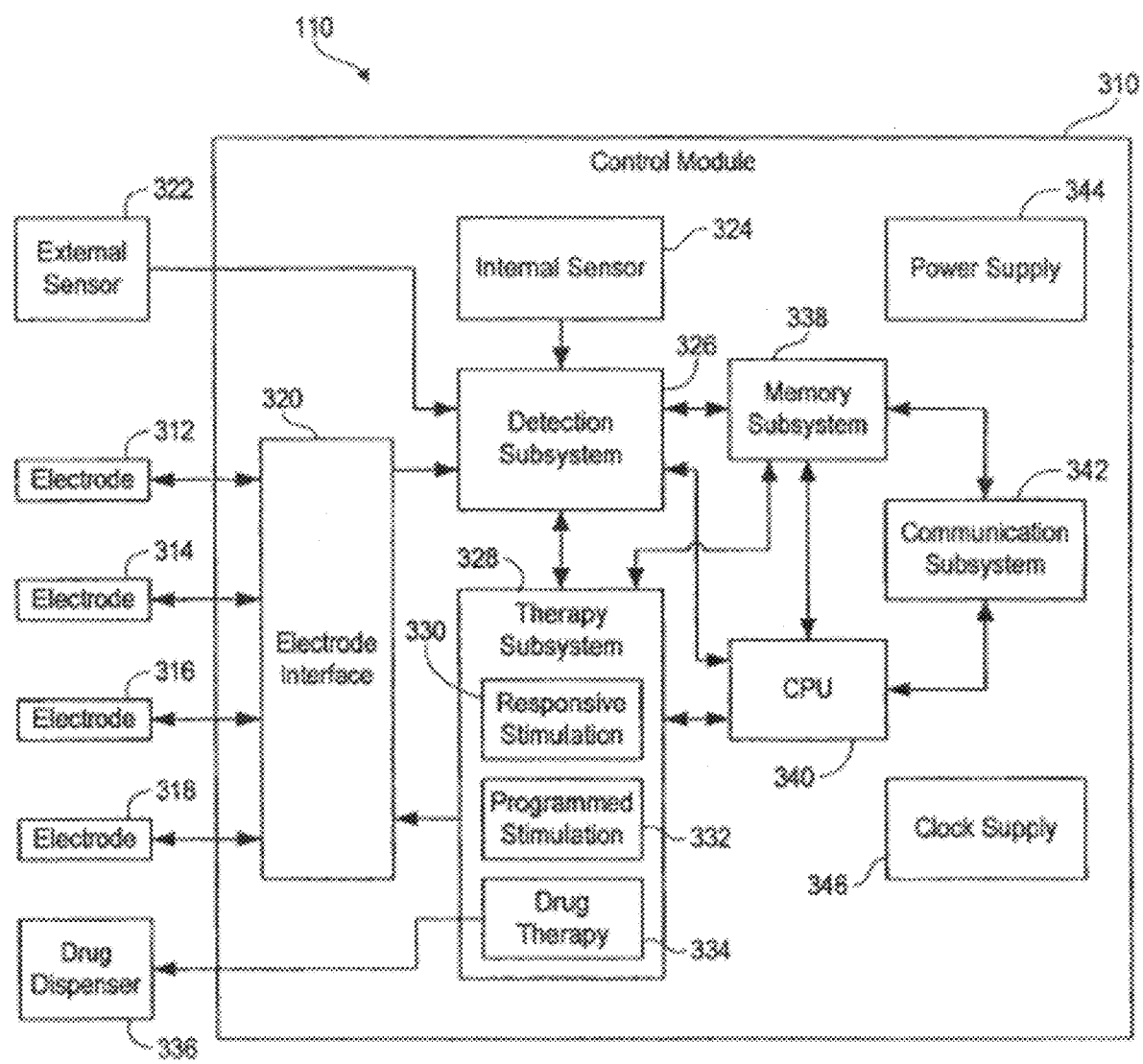
FIG. 3 is a block diagram illustration of the major functional subsystems of a neurostimulator.
Figure 4:
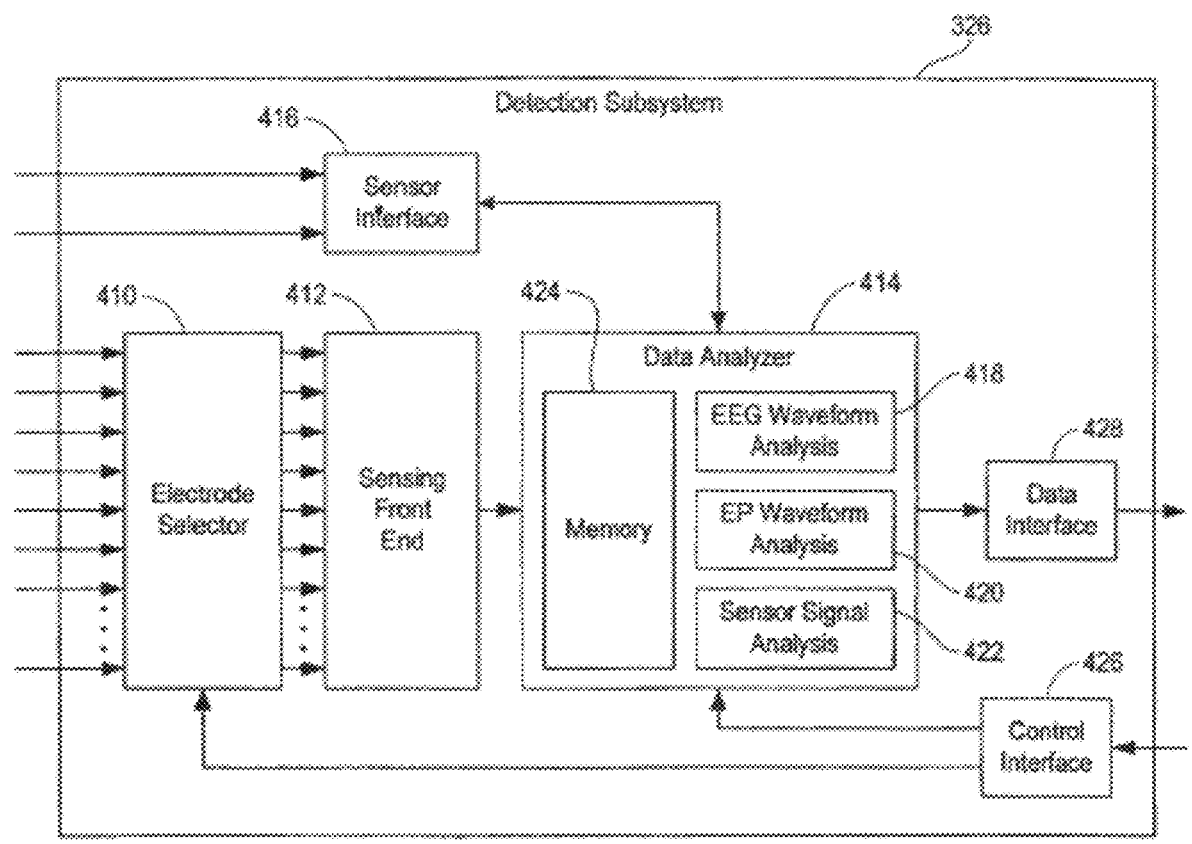
FIG. 4 is a block diagram illustration of the functional components of the detection subsystem of the neurostimulator shown in FIG. 3.
Figure 9A:
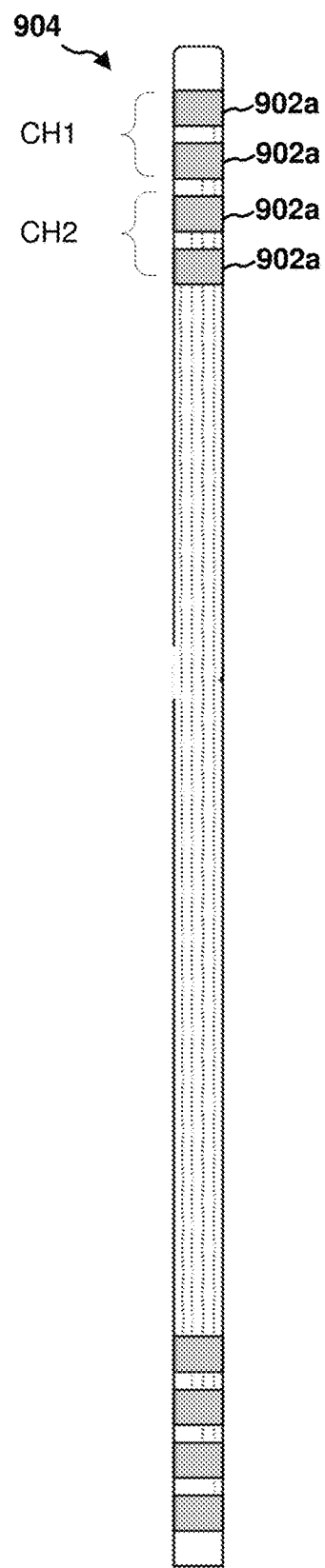
FIG. 9A is a schematic illustration of a deep brain stimulation lead having four ring electrodes at its distal end.
Figure 9B:
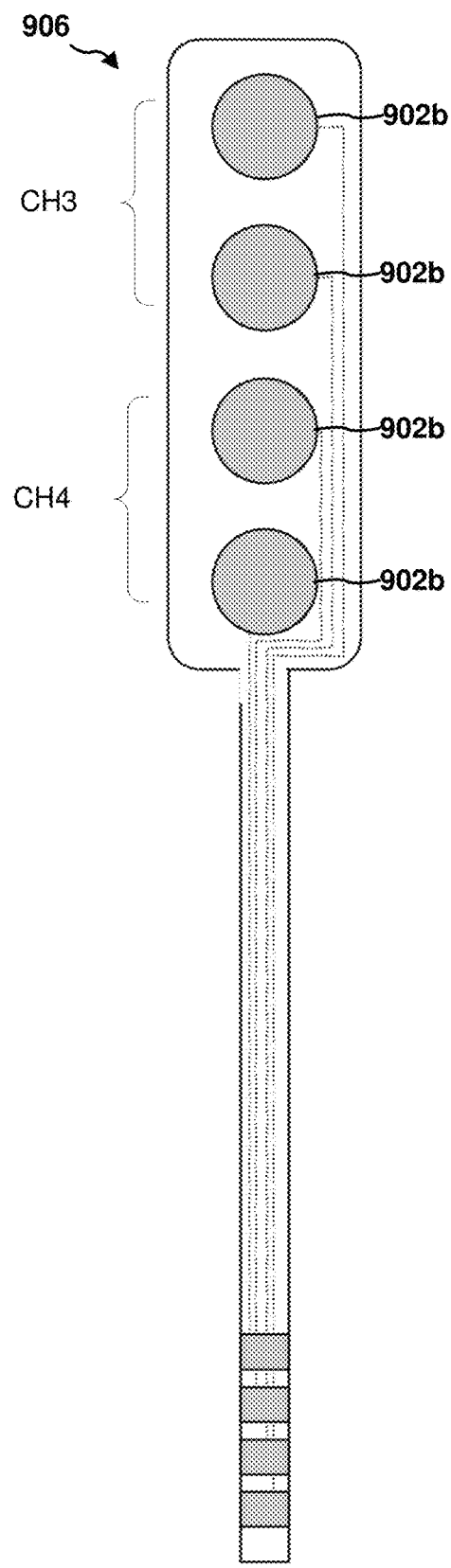
FIG. 9B is a schematic illustration of a cortical lead having four electrodes at its distal end.

Detecting Electrographic Activity Relevant to Seizure Onsets and Stimulation Parameter Set Selection Referring now to FIGS. 1-6, FIGS. 9A and 9B, and FIGS. 14, 17-19, and 21, an implantable neurostimulator system can be configured to receive with an implanted neurostimulator 110 electrographic signals (or ECoGs) sensed from a patient on one or more sensing channels (see, e.g., the sensor interface 416, the electrode selector 410, and the sensing front end 412 of FIG. 4). The input to each sensing channel may be defined by the change in potential in the electrical field measured between two electrodes. The neurostimulator 110 may be connected to one or more electrode-bearing leads 124, 126 (see also, the lead 904 in FIG. 9A and the lead 906 in FIG. 9B). A lead may be configured as a depth or deep brain lead 124, 904 such that the electrodes 902a near the distal end thereof will be positioned at a location in the patient's brain once the deep brain lead is implanted. Another lead may be configured as a cortical or cortical strip lead 126, 906 such that the electrodes 902b near the distal end thereof will be positioned on a surface of the patient's brain, usually on or under the dura mater.

The neurostimulator includes "modules" and "subsystems" that enable the neurostimulator to process the sensed electrographic activity and analyze it on each sensing channel to extract features that likely are relevant to determining whether the electrographic activity evidences a neurological event, such as a seizure onset (see, e.g., the control module 310 of FIG. 3 and the detection subsystem 326 of FIGS. 3 and 4). When the neurostimulator determines from the extracted features that a neurological event has occurred, it detects the neurological event and registers it as a "detection". Which features the neurostimulator extracts from the monitored electrographic activity is determined by the values of parameters that govern the operation of various algorithms or "detection tools" (a "detection parameter set"). These values are programmable and adjustable so that the neurostimulator can be configured to look for different patterns or characteristics in electrographic activity.

The neurostimulator further includes modules and/or subsystems for storing in memory some of the sensed electrographic activity when certain conditions are met (see, e.g., the memory subsystem 338 of the control module 310 of FIG. 3, and the memory 424 of the detection subsystem 326 in FIG. 4). For example, a neurostimulator configured to sense electrographic activity on four sensing channels may store an ECoG record for each channel in an ECoG file whenever the extracted features suggest that an electrographic seizure has occurred.

Figure 2:
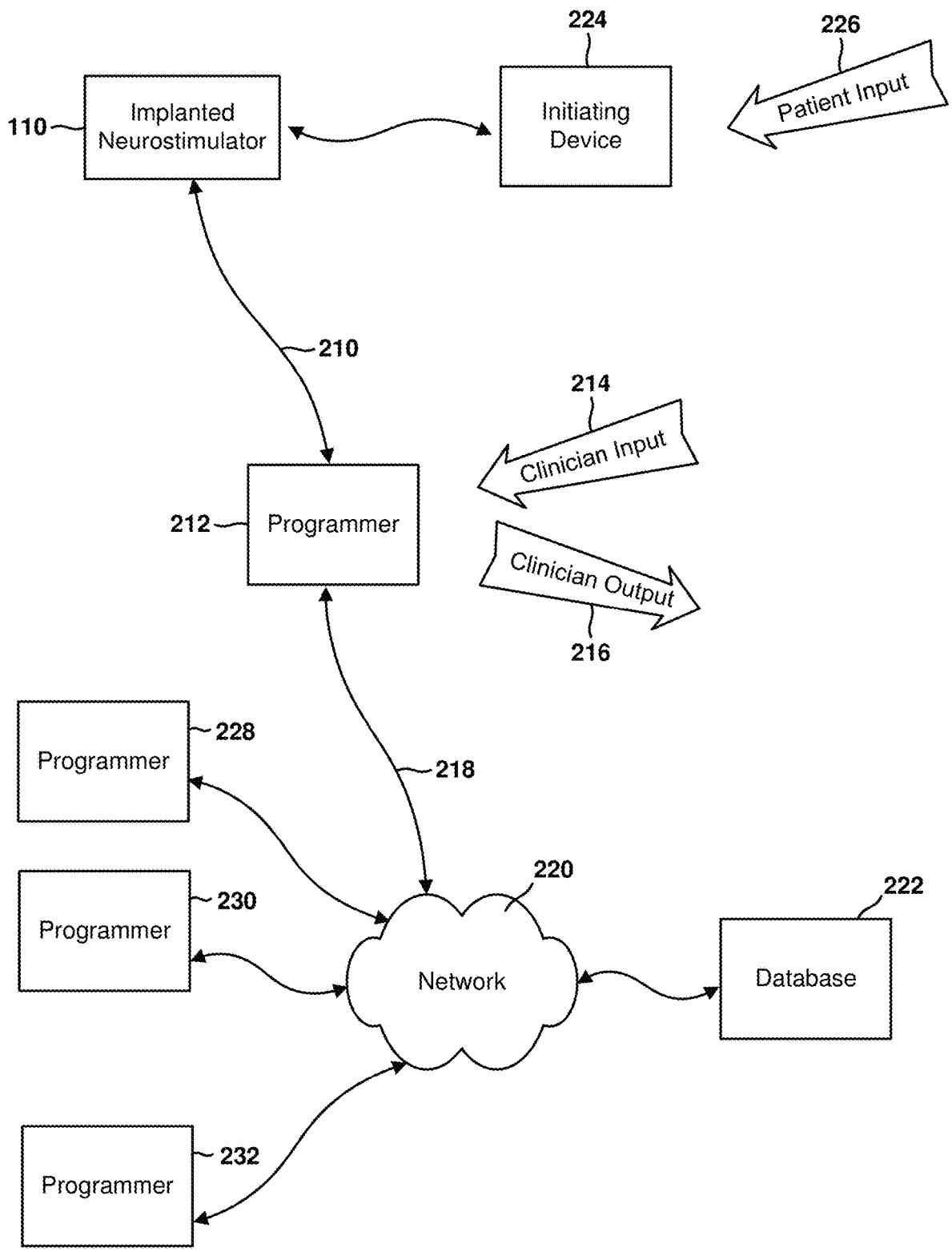
FIG. 2 is a block diagram illustration of a context in which a neurostimulator is implanted and operated, including various items of external equipment.

The neurostimulator also includes a subsystem that enables the neurostimulator to communicate bidirectionally (the communication subsystem 342 of the control module 310 of FIG. 3) with one or more external components (see, e.g., the initiating device 224, the programmers 212, 228, 230, and 232 and the database 222 of FIG. 2). The communication subsystem 342 allows the implanted neurostimulator 110 to receive instructions from (for example, settings for the values of the parameters in a detection parameter set or a stimulation parameter set) an external component. The communications subsystem 342 also allows the implanted neurostimulator 110 to send information to external components 224, 212, 228, 230, 232, 222). The information received by the external component from the neurostimulator can include both information that the neurostimulator has previously recorded and stored and information that is being sensed from the patient in real time during the time the communications link is established.

The neurostimulator also can be configured with modules or subsystems to generate stimulation therapy, including electrical stimulation therapy, and then deliver it to the patient, for example, through the same electrodes 902a, 902b on the leads 904, 906 that are used to sense the electrographic activity. See, e.g., the control module 310 of FIG. 3 and the therapy subsystem of FIGS. 3 and 5. An instance of electrical stimulation therapy is defined according to the values of each of the parameters in a stimulation parameter set. The stimulation parameter values are programmable and adjustable.

Figure 5:
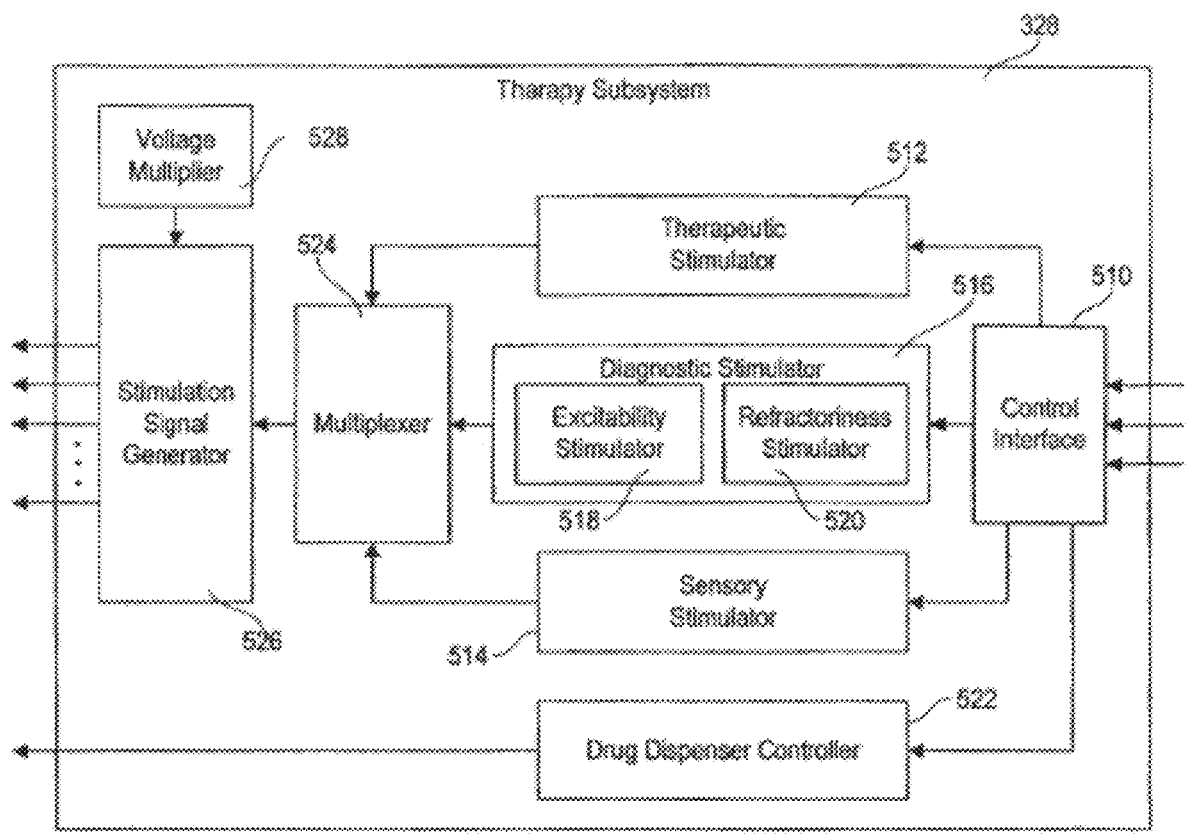
FIG. 5 is a block diagram illustration of the functional components of the therapy subsystem of the neurostimulator shown in FIG. 3.
Figure 6:
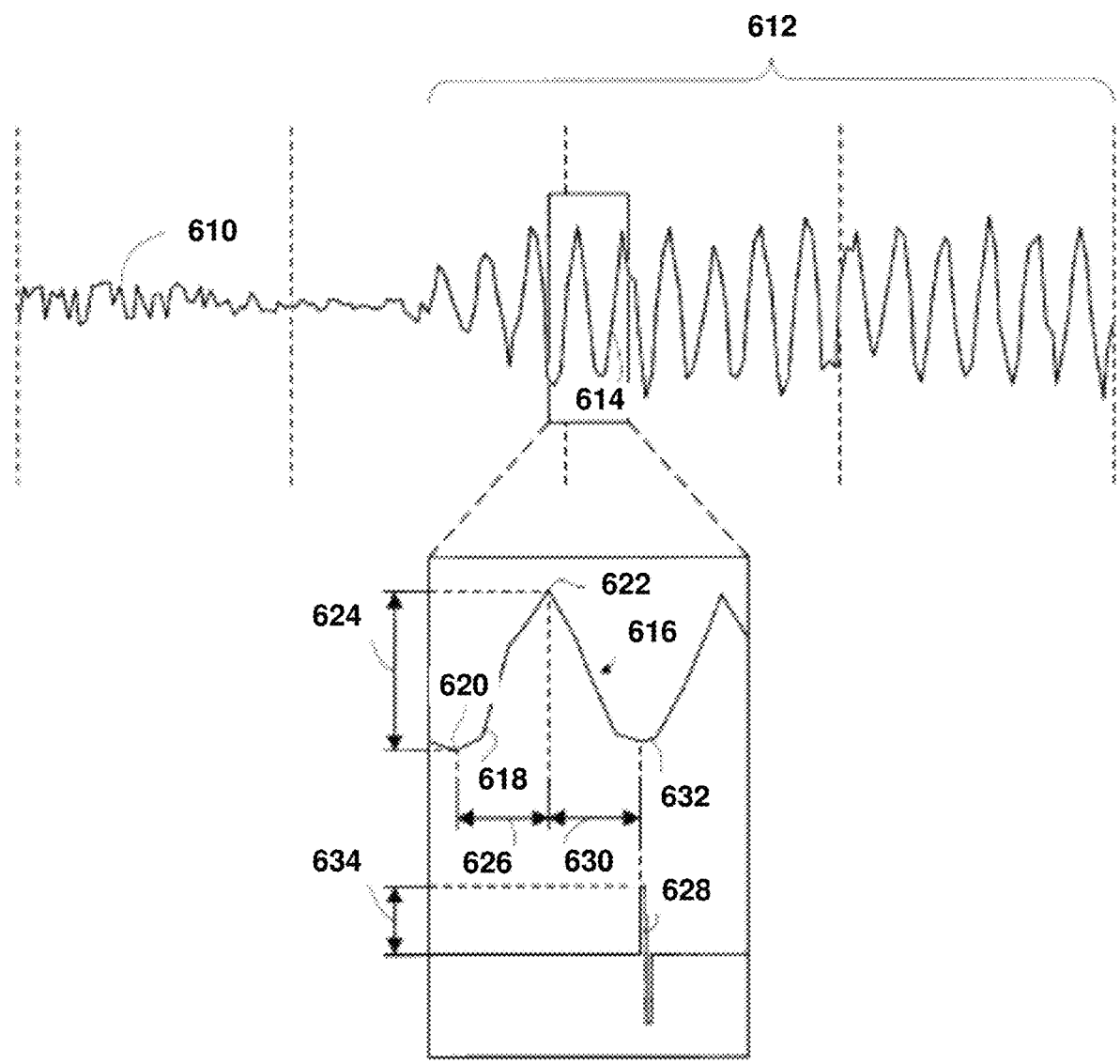
FIG. 6 is an illustration of several possible electrical stimulation modalities according to an embodiment.

The neurostimulator further comprises modules and/or subsystems that can be configured to generate and deliver stimulation therapy in response to detection by the neurostimulator of a neurological event (see, e.g., the therapy subsystem of FIG. 5, and the schematic of FIG. 6, showing an example of when a neurostimulator would deliver an instance of stimulation therapy 628 in response to detection of a neurological event 614, in electrographic activity 612).

The neurostimulator may determine the stimulation parameter set with which to generate an instance of stimulation therapy based on which type of neurological event the neurostimulator detected. To accomplish this, the neurostimulator may use a mapping function (see, e.g., the mapping function module of FIGS. 14 and 21).

Figure 19:
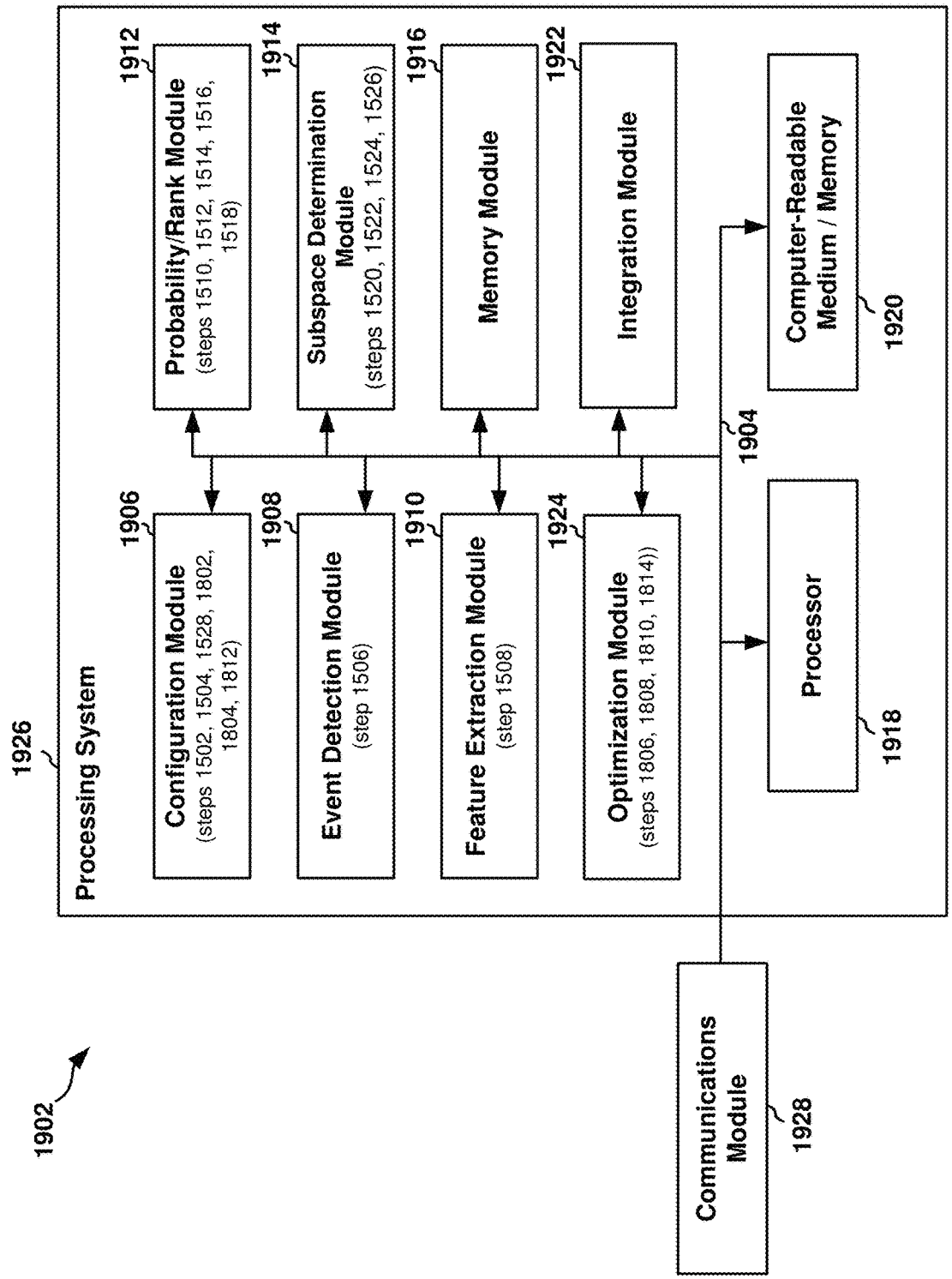
FIG. 19 is a block diagram illustration of an external device configured to implement the stimulation parameter subspace selection method of FIG. 15, the integration method associated with FIG. 17, and the optimization method of FIG. 18.
Figure 21:
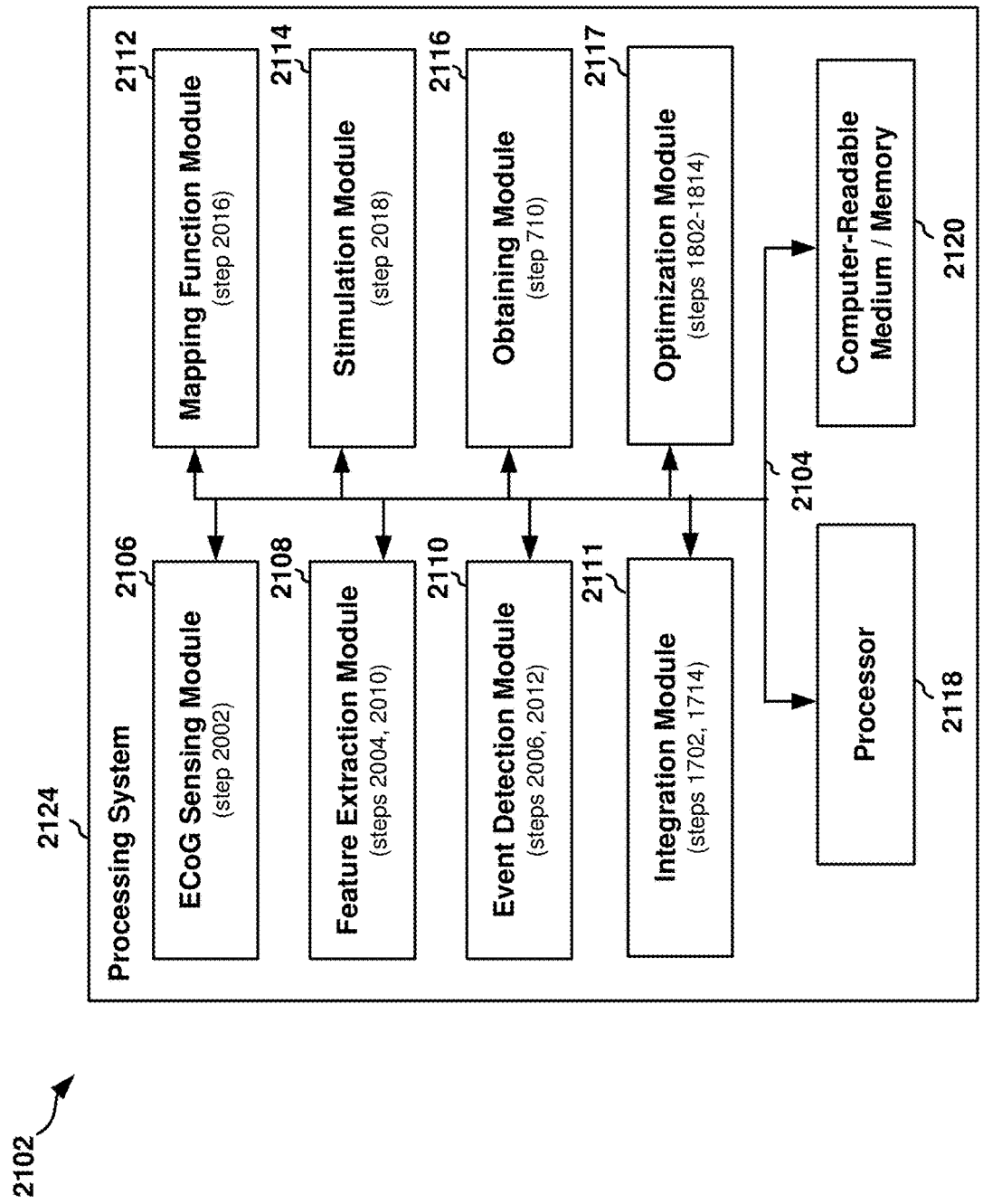
FIG. 21 is a block diagram illustration of neurostimulator configured to implement the electrical stimulation therapy delivery method of FIG. 20.

The neurostimulator system is further configured to integrate a detected neurological event type with other information about a state of the patient or about prior values of the programmable parameters of the neurostimulator ("prior settings") in the process of determining which stimulation parameter set to use for generating an instance of stimulation therapy (see, e.g., the integration module of FIGS. 19 and 21).

The neurostimulator system is still further configured to optimize the values of the parameters within a stimulation parameter subspace for a stimulation parameter set, to achieve the best therapeutic result for the patient (see, e.g., the optimization module of FIGS. 19 and 21).

Any or all of the mapping function, the integration, and the optimization may be accomplished with modules: (1) in the neurostimulator, supplied with inputs originating internally or externally of the patient, or some combination of the two; (2) in one of the external components of the neurostimulation system, or (3) in both the neurostimulator and an external component of the neurostimulation system.

The responsive neurostimulation system generally, and the mapping function module, the integration module, and optimization module in particular, are each described in more detail below.

The Responsive Neurostimulation System: General Description and Use and Implanting the Neurostimulator and Leads FIG. 1 is an illustration of an intracranially implanted neurostimulator 110. The neurostimulator 110 is affixed in the patient's cranium 112 by way of a ferrule 118. The ferrule 118 is a structural member adapted to fit into a cranial opening, attach to the cranium 112, and retain the neurostimulator 110. To implant the neurostimulator 110, a craniotomy is performed in the parietal bone anterior to the lambdoidal suture to define an opening 120 slightly larger than the neurostimulator 110. The ferrule 118 is inserted into the opening 120 and affixed to the cranium 112, ensuring a tight and secure fit. The neurostimulator 110 is then inserted into and affixed to the ferrule 118.

The neurostimulator 110 includes a lead connector 122 adapted to receive one or more electrical leads, such as a first deep brain stimulation lead 124 and a second cortical lead 126. The lead connector 122 acts to physically secure the leads 124, 126 to the neurostimulator 110, and facilitates electrical connection to conductors in the leads 124, 126 coupling one or more respective electrodes to circuitry within the neurostimulator 110. The lead connector 122 accomplishes this in a substantially fluid-tight environment with biocompatible materials.

The leads 124, 126 include a flexible elongated member having one or more conductors. As shown, the leads 124, 126 are coupled to the neurostimulator 110 via the lead connector 122. The proximal portion of the first lead 124 is generally situated on the outer surface of the cranium 112 (and under the patient's scalp), and extends between the neurostimulator 110 and a burr hole 128 or other cranial opening. The distal portion of the deep brain stimulation lead 124 enters the cranium 112 and is coupled to at least one depth electrode 130 implanted in a desired location in the patient's brain. The proximal portion of the second lead 126 is generally situated on the outer surface of the cranium 112 (and under the patient's scalp), and extends between the neurostimulator 110 and a burr hole (not visible) or other cranial opening. The distal portion of the cortical lead 126 enters the cranium 112 through the burr hole and is secured in place by a burr hole cover 132. The distal portion of the cortical lead 126 includes at least one cortical electrode (not visible) implanted in a desired location on the patient's brain.

The neurostimulator 110 includes a durable outer housing 128 fabricated from a biocompatible material, such as titanium. As the neurostimulator 110 is self-contained, the housing 128 encloses a battery and any electronic circuitry necessary or desirable to provide the functionality described herein, as well as any other features. A telemetry coil or other antenna may be provided outside of the housing 128 (and potentially integrated with the lead connector 122) to facilitate communication between the neurostimulator 110 and external devices.

FIG. 2 is an illustration of an implanted neurostimulator 110 operating in conjunction with external equipment. The neurostimulator 110 may include a selectable part-time wireless link 210 to external equipment such as a programmer 212. The wireless link 210 may be established by moving a wand having communication capabilities and coupled to the programmer 212 into communication range of the neurostimulator 110. The programmer 212 can then be used to manually control the operation of the device, as well as to transmit information to or receive information from the neurostimulator 110.

The programmer 212 is capable of performing a number of advantageous operations. In particular, the programmer 212 is able to specify and set variable parameters in the neurostimulator 110 (e.g., detection parameter sets and stimulation parameter sets) to adapt the function of the device to meet the patient's needs, upload or receive data from the neurostimulator 110 to the programmer 212, download or transmit program code and other information from the programmer 212 to the neurostimulator 110, or command the neurostimulator 110 to perform specific actions or change modes as desired by a physician operating the programmer 212. To facilitate these functions, the programmer 212 is adapted to receive clinician input 214 and provide clinician output 216; data is transmitted between the programmer 212 and the neurostimulator 110 over the wireless link 210.

The programmer 212 may be used at a location remote from the neurostimulator 110 if the wireless link 210 is enabled to transmit data over long distances. For example, the wireless link 210 may be established by a short-distance first link between the neurostimulator 110 and a transceiver, with the transceiver enabled to relay communications over long distances to a remote programmer 212, either wirelessly or via a wired communications link.

The programmer 212 may also be coupled via a communication link 218 to a network 220 such as the internet. This allows any information uploaded from the neurostimulator 110, as well as any program code or other information downloaded to the neurostimulator 110, to be stored in a database 222 at one or more data repository locations, which may include various servers and network-connected programmers like the programmer 212. This would allow a patient (and the patient's physician) to have access to important data, including past treatment information and software updates, essentially anywhere in the world that there is a programmer (like the programmer 212) and a network connection.

In some embodiments, the wireless link 210 from the neurostimulator 110 may enable a transfer of data from the neurostimulator to the database 222 without any involvement by the programmer 212. In these embodiments, the wireless link 210 may be established by a short-distance first link between the neurostimulator 110 and a transceiver, with the transceiver enabled to relay communications over long distances to the database 222, either wirelessly or via a wired communications link.

The neurostimulator 110 may be adapted to receive communications from an initiating device 224 (sometimes referred to as a "remote monitor"), typically controlled by the patient or a caregiver. Accordingly, patient input 226 from the initiating device 224 is transmitted over a wireless link to the neurostimulator 110. The patient input 226 may be used to cause the neurostimulator 110 to switch modes, e.g., turn between on to off, or perform an action, e.g., store a record of electrographic data. Preferably, the initiating device 224 is able to communicate with the neurostimulator 110, and possibly in the same manner the programmer 212 does. The link may be unidirectional, allowing commands to be passed in a single direction from the initiating device 224 to the neurostimulator 110. Alternatively, the link may be bi-directional, allowing status and data to be passed back from the neurostimulator to the initiating device 224. The initiating device 224 may be a computer configured as a laptop, a tablet, a smart phone or some other portable or mobile device.

In some embodiments, the programmer 212 is primarily a commercially available personal computer, such as in the form of a laptop, a tablet, or a workstation having a suitable central processing unit (CPU), user interface and accessories such as a keyboard, mouse and display, and running a standard operating system. The programmer also might be implemented as a turnkey system, with a custom software package so that the unit can be used only for functions dedicated to the neurostimulation system, for example, to minimize cybersecurity vulnerabilities.

The programmer 212 has the capability to allow a clinician to create or modify a patient-specific collection of information related to the detection of a neurological event, e.g., a seizure onset, and the treatment of the neurological event. The patient-specific information may include algorithms and associated algorithm parameters for the detection of relevant neurological events, and stimulation parameters for treatment.

The database 222 may be adapted to communicate over the network 220 with multiple programmers, including the programmer 212 and additional programmers 228, 230, and 232. Programmers may be located at various medical facilities and physician offices at widely distributed locations. Accordingly, if more than one programmer has been used to upload ECoG records or ECoG files from a patient's neurostimulator 110, the records or files may be aggregated via the database 222 and available thereafter to any of the programmers connected to the network 220, including the programmer 212.

FIG. 3 is a block diagram of a neurostimulator 110. The neurostimulator 110 includes several subsystems making up a control module 310. The control module 310 is capable of being coupled to a plurality of electrodes 312, 314, 316, and 318, each of which may be connected to the control module 310 via a lead for sensing, stimulation, or a combination of the two functions. Thus, an electrode 312, 314, 316, 318 may be configured as either a sensor or a stimulator or both. The lead is coupled to the control module 310 through a lead connector 122. Although four electrodes are shown in FIG. 3, more electrodes may be available depending on the number of implanted leads and the number of electrodes per lead. For example, a pair of implanted lead, each with four electrodes may be used to provide a total of eight electrodes.

The electrodes 312-318 are connected to an electrode interface 320. The electrode interface 320 is capable of selecting each electrode as required for sensing and stimulation. The electrode interface 320 may also provide any other features, capabilities, or aspects, including but not limited to amplification, isolation, and charge-balancing functions, that are required for a proper interface with neurological tissue. The electrode interface 320, an external sensor 322, and an internal sensor 324 are all coupled to a detection subsystem 326. The electrode interface 320 is also connected to a therapy subsystem 328.

The detection subsystem 326 includes a data analyzer 414 with an EEG waveform analysis module 418 for analyzing ECoGs. The EEG waveform analysis module 418, which will be described in greater detail below, is adapted to receive ECoG and other signals from the electrodes 312-318, through the electrode interface 320, and to process those signals to detect electrographic activity indicative of a seizure, a seizure onset, or any other electrographic activity or neurological event of interest.

The detection subsystem 326 may also include further sensing and detection functions, adapted to receive signals from the external sensor 322 or the internal sensor 324. These sensors 322, 324 may provide signals or other data elements representative of other physiological conditions, electrophysiological or not, such as temperature, blood pressure, etc.

For example, to detect a clinical seizure or patient orientation it may be advantageous to provide an accelerometer, an angular velocity sensor, or an EMG sensing electrode as the external sensor at a location remote from the neurostimulator 110. Other sensors, such as for temperature, blood pressure, blood oxygenation, drug concentration, or neurotransmitter concentration might be implemented as part of the external sensor 322 or the internal sensor 324. The external sensor 322 can be connected to the neurostimulator 110 by a lead or by wireless communication, such as a wireless intrabody signaling technique.

Such other sensors or probes may be either hard wired or in wireless communication with the neurostimulator 110 so that the neurostimulator may monitor physiological data other than data acquired using the electrodes. For example, probes for oximetry and micro/macroelectrode configurations for accomplishing voltammetric measurements relating to neurochemical concentrations may be used to provide other physiological data to the neurostimulator 110. A probe may be used to acquire a signal corresponding to the level of the near-infrared wavelength characteristic of light absorption by oxygenated hemoglobin ($HbO_2$). This signal may be used to estimate a level of neural activity. For instance, the neurovascular coupling system causes vasodilation and increased cerebral perfusion in response to neural activity, such that, after an initial drop in oxygenated hemoglobin when the increased neural activity begins, the increased neural activity is then accompanied by an increase in oxygenated hemoglobin.

Variations of sensors or probes may be implemented using transducers for additional sensing modalities such as optical infrared spectroscopy. A given sensing modality may rely upon active electronics provided in the lead, especially at a distal portion of a lead close to where the physiological data is being sensed, to acquire physiological data for use by the neurostimulator 110. Alternatively, a given sensor may be associated locally with active electronics and the sensor information acquired may be communicated to the neurostimulator 110 wirelessly.

The therapy subsystem 328 is capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. This form of stimulation, sometimes referred to as "programmed stimulation," is provided by a programmed stimulation function 332 of the therapy subsystem 328. Preferably, therapeutic stimulation is also provided in response to abnormal events detected by the data analysis functions of the detection subsystem 326. This form of stimulation, namely responsive stimulation, is provided by a responsive stimulation function 330 of the therapy subsystem 328.

The therapy subsystem 328 and the data analysis functions of the detection subsystem 326 are in communication. This facilitates the ability of therapy subsystem 328 to provide responsive stimulation as well as an ability of the detection subsystem 326 to blank the amplifiers while stimulation is being performed to minimize stimulation artifacts.

The therapy subsystem 328 is also capable of a drug therapy function 334, in which a drug is dispensed from a drug dispenser 336, which may be integral with the control module 310 or an external unit. As with electrical stimulation, this capability can be provided either on a programmed basis or responsively, after an event of some kind is detected by the detection subsystem 326.

The control module 310 includes a memory subsystem 338 and a central processing unit (CPU) 340, which can take the form of a microcontroller. The memory subsystem 338 is coupled to the detection subsystem 326, and may receive and store data representative of sensed ECoGs and other sensor data. The memory subsystem 338 is also coupled to the therapy subsystem 328 and the CPU 340. In addition to the memory subsystem 338, the CPU 340 is also connected to the detection subsystem 326 and the therapy subsystem 328 for direct control of those subsystems.

The control module 310 also includes a communication subsystem 342. The communication subsystem 342 enables communication between the neurostimulator 110 and the outside world, particularly the external programmer 212. The communication subsystem 342 may include a telemetry coil enabling transmission and reception of signals, to or from an external apparatus, via inductive coupling. Alternative embodiments of the communication subsystem 342 could use an antenna for an RF link or an audio transducer for an audio link. The control module 310 also includes a power supply 344 and a clock supply 346. The power supply 344 supplies the voltages and currents necessary for each of the other subsystems. The clock supply 346 supplies substantially all of the other subsystems with any clock and timing signals necessary for their operation.

It should be observed that while the memory subsystem 338 is illustrated in FIG. 3 as a separate functional subsystem, the other subsystems may also require various amounts of memory to perform the functions described above. Furthermore, while the control module 310 is preferably a single physical unit contained within a single physical enclosure, it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 340 and the other functional subsystems may also vary.

The neurostimulator 110 generally interacts with the programmer 212 as described below. Data stored in the memory subsystem 338 can be retrieved by the patient's physician through the wireless communication link 210, which operates through the communication subsystem 342 of the neurostimulator 110. A software operating program run by the programmer 212 allows the physician to read out a history of events detected including ECoG information before, during, and after each event, as well as specific information relating to the detection of each event. The programmer 212 also allows the physician to specify or alter any programmable parameters of the neurostimulator 110. The software operating program also includes tools for the analysis and processing of recorded ECoG records to assist the physician in developing optimized detection parameters for each specific patient, and to identify which therapies are most advantageously associated with what event characteristics.

A neurostimulator 110 may be programmed by a physician to acquire physiological data from one or more sensing locations in a patient, and to process, analyze and evaluate the acquired physiological data in an effort to determine whether the acquired physiological data evidences what the neurostimulator 110 is programmed to recognize as a detected event. Physiological data may include electrographic data, such as ECoGs, or non-electrographic data, such as pH data and neurochemical data. A detected event may include, for example, an epileptic seizure or a seizure onset.

With respect to electrographic data, the neurostimulator 110 may be programmed with detection parameters (i.e., a detection parameter set) related to the operation of one or more analysis tools. These analysis tools are described further below and may include one or more of a half-wave tool, a line length tool, and an area tool. The neurostimulator 110 may process a segment of an acquired electrographic signal, e.g. ECoG, using one or more of the analysis tools to determine if the segment satisfies an event detection criterion corresponding to one of the detection parameters. If the criterion is satisfied, an event is considered to be detected.

With respect to non-electrographic data, the neuro stimulator 110 may be programmed to detect an event when a measure of such data is below or above a certain threshold level or trends too low, too high, or the like. Such measures may be, for example, a level or concentration of a neurotransmitter sensed by an external sensor 322 of internal sensor 324 of the neurostimulator 110.

The neurostimulator 110 may be further programmed to record data in the memory subsystem 338 related to the occurrences of the detected events. For example, the neurostimulator 110 may record the segment of the acquired electrographic signal for which a detection criterion was satisfied. The neurostimulator 110 may also record one or more time features related to the detected event, such as the time of the detected event, the time of the end of the detected event, and the duration of the detected event. Measures of non-electrographic data may also be recorded.

Patients may also to provide an input to the device, for instance via swiping a magnet over the device, to indicate the occurrence of a clinical event, e.g. clinical seizure. As noted above, the clinical symptoms that led to the conclusion that patient is having a seizure may occur after or before an electrographic seizure onset or seizure. Thus, a "clinical seizure" is distinct from an "electrographic seizure." The running count of the number of clinical events may be stored in the memory subsystem 338. Then the number of clinical events occurring logged in the device over a particular period of time (e.g., 24 hours), may provide a measure of how effective the stimulation therapy is for the particular patient.

FIG. 4 illustrates details of the detection subsystem 326. Inputs from the electrodes 312-318 are on the left and connections to other subsystems are on the right. Signals received from the electrodes 312-318 are received in an electrode selector 410. The electrode selector 410 allows the device to select which electrodes 312-318 should be routed to which individual sensing channels of the detection subsystem 326, based on commands received through a control interface 426 from the memory subsystem 338 or the CPU 340. Preferably, each sensing channel of the detection subsystem 326 receives a bipolar signal representative of the difference in electrical potential between two selectable electrodes. The outer housing 128 of the neurostimulator 110 also can be used as an electrode in acquiring a measure of electrographic activity.

The electrode selector 410 provides signals corresponding to each pair of selected electrodes to a sensing front end 412, which performs amplification, analog to digital conversion, and multiplexing functions on the signals in the sensing channels. Preferably, any of the electrodes 312-318 can be unused (i.e., not connected to any sensing channel), coupled to a positive or negative input of a single sensing channel, coupled to the positive inputs of multiple sensing channels, or coupled to the negative inputs of multiple sensing channels.

A multiplexed input signal representative of all active sensing channels is fed from the sensing front end 412 to a data analyzer 414. The data analyzer 414 may be a special-purpose digital signal processor (DSP) adapted for use in some embodiments, or in some alternative embodiments, may comprise a programmable general-purpose DSP. The data analyzer 414 may be configured to perform three functions, namely, an EEG waveform analysis function 418, an electrophysiological waveform analysis function 420, and a sensor signal analysis function 422. It will be recognized that some or all of these functions can be performed with the same software or hardware in the data analyzer 414, by simply operating with different parameters on different types of input data. It is also possible to combine the three functions in many ways to detect neurological events or conditions, or to identify event characteristics. The data analyzer 414 may have its own scratchpad memory area 424 used for local storage of data and program variables when the signal processing is being performed.

The data analyzer 414 may be configured to analyze data it acquires corresponding to field potential measurements sensed using electrodes with one or all of three tools, known as the half-wave tool, the line-length tool, and the area tool. These tools are described in more detail below and, for example, in U.S. Pat. No. 6,810,285 for "Seizure Sensing and Detection Using an Implantable Device", issued Oct. 26, 2004; and U.S. Pat. No. 7,966,073 for "Differential Neurostimulation Therapy Driven By Physiological Therapy" issued Jun. 21, 2011, each of which is incorporated herein by reference in the entirety. The tools may be implemented in a combination of hardware and software, or entirely in one or the other, depending on overall system requirements such as power consumption limitations.

The half-wave tool, the line-length tool, and the area tool each may be characterized as a tool for analyzing electrographic signals. There may be multiple instances of each of these tools in the data analyzer 414, having detection parameters that can be programmed with different values of different instances of the tools selectable to operate on the data processed through different sensing channels. The results of the tools may be used alone or in combination to decide whether an "event" should be deemed to have been detected in the sample of the signal analyzed. Event in this context may refer to a neurological event associated with a neurological disorder. For example, in the case of epilepsy, an event may be one or both of an epileptic seizure or a seizure onset.

The half-wave tool measures characteristics of an ECoG signal related to the dominant frequency content of the signal. In general terms, a half wave is an interval between a local waveform minimum and a local waveform maximum. Each time a signal changes directions—from increasing to decreasing, or from decreasing to increasing—a new half wave is identified. The half-wave tool further identifies those half waves having a duration that exceeds a minimum duration criterion and an amplitude that exceeds a minimum amplitude criterion, as "qualified half waves." The number of qualified half waves within a limited time period is a quantity of interest, as it may be representative of neurological events manifested in the specified frequency range corresponding to the half wave criteria. The half wave tool, particularly when used on filtered ECoG data, can be used to identify the presence of signals in particular frequency ranges over certain periods of time, such as a frequency range that correlates well with a time when a patient is experience seizure activity. In an embodiment, for example, the analysis performed by the detection module includes detection of power within a frequency band, such as from 13 to 30 Hertz, by analyzing half-waves that occur in one or more time windows in a sampled electrographic signal sensed from the patient's brain and acquired by the neurostimulator 110.

The line length analysis tool is a simplification of waveform fractal dimension, allowing a consideration of how much variation an ECoG signal undergoes. Accordingly, the line length analysis tool enables the calculation of a "line length" for an ECoG signal within a time window. Specifically, the line length of a digital signal represents an accumulation of the sample-to-sample amplitude, variation in the ECoG signal within a time window. Stated another way, the line length is representative of the variability of the input signal. A constant input signal will have a line length approaching zero representative of substantially no variation in the signal amplitude, while an input signal that oscillates between extrema from sample to sample will approach the maximum line length. It should be noted that while "line length" has a mathematical-world analogue in measuring the vector distance travelled in a graph of the input signal, the concept of line length as treated herein disregards the horizontal (X) axis in such a situation. The horizontal axis herein is representative of time, which is not combinable in any meaningful way with information relating to the vertical (Y) axis, generally representative of amplitude.

The area analysis tool is a simplification of waveform energy. Accordingly, the area analysis tool in some embodiments enables the calculation of the area under the ECoG waveform curve within a time window. Specifically, the area function is calculated as an aggregation of the ECoG's signal total deviation from zero over the time window, whether positive or negative. The mathematical-world analogue for the area function is the mathematical integral of the absolute value of the ECoG function (as both positive and negative signals contribute to positive energy). Once again, the horizontal axis (time) makes no contribution to the area under the curve as treated herein. Accordingly, an input signal that remains around zero will have a small area, while an input signal that remains around the most-positive or most-negative values (or oscillates between those values) will have a high area.

Any of the three detection tools summarized above can be used in connection with any of the three functions of the data analyzer 414, and can be easily tuned to operate on essentially any kind of source data.

Different or additional tools may be used to evaluate ECoG waveforms, other electrophysiological waveforms and other sensor data. For example, an ECoG waveform may be analyzed in the frequency domain by a tool that involves fast Fourier transforms (FFTs). The analysis tools may be used alone or in combination (e.g., in a Boolean combination) to analyze the physiological data sensed from the patient. A tool or tools may be implemented entirely by the neurostimulator 110 or in part by the implant and in part by one or more external components. Physiological data acquired by the neurostimulator 110 may be subjected to more than one tool at the same time or to one tool followed by another tool.

The analyzing may include comparing a result of an algorithm or algorithms with one or more thresholds, fixed or dynamic, or other values. The results can be logically combined, thresholded, trended, or subjected to further analyses or processing steps as necessary to detect neurological events or states, to assess effectiveness of stimulation subspace, or to identify other characteristics in the acquired physiological data according to embodiments.

Any detection tool or other algorithm for analyzing data with the detection subsystem 326 easily may be tuned to operate on essentially any kind of source data. It will be apparent that detection of a pathological event can include the condition occurring when the output of one of these analysis tools exceeds or falls below a threshold, such as a programmable parameter representing the threshold between normal physiological variation and pathological neural activity. It also will be apparent that pathological event may be deemed to have been 'detected' when a combination of conditions occurs, such as a Boolean AND combination, Boolean OR combination, or other logical combination, or a time sequence of such conditions occurring such as the output of a first analysis tool exceeding a first threshold followed within one second by the output of a second analysis tool exceeding a second threshold.

In some embodiments, the detection subsystem 326 is configured to analyze the acquired physiological data by determining a quantity or a quality of periodic variation with which the acquired physiological data is characterized. This quantity or quality of periodic variation may comprise one or more of an ultradian, circadian, or circalunar variation. The quantity or quality of periodic variation may be identified as a characteristic of physiological data subjected to a line length tool (e.g., identified based on the variation of line length of an electrographic signal averaged over time or a count of pathological events). Determining the quantity or quality of the periodic variation may involve one or more of the following analytic approaches: (1) determining a frequency or period of the periodic variation; (2) determining a modulation depth of the periodic variation; (3) determining an autocorrelation of a physiological measurement (e.g., wherein successive values of the physiological measurement are correlated with each other and the degree of correlation is quantified in some manner relative to the successive values); (4) determining a correlation or a coherence between multiple physiological measurements; (5) determining a phase of a periodic variation with respect to a phase of a different physiological measurement; and (6) determining a phase of a periodic variation with respect to a time interval such as calendar days, 28-day intervals, a patient's sleep cycle, a patient's medication schedule, or a patient's menstrual cycle. The quantity or quality of periodic variation with which the acquired physiological data is characterized may be useful, for example, in assessing whether a stimulation parameter set is effective for a patient. For example, the effectiveness of a stimulation parameter set may be estimated to be inversely proportional to the autocorrelation of the count of events at a 28-day time difference.

FIG. 5 is an illustration of the therapy subsystem 328. Inputs to the therapy subsystem 328 are shown on the right, and outputs are on the left. Referring initially to the input side, the therapy subsystem 328 includes a control interface 510, which receives commands, data, and other information from the CPU 340, the memory subsystem 338, and the detection subsystem 326. The control interface 510 uses the received commands, data, and other information to control a therapeutic stimulator 512, a sensory stimulator 514, and a diagnostic stimulator 516. The therapeutic stimulator 512 is adapted to provide electrical stimulation signals appropriate for application to neurological tissue to terminate a present or predicted undesired neurological event, especially an epileptic seizure or its precursor.

The therapeutic stimulator 512 is typically activated in response to conditions detected by the sensing subsystem 522, but as noted above, may also provide some substantially continuous or scheduled stimulation ("programmed stimulation"). The sensory stimulator 514 is also typically activated in response to a detection by the sensing subsystem. It may electrically stimulate enervated tissue, such as the scalp, to provide a tactile sensation to the patient, or may alternatively include an audio or visual transducer to provide audiovisual cues, such as warnings, to the patient.

Some embodiments of the neurostimulator 110 may include a diagnostic stimulator 516, which can be used to perform active electrophysiological diagnostic measurements. The diagnostic stimulator 516 may include an excitability stimulator 518 and a refractoriness stimulator 520, with may be implemented with the same or different circuit under appropriate controls from the control interface 510. The excitability stimulator 518 and the refractoriness stimulator 520 both act under the control of the detection subsystem 326 to provide the stimulation signals used for the effective measurement of electrophysiological parameters in some embodiments. The excitability stimulator 518 may provide pulses at varying current levels to test the excitability of neural tissue, while the refractoriness stimulator 520 provides pairs of pulses with varying inter-pulse intervals to test the inhibitory characteristics of neural tissue.

The therapy subsystem 328 also may include a drug dispenser controller 522, which under the control of the control interface 510, is adapted to selectively allow the release of a drug or other therapeutic agent from a drug dispenser 336 to one or more desired sites, within or near the patient's brain or elsewhere in the body. As is the case with therapeutic stimulation, drug therapy can be performed in response to a detected neurological event or condition, on a substantially continuous basis or scheduled ("programmed drug therapy").

The therapeutic stimulator 512, the sensory stimulator 514, and the diagnostic stimulator 516 are all coupled to a multiplexer 524, which is controllable to select the appropriate types of therapy, for example, an instance of stimulation defined in accordance with a stimulation parameter set to be generated by the stimulation signal generator 526. The multiplexer 524 may allow only one type of therapy to be performed at a time, but in some embodiments, the multiplexer 524 allows different types of therapy, such as two instances of stimulation defined in accordance with two different stimulation parameter sets, to be selectively applied to the different electrodes 312-318, either sequentially or substantially simultaneously. The stimulation signal generator 526 receives commands and data from the therapeutic stimulator 512, the sensory stimulator 514, and the diagnostic stimulator 516, and generates electrical stimulation signals having the desired characteristics that are properly time-correlated and associated with the correct electrodes, and receives power from a controllable voltage multiplier 528 to facilitate the application of a proper voltage and current to the desired neural tissue. The voltage multiplier 528 is capable of creating relatively high voltages from a battery power source, which typically has a very low voltage. The stimulation signal generator 526 has a plurality of outputs, which in the disclosed embodiment are coupled to the electrode interface 320. The stimulation signal generator 526 can perform signal isolation, multiplexing, and queuing functions if the electrode interface 320 does not perform such functions.

The neurostimulator 110 is configurable to store information in the memory subsystem 338. The information may relate to sensed physiological data (e.g., waveforms or filtered or processed waveforms), store information relating to one or more conditions of the neurostimulator 110 at the time the sensed information is acquired (e.g., a date/time stamp, whether an amplifier in a sensing channel of the neurostimulator is saturated and, if so, for how long, the stimulation etc.), or store information relating to the form of stimulation delivered to the patient, if any (e.g., information with which a delivered instance of stimulation (e.g., a stimulation waveform) may be identified or recognized, information corresponding to whether a desired amplitude of stimulation was achieved, etc.).

Information storing may be undertaken as part of one or more of a recording function or event counting or event logging function of the control module 310. For example, if the neurostimulator 110 is configured to identify as a neurological event a characteristic in the monitored electrographic activity it acquires, e.g., as a seizure onset neurological event type), then a function of the neurostimulator 110 may be to keep track of how many times it detects that neurological event over a fixed period of time (e.g., 24-hours) or a variable period of time (e.g., during a time when the patient is experiencing symptoms associated with the neurological disorder for which the patient is being treated). Another function of the neurostimulator 110 may be to store the sample of acquired physiological data in which each neurological event was detected (or a digitized or otherwise processed), so that, for instance, a physician may later review the sample by interrogating the information stored on the implant. If the physiological data includes ECoGs sensed by measuring field potential changes at one or more sensing locations in the patient's brain, then what the neurostimulator 110 records may comprise ECoG records. The running count of the number of detected events may be stored in an event counting/logging module of the memory subsystem 338 and the ECoG may be recorded in a recording module of the memory subsystem 424.

The responsive stimulation capability of the neurostimulation system will now be further described with reference to FIG. 6. Electrographic activity 610 (or ECoG 610) evidences a signal portion 612 which, according to a detection parameter set of the neurostimulator, corresponds to rhythmic activity, which in turn corresponds to a particular neurological event type, namely, a seizure onset. The neurostimulator detects the seizure onset, and responds with an instance of stimulation therapy 628, generated in accordance with a stimulation parameter set. The exploded view of the ECoG 610 at the signal portion 614 shows the timing of delivery of the instance of stimulation therapy, relative to the occurrence of the rhythmic activity to the neurostimulator is configured to detect and respond to. The specific characteristics of the waveform 610 are exemplary only and for purposes of illustration. More particularly, in the ECoG 610, a small segment 614 of the seizure portion 612 is magnified and shown as a magnified segment 616. The magnified segment 616 is used to illustrate how the neurostimulator might extract, according to a detection parameter set, features of interest in the electrographic activity. An increasing half wave 618 represents a substantially monotonic (exclusive of a small hysteresis allowance) increasing portion of the magnified segment 616 between a local minimum 620 and a local maximum 622 of the waveform 610. The amplitude difference (on the Y axis) between the local minimum 620 and the local maximum 622 is the amplitude 624 of the half wave, and the time difference (on the X axis) between the local minimum 620 and the local maximum 622 is the duration 626 of the half wave. If the amplitude 624 and duration 626 exceed respective thresholds, then the observed half wave is considered a "qualified half wave," and is generally regarded as representative of the dominant frequency and amplitude of the electrographic waveform. If the observed half wave does not meet the thresholds, it is disregarded. It should be noted that even if a qualified half wave meets minimum amplitude and duration thresholds, it is not necessarily truly representative of the underlying signal's frequency or wavelength; it is only a single measurement from what is likely a complex waveform.

A biphasic stimulation pulse 628 may be applied after a time delay 630 equal in length to the duration 626, thereby approximately synchronizing the pulse 628 to an expected trough 632 in the waveform 610. It should be recognized, of course, that the duration of a qualified half wave is not necessarily accurately representative of the wavelength of the electrographic waveform 610 in the seizure portion 612 (because of variations in the waveform 610 and in the individual half waves making up the waveform 610), so in practice it is unlikely that the pulse 628 will be accurately synchronized to the trough 632. However, after a delay of only one additional half wave duration 626, it is expected that the pulse 628 and the trough 632 may be relatively close.

After a delay of multiple half wave durations, or after significant processing latency, synchronization is less likely and decorrelation will generally be the primary outcome. Accordingly, if the time delay 630 is set to be a multiple (or some other mathematical transform) of the duration 626, or if there is a significant amount of latency between measurement of half wave amplitude 624 and duration 626 and when a stimulation pulse 628 is applied, the delay 630 will generally desynchronize stimulation from the waveform 610 as a result of accumulated error and changes in the characteristics of the waveform 610.

It should be noted that while a single biphasic pulse is illustrated in FIG. 6, that pulse is not necessarily to scale and is intended only to illustrate an exemplary timing relationship between the magnified segment 616 and the start of the pulse 628. The amplitude of the pulse 628 may not have the illustrated relationship to the waveform 610. And in an alternative embodiment, the pulse 628 may have a waveform other than a short biphasic pulse, or may be the first portion of a regular or irregular burst of pulses or other signals.

The Mapping Function Module

The mapping function module allows the neurostimulator to determine the stimulation parameter set with which to generate an instance of stimulation therapy based on which type of neurological event the neurostimulator detected. More specifically, the mapping function module first narrows the range of possible values for each parameter in a stimulation parameter set from the entire stimulation parameter space to a stimulation parameter subspace, and then it selects a discrete value for each parameter to result in a default stimulation parameter set. The mapping function module may choose both the stimulation parameter subspace and the default stimulation parameter set based on the type of neurological event the neurostimulator has detected. In the examples described here, the neurological event is a seizure onset and the types of the seizure onsets are human-defined.

In a simple implementation, the mapping function module is implemented as a look up table, such that when the neurostimulator detects a neurological event and categorizes or classifies it as a particular neurological event type, such as a hypersynchronous seizure onset, the look up table delivers the stimulation parameter subspace and the default stimulation parameter set based on that categorization or classification. Table 1 below is an example of such a look up table that might be used in a mapping function module according to embodiments.

TABLE 1

| Onset Type | Therapy Type | Stimulation parameter subspaces and default stimulation parameter sets |
|---|---|---|
| Low Voltage Fast | High Frequency Stimulation (≥100 Hz) | Subspace: biphasic, 2.5-4 mA pulse amplitude (PA), 80-120 Hz frequency (inverse of IPI), 450-600 μs pulse width (PW), 250-500 ms burst duration (BD) Default: biphasic, 3 mA PA, 100 Hz, 500 μs PW, 400 ms BD |
| High Voltage Beta | Very high Frequency Stimulation (≥200 Hz) | Subspace: biphasic, 0.5-1 mA PA, 180-333 Hz, 70-110 μs PW, 80-250 ms BD Default: biphasic, 0.8 mA PA, 200 Hz, 100 μs PW, 200 ms BD |
| Hypersynchronous | Intermittent burst stimulation including theta burst stimulation (~7 Hz)/ Desynchronizing Stimulation | For Intermittent burst stimulation including Theta Burst Stimulation: Subspace: biphasic, 0.8-1.5 mA PA, 500 Hz, 200 μs PW; 3 seconds BD and an interburst interval (IBI) of 142 ms Default: biphasic, 1.2 mA PA, 500 Hz, 200 μs PW, 3 seconds BD and 142 ms IBI For Desynchronizing Stimulation: Subspace: biphasic, 0.8-1.5 mA PA,, 100-150 Hz, 75-150 μs PW, 0.5-2 S BD, random electrode selection, 3 cycles on, 2 cycles off and an IBI of 100-160 ms Default: 1 mA PA,, 130 Hz , 100 μs PW, 1 second BD and 130 ms |
| Spike and Wave | Theta Stimulation (≥7 Hz) | Subspace: biphasic, 0.3-1 mA PA, 6-10 Hz, 40-150 μs PW, 0.3-1 minute BD Default: biphasic, 0.5 mA PA, 7 Hz, 100 μs PW, 0.5 minutes BD |
| Multiple | Voltage Controlled Low Frequency Stimulation (1 Hz, square wave, 1 minute duration) | Subspace: biphasic, square wave, ±(0.5-1.0 V) PA, 0.5-1.5 Hz, 700-1200 μs PW, 0.75-1.5 minutes BD Default: biphasic, ±1 V PA, 1 Hz, 1,000 μs PW, 1 minute BD |

TABLE 1-continued

| Onset Type | Therapy Type | Stimulation parameter subspaces and default stimulation parameter sets |
|---|---|---|
| Attenuation | High Amplitude and/or Trigger External Device Alerting Stimulation, High amplitude stimulation is defined as: a stimulation of sufficient amplitude to cause a sensation, e.g. visual or auditory, for the patient. | Default: High Amplitude: 12 mA PA, 200 Hz, 100 µs PW, 5 seconds BD Default: Alerting stimulation: Stimulation delivered to brainstem nuclei e.g. serotonergic nuclei in order to increase serotonergic tone. 1-3 mA PA, 200 Hz, 160 µs PW, 100 ms BD Default trigger for external device: Trigger sent wirelessly to external device |

Notes on Table 1

An alerting stimulation is defined as consisting of stimulation delivered to parts of the brain associated with arousal and/or a trigger that is used to activate an external device that alerts a caregiver to arouse the patient.

One form of desynchronizing stimulation called Coordinated Reset (CR) was initially proposed by "Coordinated reset has sustained aftereffects in Parkinsonian monkeys," Tass, P. A., Qin, L., Hauptmann, C., Dovero, S., Bezard, E., Boraud, T., and Meissner, W. G. Ann. Neurol, 72:816-820 (2012) and "Optimal number of stimulation contacts for coordinated reset neuromodulation," Lysyansky, B., Popovych, O. V., and Tass, P. A. Front Neuroeng., 6:5 (2013). It has been demonstrated that this type of stimulation shifts a network from a synchronized state with strong coupling to a desynchronized state with weak coupling. It is generally defined as three CR cycles, each comprising a randomized sequence of three high frequency pulse trains, followed by two silent cycles. That pattern is repeated periodically. The random variation of the high frequency pulse train sequences and the 3:2 ON-OFF pattern, as described in "Coordinated reset has sustained aftereffects in Parkinsonian monkeys," Tass, P. A., Qin, L., Hauptmann, C., Dovero, S., Bezard, E., Boraud, T., and Meissner, W. G. Ann. Neurol, 72:816-820 (2012), optimize the desynchronizing CR effect. Given the ability of CR stimulation to desynchronize networks it may represent an ideal stimulation parameter subspace to treat hypersynchronous onsets.

Intermittent burst stimulation, including theta burst. Intermittent burst stimulation involves providing bursts of high frequency stimulation at specific interburst frequencies. For instance, theta burst stimulation involves applying short trains of stimuli at high frequency where the bursts are repeated at frequencies within the theta range. This may represent an alternative stimulation approach for subjects that haven't responded to other stimulation paradigms and in the example is an alternative for subjects with hypersynchronous electrographic seizure onsets.

The presence of theta activity in the hippocampus ECoG has been associated with a reduction in the frequency of hippocampal epileptic discharges in some animal models of mesial temporal lobe epilepsy. See e.g., "Septal networks: relevance to theta rhythm, epilepsy and Alzheimer's disease," Colom, L. V. J Neurochem., 96:609-623 (2006). This has been demonstrated for spontaneously occurring theta activity as well as electrically or chemically induced theta activity. See e.g., "Anticonvulsant effects of the experimental induction of hippocampal theta activity," Miller, J. W., Turner, G. M., and Gray, B. C. Epilepsy Res., 18:195-204 (1994); and "Septal networks: relevance to theta rhythm, epilepsy and Alzheimer's disease," Colom, L. V. J Neurochem., 96:609-623 (2006). In addition, epileptic seizures have been demonstrated to occur less frequently during: 1) active wakefulness or rapid eye movement (REM) sleep (see e.g., "Sleep influence on seizures and epilepsy effects on sleep in partial frontal and temporal lobe epilepsies," Crespel, A., Coubes, P., and Baldy-Moulinier, M. Clin. Neurophysiol., 111 Suppl 2:S54-S59 (2000); "Distribution of partial seizures during the sleep-wake cycle: differences by seizure onset site," Herman, S. T., Walczak, T. S., and Bazil, C. W. Neurology, 56:1453-1459 (2001); "Relationship of epileptic seizures to sleep stage and sleep depth," Minecan, D., Natarajan, A., Marzec, M., and Malow, B. Sleep, 25:899-904 (2002); "The interaction between sleep and epilepsy," Malow, B. A. Epilepsia, 48 Suppl 9:36-38 (2007); and "Why are seizures rare in rapid eye movement sleep? Review of the frequency of seizures in different sleep stages," Ng, M. and Pavlova, M. Epilepsy Res. Treat., 2013:932790 (2013)), 2) states that are coincident with hippocampal theta activity in animals (see e.g., "A circadian rhythm of hippocampal theta activity in the mouse," Welsh, D. K., Richardson, G. S., and Dement, W. C. Physiol. Behav, 35:533-538 (1985)) and in humans (see e.g., "Sleep-dependent theta oscillations in the human hippocampus and neocortex," Cantero, J. L., Atienza, M., Stickgold, R., Kahana, M. J., Madsen, J. R., and Kocsis, B. J Neurosci, 23:10897-10903 (2003)). Given the ability of the theta activity, spontaneous or induced, to prevent epileptic seizures, delivering theta stimulation may be beneficial to epilepsy patients who have not responded to other neurostimulation paradigms. In the example stimulation parameter subspace mapping of Table 1, this type of stimulation has been mapped to subjects with electrographic seizure onsets characterized by spike and wave activity.

Voltage controlled low frequency stimulation (VCLFS) is distinct from other stimulation approaches in that the duration of each phase of an individual pulse is hundreds of milliseconds compared to the short microsecond phases typically delivered by neurostimulation systems. This type of stimulation has been shown to decrease the duration and incidence of after discharges and stage 5 seizures during kindling acquisition and to decrease the incidence of stage 5 seizures in fully kindled animals when delivered prior to the kindling stimulus. See e.g., "Preemptive low-frequency stimulation decreases the incidence of amygdala-kindled seizures," Goodman, J. H., Berger, R. E., and Tcheng, T. K. Epilepsia, 46:1-7 (2005). It has also been shown to reduce the incidence of stage 5 seizures in fully kindled rats when delivered post-ictally. See e.g., "Effect of focal low-frequency stimulation on amygdala-kindled after discharge thresholds and seizure profiles in fast- and slow-kindling rat strains," Carrington, C. A., Gilby, K. L., and McIntyre, D. C.

Epilepsia, 48:1604-1613 (2007), demonstrated that this type of stimulation increased the after discharge thresholds in rats. Moreover, VCLFS has shown to be effective in animal models of spontaneous seizures. In the example table this stimulation subspace has been mapped, by the supervised machine learning process, to onsets that contain multiple patterns e.g. delta brush activity that is characterized by high frequency gamma riding on slow delta frequency activity.

The information included in a look up table such as that of Table 1 may be derived from a database including ECoG files (each comprised of ECoG records corresponding to each channel on which the electrographic activity was recorded) from one or more patients and the history of stimulation parameter sets used with the same patient(s) and their clinical effectiveness.

Processes for creating the mapping function will now be summarized and then described in more detail.

Summary of Processes for Creating a Mapping Function

A mapping function may be developed based on a clinical data collected across a patient population, as during a clinical trial for a responsive neurostimulation system. Features are extracted from the collected ECoGs and are processed to identify different neurological event types, more specifically in the case of the embodiments described in detail here, seizure onset types. The clinical data may be further processed to identify, for each of the different seizure onset types, a stimulation parameter subspace with demonstrated effectiveness in treating the neurological condition associated with the seizure onset type. It will be appreciated, however, that a mapping function can be created for virtually any neurological event type defined by features extracted from electrographic activity, including but not limited to neurological events types comprising spiking or interictal (between seizures) neurological events.

ECoG records evidencing the earliest onsets are further processed to create groups from across patients having similar types of seizure onsets, e.g., groups of ECoG records with hypersynchronous seizure onset types, low voltage fast seizure onset types, etc. A few to several features such as amplitude of the signal in the ECoG record, frequency of the signal in the ECoG record, may be extracted from the ECoG records and supervised machine learning and/or clustering techniques may be used on the extracted features for grouping ECoG records having similar types of neurological events, e.g., similar types of electrographic seizure onsets. In the supervised machine learning technique, human experts identify the electrographic seizure onset type in a fraction of the ECoG records with earliest electrographic seizure onsets. This information is used to train the supervised machine learning technique using well-established methods that have been extensively published. See e.g., "Automated seizure onset detection for accurate onset time determination in intracranial EEG," Chan, A. M., Sun, F. T., Boto, E. H., and Wingeier, B. M. Clin. Neurophysiol., 119:2687-2696 (2008); "Forecasting Seizures Using Intracranial EEG Measures and SVM in Naturally Occurring Canine Epilepsy," Brinkmann, B. H., Patterson, E. E., Vite, C., Vasoli, V. M., Crepeau, D., Stead, M., Howbert, J. J., Cherkassky, V., Wagenaar, J. B., Litt, B., and Worrell, G. A. PLoS. One., 10:e0133900 (2015)]. In the clustering approach, an external component of the neurostimulation system may cluster ECoGs records into groups based on similarity between the extracted features. A principal difference between the two techniques is that, in the supervised machine learning technique, the groups of ECoG may be formed based on the human-defined seizure onset types (such as hypersynchronous, low voltage fast seizure onset types, etc.), whereas in the clustering technique, the groups of ECoG records may not line up with a given human-defined seizure onset types since they will have been established by a machine. One or both these techniques will be used to group the ECoG records into different types of seizure onsets.

Once groups of seizure onset types have been established, the clinical data (which may include metrics such as patient-reported disease-burden measures including clinical seizure rate) are processed to identify, for each of seizure onset type, a stimulation parameter subspace that has been shown to be effective in treating the neurological condition associated with the seizure onset type. For example, when the patient's reported rate of clinical seizures reduces by 50% or more (i.e., a ≥50% reduction in clinical seizures, a stimulation parameter subspace may be deemed effective for that patient). For this example, dominant seizure onset types will be identified in each patient. These dominant seizure onset types either will be the human-defined seizure onsets types or the machine-determined seizure onset types that occur most commonly in the patient. Then, stimulation parameter sets that are effective in reducing the disease burden will be identified in each of these patients. The effective stimulation parameter sets will be grouped by each of the seizure onset types to form stimulation parameter subspaces. Thus a mapping function between seizure onset types and stimulation parameter subspaces will be created.

One method for developing a mapping function will now be described in greater detail with reference to FIGS. 7A and 7B, FIGS. 8A-8F, and FIG. 10-15. The method may be performed by one or more processors configured to execute the steps in the methods. The one or more processors may include an external device, such as a programmer 212, 228, 230, 232 (FIG. 2), having executable code defining one or more algorithms configured to implement the steps of the method. The mapping function may be derived from numerous electrographic signals (ECoGs) obtained over time and from across a patient population.

A classification process may be used to create the mapping function. The classification process may be created using a supervised machine learning process 707 or a clustering process 709. The supervised machine learning process 707 and the clustering process 709 depend on common prerequisite processes, including the identification and selection of ECoG files having a seizure onset 702, 704; and identification of, and feature extraction from, earliest onset channels of the selected ECoG files 706, 708.

1. Analyze to Identify ECoG Files that Include a Particular Neurological Event and Types of the Event (e.g., Seizure Onset and Seizure Onset Types)

Figure 7A:
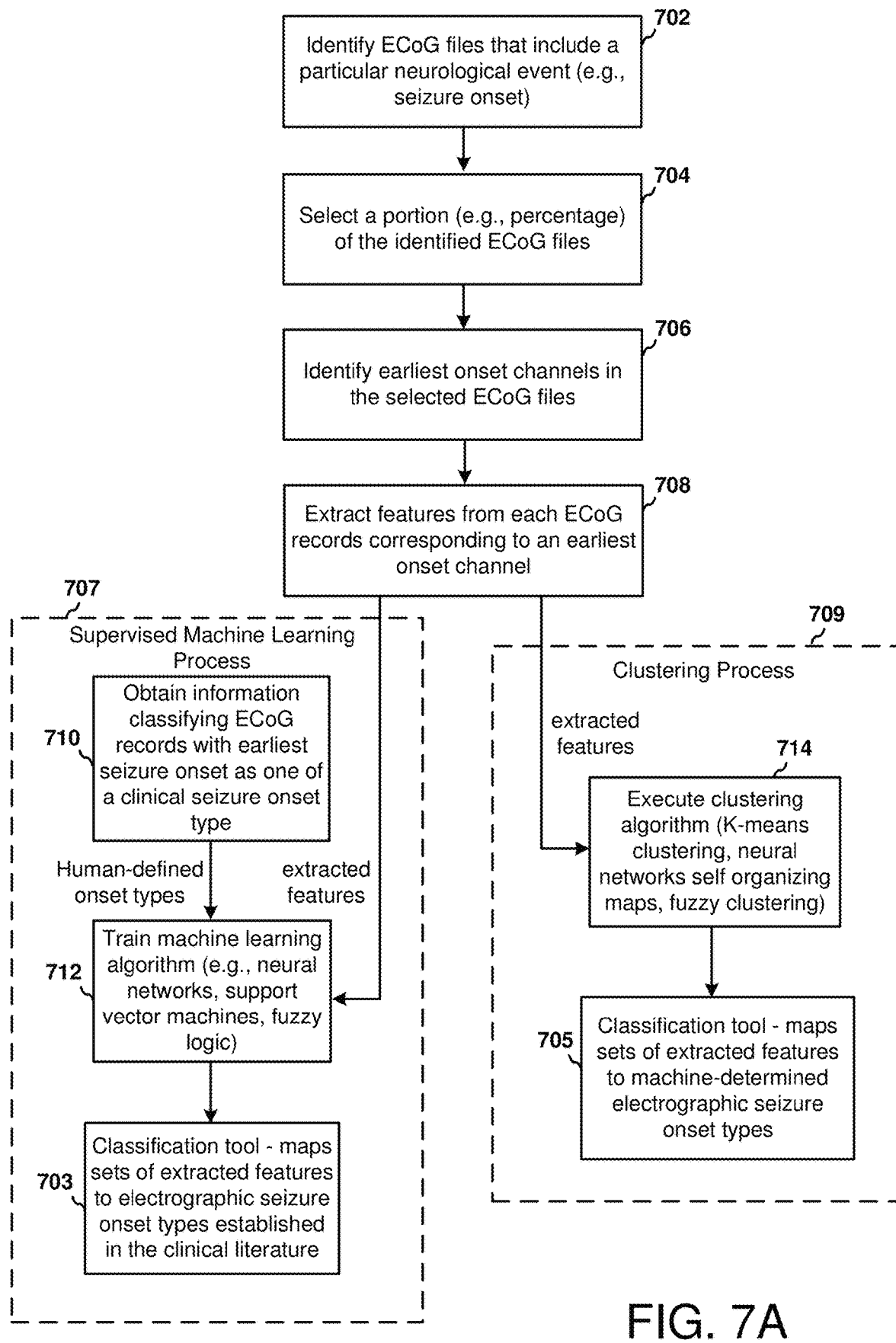
FIG. 7A and FIG. 7B are flowcharts of a method of creating a mapping function between neurological events and stimulation parameters.

Referring now to FIG. 7A at 702, ECoG files comprised of ECoG records (for each channel represented in the file) are analyzed to determine the likelihood that the ECoG file contains a seizure onset. If so, the ECoG records are analyzed to identify on which channel or channels the seizure onset is evidenced first (in time). Referring again to FIG. 8A, the recorded electrographic activity representing the ECoG file 802a is comprised of the ECoG records 804a, 806a, 808a, and 810a for the four sensing channels (Channels 1-4). This ECoG file evidences a hypersynchronous seizure onset type, but it occurs only in the ECoG record 804a for Channel 1. Referring to FIG. 8D, the low voltage fast seizure onset occurs in the recorded electrographic activity representing the ECoG file 802d, but this time the neurological event occurs in two of the ECoG records, namely the ECoG record 804d for Channel 1 and the ECoG record 806d for Channel 2. The low voltage fast seizure onset occurs first (in time) on both Channel 1 (corresponding to ECoG record 804d) and Channel 2 (corresponding to ECoG record 806d).

The tools used to analyze the ECoG files can be the same as those used to detect neurological events implemented in the neurostimulator (i.e., in the embodiments described above, the half-wave, line length, and area tools for determining the power of the ECoG in various frequency bands, the variability of the ECoG, and the energy of the ECoG, respectively). Alternatively, and especially if the analysis is accomplished by components for which computational complexity or power is not a limiting factor, the ECoG files can be analyzed more robustly to identify the seizure onset types of interest. Table 2 includes half-wave, line length, and area along with many other features that might be extracted in an analysis of ECoG files and their associated ECoG records, some in the time domain and others in the frequency domain (e.g., Fourier transform, discrete wavelet transform).

TABLE 2

| Category | Feature |
| --- | --- |
| Time domain | Line length |
| | Variance |
| | Area under the curve |
| | Energy/power |
| | Fractal dimension |
| | Kurtosis |
| | Number of peaks |
| | Maximum |
| | Mean |
| | Minimum |
| | Non-linear energy |
| | Coefficient of variation |
| | Shannon entropy |
| | Skewness |
| | Total maxima and minima |
| | Cross-frequency coupling |
| | Variance/standard deviation |
| | Zero crossings |
| | Zero crossings of first derivative |
| | Omega complexity |
| | The brain symmetry index |
| | Spike rhythmicity |
| | Phase synchronization |
| | Cross-correlation between different channels |
| Discrete Wavelet transform | Bounded variation |
| | Coefficients |
| | Energy |
| | Entropy |
| | Relative bounded variation |
| | Relative power |
| | Relative scale energy |
| | Variance/standard deviation |
| | Maximum/Minimum of wavelet coefficients |
| | Mean/Standard deviation of the wavelet coefficients |
| Continuous Wavelet transform | Coefficient z-score |
| | Energy |
| | Entropy |
| | Standard deviation of energy |
| Fourier transform | Median frequency |
| | Peak frequency |
| | Spectral edge frequency |
| | Spectral entropy |
| | Total spectral power |

TABLE 2-continued

| Category | Feature |
| --- | --- |
| | Temporal evolution of spectral energy |
| | Energy in specific frequency bands |
| | Ratio of energy in specific frequency bands |

The following notes further describe some of the elements in Table 2:

Phase synchronization: During epileptic seizure activity, phase synchronization of electrographic activity recorded on different electrodes on a multi-contact electrode implanted in an epileptic brain may change. Phase correlation values may be different in the different types of seizure onsets and may be a useful measure for classifying seizure onset types.

Mean amplitude: Electrographic seizure activity is often accompanied by increased amplitude in the ECoGs. However, during the seizure onset, there may be increase/decrease or no change in seizures activity. For example, in low voltage fast seizure onset types, the amplitude may be less than baseline whereas with high voltage beta type of onset the amplitude is usually higher than baseline.

Minimums and maximums: The total number of local maxima and minima in the ECoGs has been shown to indicate epileptic activity. During the seizure onset, depending on the type of onset, this feature may increase or decrease from the baseline number of total maxima and minima.

Zero crossings: The total number of zero crossings may change during seizure activity. Since this feature strongly correlates with the frequency of the signal, this may be a useful feature to classify the different types of onsets. For example, there may be many more zero crossings in the low voltage fast seizure onset type compared to the number of zero crossing in the hypersynchronous onset type.

Omega complexity: According to "Detecting temporal lobe seizures from scalp EEG recordings: a comparison of various features," van Putten, M. J., Kind, T., Visser, F., and Lagerburg, V. Clin. Neurophysiol., 116:2480-2489 (2005) and "Beyond mapping: estimating complexity of multichannel EEG recordings," Wackermann, J. Acta Neurobiol. Exp. (Wars.), 56:197-208 (1996), this measure can be considered as the number of linearly independent generators needed to 'explain' the data. This measure may vary for the different type of seizure onsets.

Some additional features may be computed that combine time and frequency domain functions. One example is to first band pass filter the signal (time domain), then compute the spectrogram of the signal (frequency domain), compute the mean/median along all frequencies at every time point (time domain) from the spectrogram, low pass filter the resulting signal for purposes of smoothing (time domain) and finally find peaks in the resulting signal (time domain).

Depending on the number of extracted features, a dimensionality reduction algorithm such as principal component analysis or a feature subset selection algorithm such as Lasso or support vector machine recursive feature elimination (SVM-RFE) may be implemented to reduce redundancy in the extracted features. The number of resulting new features may be less than the total number of extracted features, thereby making data analysis more manageable and more precise.

It should be understood, that although not detailed in connection with embodiments described herein, that other stimulation parameters in the parameter space may be used to define an instance of stimulation therapy delivered by a neurostimulator. For example, the identification of which electrode(s) are used to deliver the instance of stimulation therapy may comprise a stimulation parameter. Similarly, the polarity assigned to an electrode through which the instance of stimulation is delivered may be another parameter in the stimulation parameter space/subspace. Thus in some embodiments, these parameters may be included in the map of effective stimulation parameters to seizure onset types as identified by the mapping function (e.g., as created using a supervised machine learning approach or a clustering approach).

Generally, ECoG files are processed to identify signals that contain a particular neurological event, such as a seizure onset at step 702. The origin of the ECoGs files to be processed by the external device 212, 228, 230, 232 may be an implantable neurostimulator 110, such as is described above with reference to FIG. 1B through FIG. 6, that is configured to sense ECoGs and to process the ECoGs to detect the neurological event, for example, based on one or more of a half-wave, line length, or area analysis tools. The analysis tools resident in and used by the neurostimulator 110 may be referred to as "online processes." The neurostimulator 110 may also be configured to store those ECoGs corresponding to a detected neurological event as ECoG files in a memory subsystem 338. An ECoG file stored by the neurostimulator may include a separate ECoG record for each of a number of sensing channels defined by a pair of electrodes 312, 314, 316, 318. The neurostimulator 110 may be further configured to upload the stored ECoG files to a central database 222 (FIG. 2). As used herein an ECoG of an individual sensing channel may be referred to either as an "ECoG record" or a "channel ECoG."

The ECoG files stored in the database 222 may be obtained by a programmer 212, 228, 230, 232 and processed by a module resident in the external device and configured to detect the same neurological events detected by the neurostimulator 110. Processes or modules resident in the external device 212, 228, 230, 232 may be referred to as "offline processes." At 702, the offline processes evaluate the ECoG files to identify those ECoG files containing the neurological event, e.g., a seizure onset. A seizure onset may be detected in the ECoGs by the programmer using the same analysis tools, e.g., half wave, line length, area, that are used by an implanted neurostimulator to detect the neurological event. However, because an external component of the neurostimulation system can be configured with more computing power than an implanted component, the offline analysis tools used by the external component to detect a seizure onset may be more sophisticated and computationally intensive than any provided in the neurostimulator 110. Algorithms other than the foregoing analysis tools may be used by the external device to detect seizure onsets. For example, algorithms described in "Automated seizure onset detection for accurate onset time determination in intracranial EEG," Chan, A. M., Sun, F. T., Boto, E. H., and Wingeier, B. M. Clin. Neurophysiol., 119:2687-2696 (2008) may be used.

2. Select a Portion (e.g., a Percentage) of the ECoG Files/Records Identified Returning to FIG. 7A, a portion or subset of those ECoG files identified in step 702 as containing the neurological event are selected for further processing by the external device (704). The selected portion may be a percentage of the total number of identified ECoG files. The percentage may range between 0% and 100%. For example, in implementations of the supervised machine learning process 707 the selected portion may be a random 20% of all of the ECoG files whereas using the clustering process 709 the selected portion may be 80%. The selected portion of ECoGs are further processed in 706 and 708, as described below, and subjected to the supervised machine learning process 707. For the clustering process, all identified ECoG files are further processed in 706 and 708, as described below, and subjected to the clustering process 709.

3. Identify the Earliest Onset Channels in the Selected Portion of ECoG Files/Records Each of the selected ECoG files is further processed by the external device to identify the earliest onset channel within the ECoG file (706). As previously mentioned, an ECoG file may include a separate ECoG record for each of a number of sensing channels defined by a pair of electrodes 312, 314, 316, 318. Here, each ECoG record for each sensing channel of a selected ECoG record is processed by the external device to determine if the ECoG record for that sensing channel includes a seizure onset. For those ECoG records having a seizure onset, the method determines the time at which the seizure onset occurs and then the channel(s) on which it occurred.

More specifically, the time of seizure onset for each channel may be determined using the same analysis tools and algorithms used to detect a seizure onset, as described above. Once the time of seizure onset for each channel is determined, the external device compares the respective times to determine the channel having the earliest seizure onset. The identified channel having the earliest occurrence of the seizure onset is referred to as the "earliest seizure onset channel." In some cases, the external device may detect a seizure onset in only one channel of an ECoG record. In such cases, the channel having the seizure onset is considered the earliest seizure onset channel.

In cases where more than one channel evidences a seizure onset that occurs at or about the same time, each such channel is identified as an earliest seizure onset channel. With reference to FIGS. 8A, 8B, and 8C only a single channel (Channel 1) is identified as having the earliest seizure onset. With reference to FIG. 8D, two channels (Channel 1 and Channel 2) are identified as having a seizure onset. In this case, the time of occurrence of each of the seizure onsets would be compared to identify the earliest seizure onset channel. In FIG. 8D, Channel 1 and Channel 2 have similar seizure onset times, and therefore both of Channel 1 and Channel 2 are identified as earliest seizure onset channels.

4. Extract Features From Each ECoG Record Corresponding to an Earliest Onset Channel The ECoG records corresponding to each of the identified earliest seizure onset channels are processed by the external device to extract features (708). With reference to example process illustrated in FIG. 10 and FIG. 11, these extracted features may include, for example, the number of peaks, dominant frequency, mean amplitude at onset, line length, and energy in beta band/energy in theta band. Any of the many additional features listed in Table 2 may also be extracted and processed by the external device.

5. Apply Either a Supervised Machine Learning Process or a Clustering Process to Classify ECoGs into Seizure Onset Types

A. Supervised Machine Learning Process

In a supervised machine learning process (707), the external device obtains information that classifies each of the ECoG records of an identified earliest seizure onset channel as one of several seizure onset types (710). For example, the seizure onset types may be one of the human-defined seizure onset types described above with reference to FIGS. 8A-8F, such as the hypersynchronous, high voltage beta, multiple, low voltage fast, attenuation or spike and wave seizure onset types. The information that classifies the ECoG may be based on subjective observation by humans through visual analysis of the earliest seizure onset channel waveforms. In this case, the seizure onset types may be referred to as "human-defined seizure onset types." The ECoG classification information may be stored in the database 222 and subsequently obtained by the external device.

At step 712, the supervised machine learning process is trained to map sets of the features extracted from the ECoG records at 708 to the human-defined seizure onset types determined at step 710. By way of example not limitation, the supervised machine learning process may comprise any of a neural networks, a support vector machines, a fuzzy logic algorithm.

Inputs to the supervised machine learning process are the features extracted in step 708 and the seizure onset types obtained in step 710. The trained version of the supervised machine learning process resulting from step 712 is a classification process 703 that is configured to classify other extracted feature sets into one of a number (N) of human-defined seizure onset types. The classification process is also configured to provide a measure of probability that an extracted feature set represents a human-defined seizure onset type. Further on this point, a measure of probability for an extracted feature set may be provided for more than one seizure onset type, with the total sum of probabilities being 1. The accuracy of the classification process in matching extracted features sets to a particular seizure onset type depends on the quantity of inputs provided to the supervised machine learning process in step 712, with an increased number of training inputs resulting in an increased level of accuracy. In one configuration, sufficient training inputs are provided to the supervised machine learning process to provide a classification process having a minimum classification accuracy of around 80% on ECoG records with seizure onsets that were not used for training the supervised machine learning process.

Figure 10:
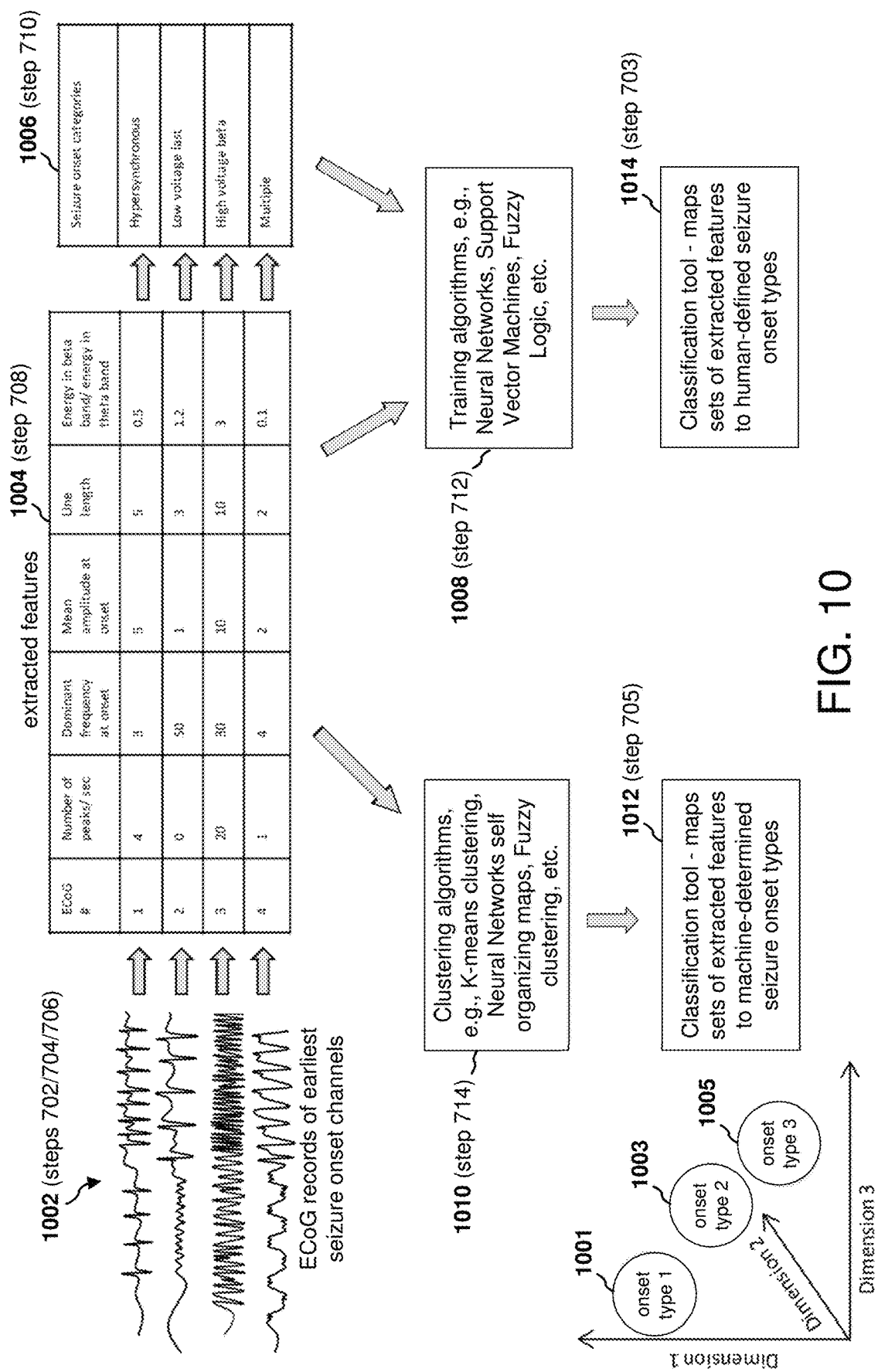

FIG. 10 further illustrates the method of FIG. 7A, especially steps 702, 704, 706, 708, and 710 of the method of FIG. 7A. The four waveforms 1002 represent a sample of ECoG records corresponding to earliest seizure onset channels as determined in steps 702, 704 and 706. The first table 1004 includes the values of features extracted from each ECoG record with the earliest onsets 1002. The extracted features correspond to the outcome of step 708.

With respect to the supervised machine learning process (707), the second table 1006 of FIG. 10 corresponds to the classification information obtained in step 710. The information in the table 1006 includes the classification of each ECoG record included in the sample of ECoG records 1002 into one of the seizure onset types. Information corresponding to the extracted features included in the first table 1004 and the seizure onset type classifications in the second table 1006 are inputs to a supervised machine learning process 1008. This corresponds to step 712 of FIG. 7A. The result of the supervised machine learning process 1008 is a classification process 1014 that provides a mapping between extracted features and the human-defined seizure onset types. This classification process 1014 corresponds to the classification process of FIG. 7A.

B. Clustering Process

In a clustering process (709), the extracted feature sets from step 708 are input to a clustering process that automatically forms one or more clusters of similar extracted feature sets. Each formed cluster corresponds to a different seizure onset type. In this case, the seizure onset types formed by the clustering process may be referred to as "machine-determined seizure onset types." By way of example not limitation, the clustering process may be any of K-means clustering, neural network self-organizing maps, or fuzzy clustering. The clustering process clusters the ECoGs based on the extracted features. The result of clustering process of step 714 is a classification process configured to map extracted feature sets to machine-determined seizure onset types.

The classification process is also configured to provide a measure of probability that an extracted feature set represents a machine-determined seizure onset type. A measure of probability for an extracted feature set may be provided for more than one seizure onset type, with the total sum of probabilities being 1. The accuracy of the classification process in matching extracted features sets to a particular seizure onset type depends on the quantity of inputs provided to the clustering process in step 714, with an increased number of inputs resulting in an increased level of accuracy. In one configuration, sufficient inputs are provided to the clustering process to provide a classification process having a minimum classification accuracy of around 80% on ECoG records with seizure onsets that were not used for creating the classification process. The machine-determined seizure onset types formed by the clustering process may not correlate with the seizure onset types obtained in step 710 of the supervised machine learning process. For example, the clustering process may identify a number of different machine-determined seizure onset types different from the six human-defined seizure onset types shown in FIG. 8A through FIG. 8F. The clustering process 709 does not involve obtaining seizure onset type classification information derived from human input.

In an example where the machine identified two clusters representing two distinct seizure onset types, seizure onset type 1 may include seizure onsets that contain a Shannon entropy less than 5 and peak frequency less than 6 Hz. Stimulation therapy may be effective for seizure onset type 1 when it comprises very high frequency stimulation (defined with stimulation parameters: 0.6-0.8 mA pulse amplitude, 200-300 Hz frequency, 80-100 µS pulse width, 100-220 ms burst duration). Seizure onset type 2 may include seizure onsets that contain a Shannon entropy greater than 5 and peak frequency greater than 6 Hz. Stimulation therapy may be effective for seizure onset type 2 when it comprises low frequency stimulation (defined with stimulation parameters: 1-3 mA pulse amplitude, 1-10 Hz frequency, 120-160 mS pulse width, 1-3 second(s) burst duration).

Referring again to FIG. 10, with respect to the clustering process 709 of FIG. 7A, the information corresponding to the extracted features included in the first table 1004 of FIG. 10 is input to a clustering process 1010. This corresponds to step 714 of FIG. 7A. The result of the clustering process 1010 is a classification process 1012 that provides a mapping between extracted features and machine-determined seizure onset types. This classification process 1012 corresponds to the classification process 705 of FIG. 7A. In the example of FIG. 10, the clustering process 1010 processed the extracted features and identified three clusters 1001, 1003, 1005 of similar extracted features. Based on the three clusters 1001, 1003, 1005, the clustering process identified three corresponding machine-determined seizure onset types.

Determining Dominant Seizure Onset Type

Figure 7B:
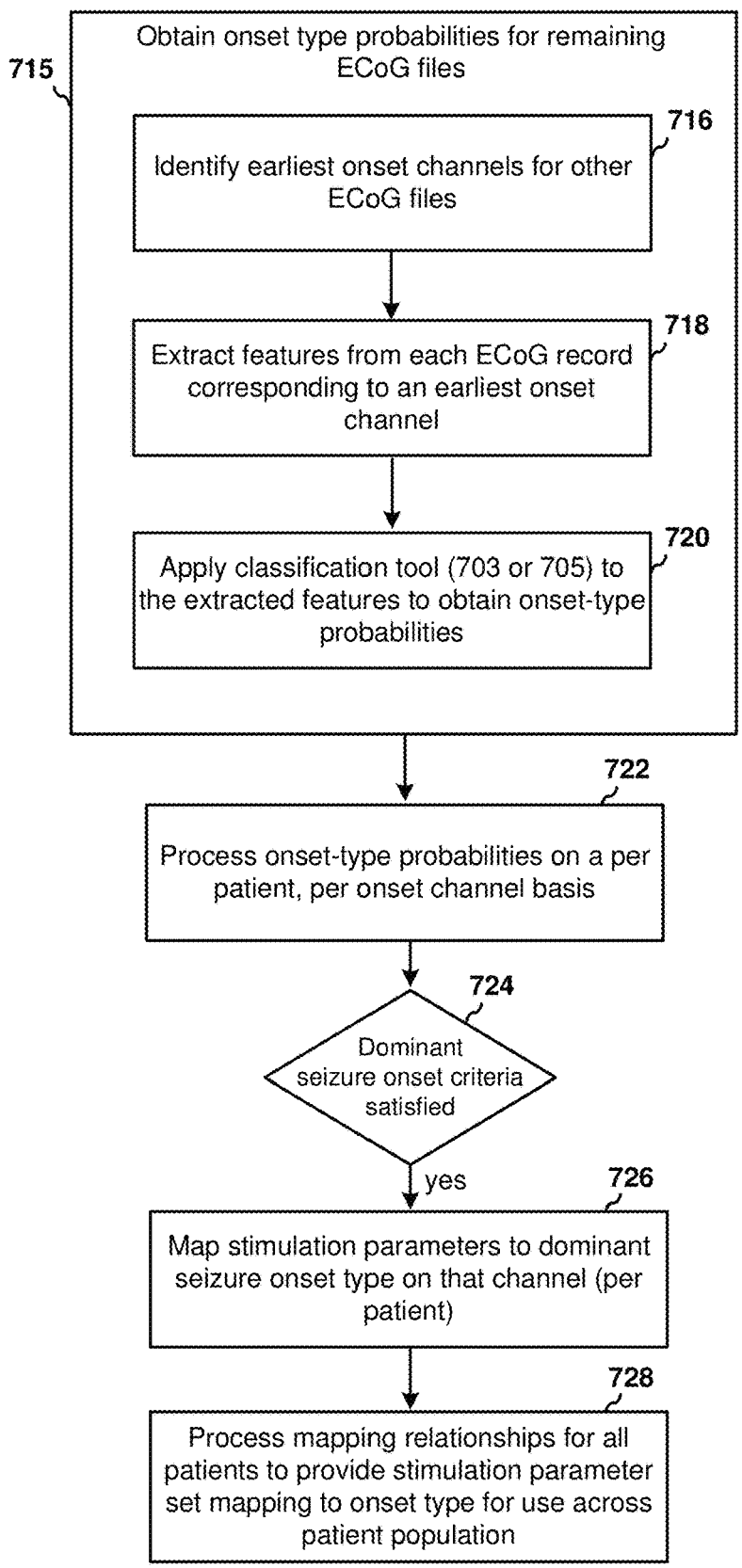

With reference to FIG. 7B, at step 715, seizure onset type probabilities are obtained for other ECoGs using either the supervised machine learning or clustering approaches described above. To this end, at step 716, other ECoG files are processed to identify the time of occurrence of a seizure onset, and then to identify the channel having the earliest seizure onset channel. In one implementation, the other ECoGs may be the remaining ECoG files that were not selected for processing in step 704. For example, if 20% of the ECoG files were selected for processing at step 704, the remaining 80% of the ECoG files are processed at step 716. In the case of the clustering process 709, as previously described, 80% of the ECoG files may be selected for processing at step 704. In cases where multiple ECoG records have similar seizure onset times, all such ECoG records are identified as earliest seizure onset channels.

At step 718, features are extracted from ECoG records of the identified earliest seizure onset channels. The features extracted at step 718 are the same features extracted at step 708 and may include, for example, the number of peaks, dominant frequency, mean amplitude at seizure onset, line length, and energy in beta band/energy in theta band. Any of the many additional features in Table 2 may also be extracted and processed by the external device.

At step 720, the extracted features from the earliest-seizure-onset-channel ECoG records are processed by the classification process resulting from either of supervised machine learning process 707 or the clustering process 709. Based on the extracted features, the classification process assigns probability values for the ECoG record with the earliest seizure onset as belonging to one of the seizure onset types associated with the classification process. In the case of a classification process from the supervised machine learning process 707, the seizure onset types may correspond to human-defined seizure onset types. In the case of a classification process from the clustering process, the seizure onset types may correspond to machine-determined seizure onset types. The classification process may assign multiple probabilities to an ECoG record with an earliest-seizure-onset, wherein each assigned probability corresponds to one of the seizure onset types. The probabilities may range between 0 and 1, with the total sum of the probabilities being 1.

Figure 11:
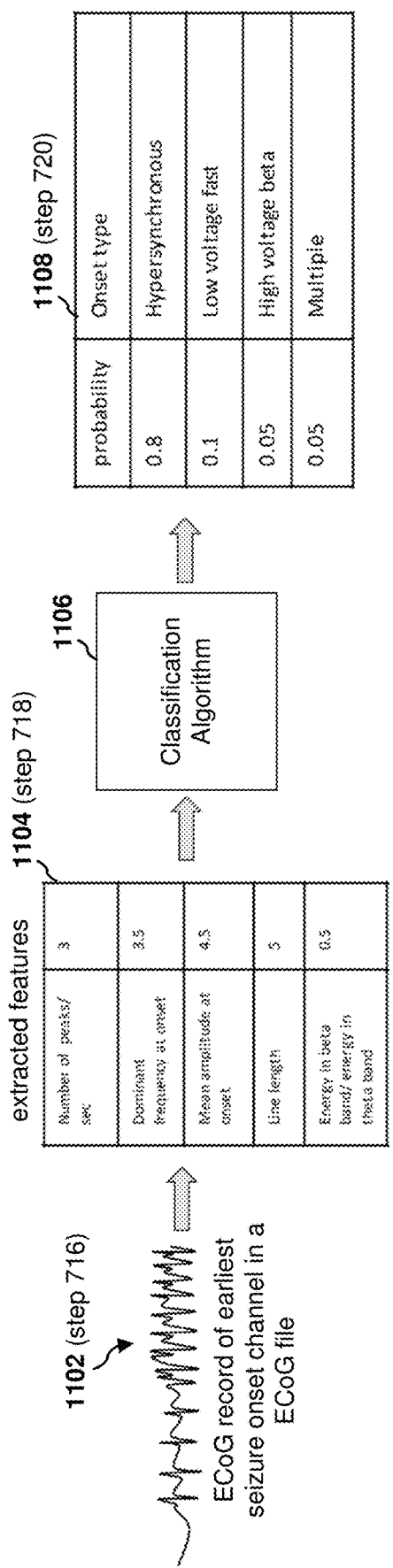
Figure 14:
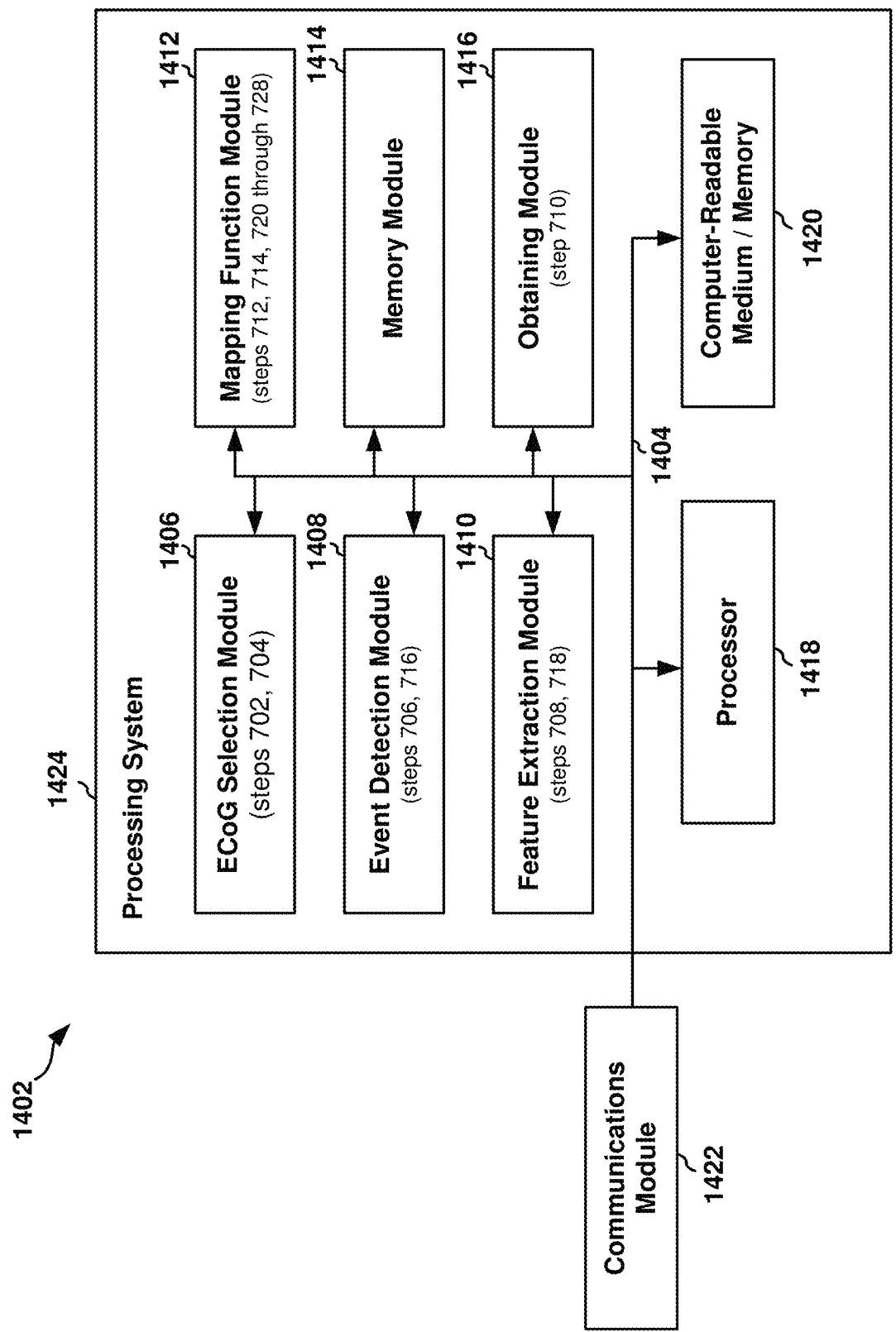
FIG. 14 is a block diagram illustration of an external device configured to implement the mapping function creation of FIG. 7A and FIG. 7B.

FIG. 11 further illustrates the method of FIG. 7B, especially steps 716, 718, and 720 of FIG. 7B, for a single one of the earliest seizure onset channels. The single ECoG record 1102 represents an ECoG record of an earliest seizure onset channel corresponding to the outcome of step 716. The first table 1104 of FIG. 11 includes values of features extracted from the ECoG record. The extracted features correspond to the outcome of step 718. The extracted features are run through a classification process 1106 that resulted from either of steps 712 or step 714. The second table 1108 of FIG. 11 lists the seizure onset-type probability outcomes for the ECoG record 1102 as determined by the classification process 1106. In this example, the classification process 1106 determines: the probability that the ECoG record 1102 represents a hypersynchronous seizure onset type, i.e., 0.8, the probability that the ECoG record represents a low voltage fast seizure onset type, i.e., 0.1; the probability that the ECoG record represents a high voltage beta seizure onset type, i.e., 0.05; and the probability that the ECoG record represents a multiple seizure onset type, i.e., 0.05. The seizure onset-type probabilities correspond to the outcome of step 720.

Referring again to FIG. 7B, at step 722, upon completion of the processing of each of the remaining ECoG records in step 715, the probabilities obtained in step 715 are further processed on a per patient, per earliest seizure onset channel basis. To this end, for each particular channel (CH1, CH2, CH3 or CH4) identified as an earliest seizure onset channel in steps 718, 720, the seizure onset-type probabilities determined for each particular seizure onset type for that particular channel are processed together. For example, with reference to FIG. 12, four sets of seizure onset-type probabilities 1202, 1204, 1206, 1208 for a particular patient are shown. Each seizure onset-type probability set 1202, 1204, 1206, 1208 corresponds to a different ECoG record, e.g., ECoG1, ECoG2, ECoG3, ECoG4, on the same earliest seizure onset channel, e.g., channel 1. The seizure onset-type probabilities correspond to the outcome of step 720. The respective probabilities of each seizure onset type for this particular channel are processed to obtain the mean of the probabilities. The result of this processing is shown in the mean probabilities set 1210. The mean probabilities set corresponds to the outcome of step 722.

At step 724, the process determines if the mean probabilities set satisfies a dominant seizure onset type criterion. The criterion may correspond to a threshold probability. For example, a threshold probability may be 0.8. In this case, if a mean probability of a seizure onset type as determined in step 722 is greater than the threshold, then the seizure onset type corresponding to the mean probability that is above the threshold is identified as the dominant seizure onset type on that particular channel for that particular patient.

Referring again to FIG. 12, based on the mean probabilities set 1210, and a threshold of 0.8, the outcome of step 724 would be "yes." In this case, the channel (CH1) in that patient is considered to have a dominant seizure onset type. Given the values of the mean probabilities set 1210, the hypersynchronous seizure onset type would be identified as the dominant seizure onset type 1212 for the earliest seizure onsets that occur on Channel 1 for this particular patient. Alternatively, a dominant seizure onset type on a channel may be defined as the one that has the highest probability. In this case, no threshold is set for determining the dominant seizure onset type. If two or more seizure onset types have the same probability, a dominant seizure onset type may be chosen from the two seizure onset types at random. As an additional criterion of step 724, the mean probabilities of a set 1212 may be based on a threshold number of ECoGs. For example, a threshold number of ECoGs may be 10, but this number could be lower or higher. One reason for having a threshold number of ECoGs for determining mean probabilities is to ensure a decision of a dominant seizure onset type is based on sufficient information. More than one channel can have dominant seizure onset type in the same patient. For example, the process of steps 716 through 724 may be performed for a different channel (Channel 2) for the same patient and may yield a different dominant onset type than that for Channel 1.

Mapping Seizure Onset Types to Effective Stimulation Parameter Subspaces and Stimulation Parameter Sets Referring again to FIG. 7B, at step 726, one or more stimulation parameter sets may be mapped to the dominant seizure onset type on the particular channel. The mapped stimulation parameter sets are based on observed metrics for the particular patient. For example, a record of different stimulation parameter sets applied to the particular channel and corresponding metrics related to effectiveness of such stimulation parameter sets, such as seizure reduction rate (reduction in clinically reported seizures) and/or event detection rate reduction (reduction in the number of neurological events the neurostimulator is configured to detect over a predetermined period of time), may be used to form a number of stimulation parameter sets. Referring again to FIG. 12, different effective stimulation parameter sets are mapped 1214 to the dominant seizure onset type in the particular patient, on the particular channel (CH1). The mapping 1214 corresponds to the outcome of step 726.

Referring again to FIG. 7B, at step 728, mapping relationships between a particular dominant seizure onset type and effective stimulation parameter sets from across a patient population are processed together to provide a final mapping of stimulation-parameter-sets to seizure onset type that may be applied across the patient population. For example, with reference to FIG. 13, a number of collections 1302, 1304, 1306 of stimulation parameter sets 1302*a*-1302*d*, 1304*a*-1304*d*, 1306*a*-1306*d*, along with corresponding metrics of effectiveness are shown for three different patients. These collections 1302, 1304, 1306 represent stimulation parameter sets for use in treating a neurological condition having a hypersynchronous seizure onset type. In the example of FIG. 13, three collections 1302, 1304, 1306 are shown, however, the number of collections may be in the range of 5 to 100.

The information included in the collections 1302, 1304, 1306 is processed to provide a final mapping 1308 of a stimulation parameter subspace 1312 and a default stimulation parameter set 1310 to the hypersynchronous seizure onset type that may be applied across the patient population. The stimulation parameter sets 1302*a*-1302*d*, 1304*a*-13-4*d*, 1306*a*-1306*d* from the collections 1302, 1304, 1306 may be combined to provide a default stimulation parameter set 1310 and a stimulation parameter subspace 1312 by running a clustering process on the collections 1302, 1304, 1306 of the stimulation parameter sets. Effectiveness in reducing seizures may be a metric used for forming the stimulation parameter subspace 1312 and a default stimulation parameter set 1310. For example, a threshold on effectiveness, e.g., 75% reduction in seizure rate, may be established for selecting stimulation parameter sets from the collections 1302, 1304, 1306 that are sent to the clustering process. A default stimulation parameter set may be set based on what set of parameters worked best in most of the patients. For example, a particular stimulation parameter set that resulted in the best effectiveness, e.g., highest seizure reduction, for most patients within the collections 1302, 1304, 1306 may be set as the default. Alternatively, a default stimulation parameter set may be formed on a parameter-by-parameter basis by selecting a value for each individual parameter, e.g., frequency, amplitude, pulse width, etc. that was most effective, e.g. stimulation with that parameter value resulted in the highest seizure reduction, across the collections 1302, 1304, 1306. As another alternative, the default stimulation parameter set may be selected as the median or mean value for each stimulation parameter within the collection 1302, 1304, 1306. For example, if a significant number of the frequencies within the collection 1302, 1304, 1306 establish a range of frequencies of 100 Hz-150 Hz, the default stimulation value for frequency may be selected to be 125 Hz. Any outlier frequencies within the collection 1302, 1304, 1306 that do not fall in the range may be discarded. As explained above, a stimulation parameter subspace 1312 is defined by a number of stimulation parameters and corresponding ranges for the stimulation parameters. The final mapping 1308 may also include a set of default stimulation parameters 1310, each having a discrete value within the range of the stimulation parameter subspace 1312. The stimulation parameters define an instance of stimulation therapy (e.g., an electrical stimulation waveform to be generated by the neurostimulator and delivered through stimulation electrodes) for treating a neurological condition or disorder corresponding to the seizure onset type.

The foregoing processes of FIGS. 7A and 7B, and FIGS. 10 through 13 may be repeated for each seizure onset type to provide a mapping of stimulation parameter subspaces to the seizure onset types. With reference to FIG. 13, example mappings are shown for a hypersynchronous seizure onset type 1308, a low voltage fast seizure onset type 1314, and a high voltage beta seizure onset type 1316.

Implementation of the Mapping Function Module

Figure 15:
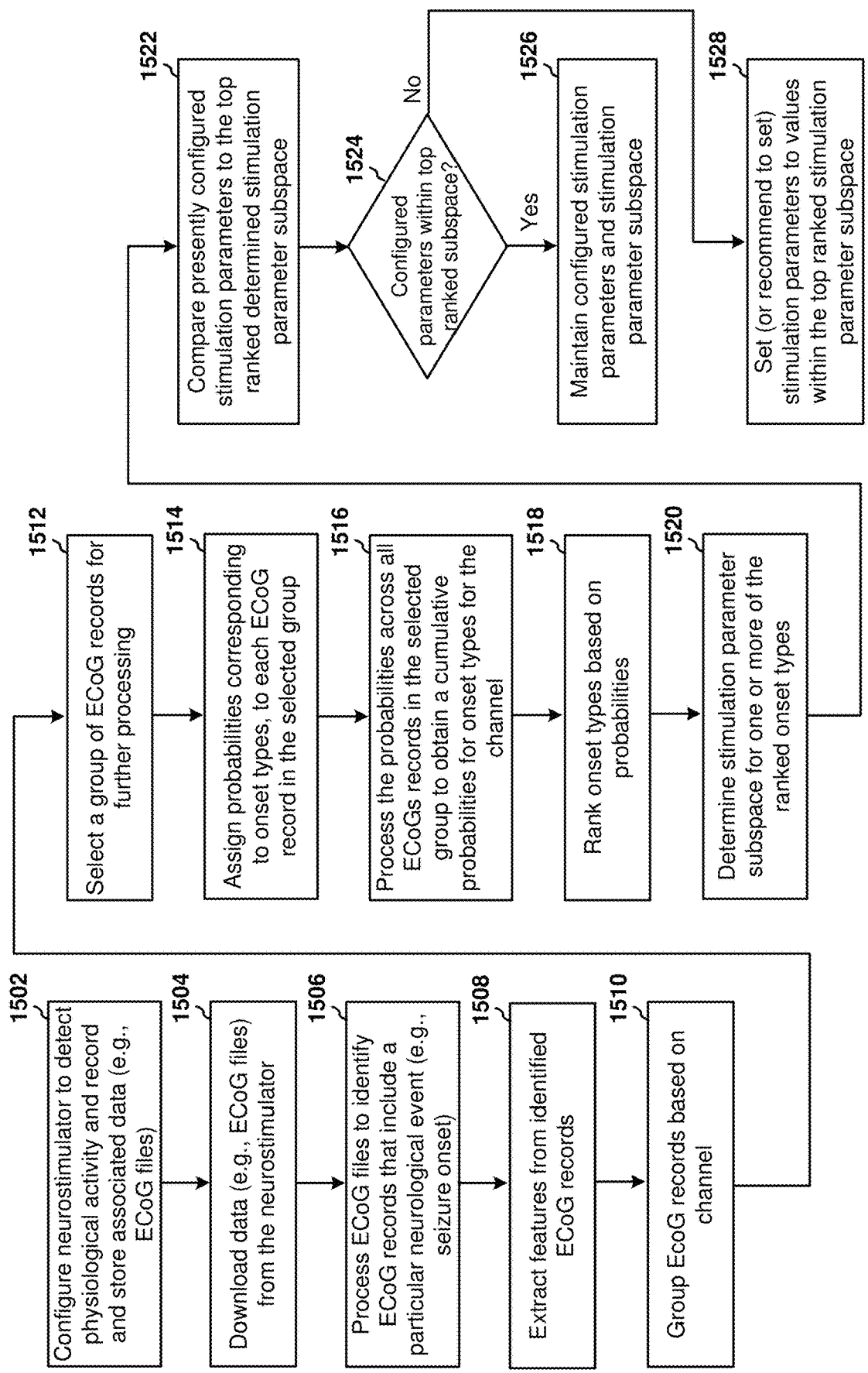
FIG. 15 is a flow chart of a method of selecting a stimulation parameter subspace for a neurostimulator.
Figure 16:
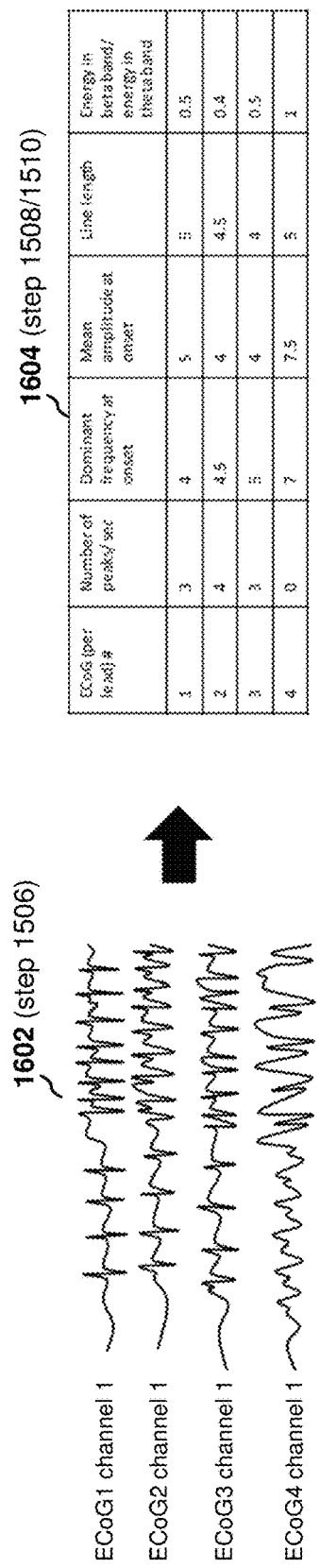
FIG. 16 is an illustration of an example process flow associated with the method of FIG. 15.

FIG. 15 is a flow chart of a method of selecting a stimulation parameter subspace for a neurostimulator. The method may be performed by one or more processers configured to execute the steps in the methods. The one or more processors may include an external component, such as a programmer 212, 228, 230, 232 (FIG. 2), having executable code defining one or more modules configured to implement the steps of the method. FIG. 16 further illustrates some of the steps of the method of FIG. 15.

At 1502, a neurostimulator 110 is configured with a default detection parameter set for identifying a detected event, e.g., a seizure onset neurological event, and with a stimulation parameter set for generating and delivering an instance of stimulation as a therapy in response to a detected event. With respect to the detection parameters, as described above, a neurostimulator 110 may be programmed by a physician to acquire physiological data (e.g., electrographic activity) from one or more sensing locations in a patient, and to process, analyze and evaluate the acquired physiological data in an effort to determine whether the acquired physiological data evidences what the neurostimulator 110 is programmed to recognize as a detected event.

With respect to the stimulation parameter set, the neurostimulator 110 may be programmed with a stimulation parameter subspace that defines a range of values for each of several stimulation parameters. The neurostimulator 110 may also be programmed with a stimulation parameter set, wherein each parameter has a value that falls within a respective range defined by the stimulation parameter subspace.

The neurostimulator 110 is also configured to record and, in some instances, to store data. The recorded data may include multiple measures of physiological activity, including for example, electrographic activity in the form of ECoG files, duration of detected events, rate of occurrences of detected events over time, as well as the amplitude of evoked potentials as generated by the diagnostic stimulator in the therapy subsystem described with reference to FIG. 5. Recorded physiological activity may also include pH levels in local brain tissue and neurochemical measures, such as tissue oxygenation and neurotransmitter levels.

At 1504, ECoG files recorded by the neurostimulator are downloaded from the neurostimulator to the external component 212. The ECoG files may be further processed by the programmer or uploaded to a secure database 222 for subsequent processing.

At 1506, the ECoG files may be processed by the external device 212 to identify those ECoG records in each ECoG file that include a particular neurological event type, e.g., a seizure onset type. To this end, each of the downloaded ECoG files for the patient may be initially assessed to determine if it contains an electrographic seizure. Each ECoG file found to contain an electrographic seizure may be further assessed to determine which seizure onset type it contains. ECoG files containing a seizure onset are then further processed to identify the ECoG record with the earliest seizure onset. ECoG records with the earliest seizure onsets are grouped by channel number.

At 1508, features are extracted from those ECoG records that include a seizure onset. With reference to FIG. 16, these extracted features may include, for example, the number of peaks, dominant frequency, mean amplitude at seizure onset, line length, and energy in beta band/energy in theta band. In some embodiments, any of the many additional features listed above in Table 2 may also be extracted and processed by, for example, the external component 212. The external component may extract features from ECoG records using known algorithms.

At 1510, ECoG records and the corresponding extracted features are grouped based on their corresponding channels. For example, with reference again to FIG. 16, the first table 1604 represents features extracted from four ECoG records recorded on the same channel, i.e., Channel 1.

At 1512, a group of ECoG records for each channel containing a seizure onset is selected for further processing. At 1514, probabilities that the seizure onset belongs to a specific seizure onset type are assigned to each ECoG record in the group. To this end, the extracted features for each ECoG record in the group are run through a classification module that assigns a probability to the ECoG record that the seizure onset contained in that ECoG record belongs to one of a predetermined seizure onset types. The classification module may be based on either a supervised machine learning process, or a clustering process. Each of the second, third, fourth, and fifth tables 1606, 1608, 1610, 1612 in FIG. 16 is an example of probabilities assigned to a particular ECoG record in the group of ECoG records corresponding to Channel 1.

At 1516, the probabilities across all ECoG records in the selected group 1604 (i.e., on the same channel) are processed to obtain a set of cumulative probabilities for seizure onset types for the group. The set of cumulative probabilities may be based only on the ECoG records in the present or most recently uploaded group, or may be based on past or previously uploaded ECoG records on the same channel. In the sixth table 1614 of FIG. 16, the second column of probabilities represents a set of probabilities that is based on the present group of ECoGs 1604. The third column represents a set of probabilities based on past ECoGs from the same channel as the selected group of ECoGs. The fourth column represents an aggregate probability based on present and past ECoGs. For example, a weighted average probability number may be computed for a patient based on present and past ECoGs of the patient. ECoGs uploaded in the near past may be given a greater weight than ECoGs uploaded in the distant past. If the weighted average probability in any one seizure onset type exceeds a pre-specified number (say 0.8) for all ECoGs on a particular earliest onset channel for a patient, then a dominant seizure type for that particular channel is found for that patient. A patient can have several dominant seizure onset types, each for a different earliest seizure onset channel. The top ranked seizure onset type per channel is then identified for the patient.

At 1518, the seizure onset types included in the set of probabilities are ranked in order of most likely to least likely seizure onset type. In FIG. 16, the sixth table 1614 ranks the seizure onset types based on probabilities, with the hypersynchronous seizure onset type being the most probable seizure onset type on Channel 1, followed by the low voltage fast seizure onset type, the high voltage beta seizure onset type and the multiple seizure onset type.

At 1520, stimulation parameter subspaces are determined for one or more of the ranked seizure onset types for the channel corresponding to the selected ECoG group. To this end, a mapping function module is used to map seizure onset types to stimulation parameter subspaces which, by some measure, have been determined to be effective or to have led to a therapeutic result for the patient. An effective stimulation parameter subspace may be determined for the top ranked electrographic seizure onset type. The determined stimulation parameter subspace is to be used for the channel corresponding to the selected ECoG record group. For example, the last table 1616 in FIG. 16 represents effective stimulation parameter subspaces and the corresponding default stimulation parameter sets for the top two ranked seizure onset types.

At 1522, once the stimulation parameter subspace is determined, the stimulation parameter subspace is compared to the present stimulation parameter subspace (if any) that is programmed into the neurostimulator. (If this is the first time a stimulation parameter subspace has been mapped for the neurostimulator, there will be no "present stimulation subspace").

At 1524, if the present stimulation parameter set is within the top ranked stimulation parameter subspace, the process proceeds to 1526, where the present stimulation parameter set is maintained. At 1524, if the present stimulation parameter set falls outside the top ranked stimulation parameter subspace, then the process proceeds to 1528, where the external component provides an output to a change in stimulation parameter set to fall within the top ranked stimulation parameter subspace. The output may be a command to the neurostimulator to change the values of the stimulation parameters so that they fall within the top ranked stimulation parameter subspace. Alternatively, the output may be a recommendation to change the values of the stimulation parameters within the top ranked stimulation parameter subspace, for example to a user interface. Additionally, the recommendation could be provided as an input to an integration module as is described with reference to, for example, FIG. 17 below.

In summary, and with reference again to FIG. 16, embodiments described above relate to the selection (or recommendation) of a stimulation parameter subspace. To this end, one or more features 1604 from a plurality of electrographic signals (ECoGs) 1602 recorded on the same channel of a neurostimulator are extracted from the signals. The electrographic signals 1602 include a neurological event resulting from the neurological condition. One or more probabilities 1606, 1608, 1610, 1612 are assigned to each of the plurality of electrographic signals 1602. The one or more probabilities 1606, 1608, 1610, 1612 correspond to a probability that the electrographic signal 1602 includes one of a plurality of types of neurological event. The types of the neurological events, e.g., hypersynchronous seizure onset, low voltage fast seizure onset, high voltage beta seizure onset, multiple seizure onset, included in the electrographic signals 1602 are ranked 1614 based on their corresponding probabilities. A stimulation parameter subspace 1616 is determined for one or more of the ranked types of the neurological events based on the probabilities of the ranked types of the neurological events.

In one embodiment, the mapping function module may include at least partially or entirely in an external component of a neurostimulation system according to embodiments, such as a laptop or tablet computer or database with an associated database application (e.g., a website), and used by the external component to select stimulation parameters sets for an implantable neurostimulator. Alternatively, the mapping function module may be provided at least in part or entirely in an implantable neurostimulator according to the invention, and used by the neurostimulator to select stimulation parameter sets for the neurostimulator, automatically, and in real time.

Stimulation Parameter Selection by Neurostimulator

Embodiments described below relate to selecting in real time using an implanted neurostimulator a stimulation parameter subspace and stimulation parameter set based on detected types of neurological events and delivering stimulation using the selected values for the stimulation parameters.

Figure 20:
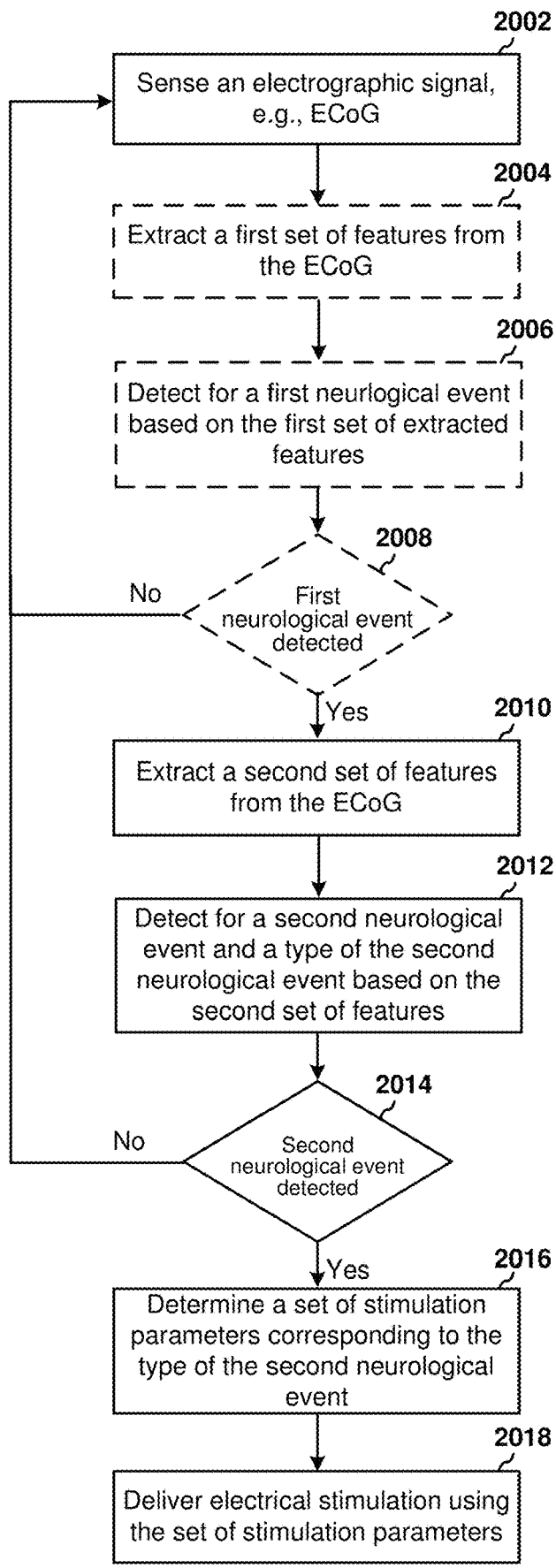
FIG. 20 is a flow chart of a method of delivering electrical stimulation therapy to a patient.

FIG. 20 is a flow chart of a method of delivering electrical stimulation therapy to a patient. Provided in a neurostimulator are a classification module and a mapping function module which, respectively, classify features in electrographic activity as representing particular types of neurological events, e.g., seizure onset types, and associate effective stimulation parameter subspaces to types of neurological events.

The neurostimulator is programmed to detect a neurological condition, e.g., an epileptic seizure, based on sensed electrographic activity, and to detect a neurological event, e.g., a seizure onset, associated with the neurological condition according to a detection parameter set. The neurostimulator is also programmed to deliver electrical stimulation therapy, as defined by a stimulation parameter set, in response to detection of the neurological event.

At 2002, the neurostimulator senses electrographic activity in the patient's brain. The electrographic activity may be represented by an electrographic signal, e.g., an ECoG. The ECoG may be sensed using one of a number of available sensing channels defined by a pair of electrodes.

At 2004, the neurostimulator feature extraction module optionally extracts a first set of features from the ECoG. The first set of extracted features may be used to detect for a first neurological event, e.g., a seizure. These features may include one or more of the features employed by the previously described half-wave tool, line-length tool and area tool, to detect a seizure. Extracted features may include a line length value and a band pass-filtered value. The feature extraction module may continuously extract features from the sensed electrographic signals, e.g., ECoGs, which are stored in a short-term, e.g. 30-second, rolling buffer of the neurostimulator. The amount of data used to compute each of these features may vary, for example, two seconds of data may be used to compute the line length, while one second of data may be used to compute the band pass-filtered data.

At 2006, the neurostimulator optionally detects for a first neurological event based on the first set of extracted features. In one example, the first set of extracted features may indicate a line length with a value of 5 and a band pass-filtered value of 10. Based on this, an analysis tool of the neurostimulator may detect a seizure.

At 2008, if the first neurological event is not detected, the process returns to 2002, where the neurostimulator continues to monitor (sense) the electrographic signal If, however the first neurological event is detected, the process proceeds to 2010, where the neurostimulator feature extraction module extracts a second set of features from the electrographic signal. The second set of features may include one or more features employed by a neurological event type analysis tool to identify the type of seizure onset. These extracted features may include one or more of number of peaks per second, dominant frequency, mean amplitude, energy in beta band/ energy in theta band.

The second set of features may be continuously extracted from sensed electrographic signals, e.g., the ECoGs, which are stored in a short-term, e.g. 30 second, rolling buffer of the neurostimulator. Alternatively, when the process implements optional steps 2004, 2006 and 2008, the second set of features may be extracted from sensed electrographic signals, e.g., the ECoGs, after detection of the first neurological event. This is beneficial in that it reduces the amount of processing performed by the neurostimulator and thereby reduces power consumption and conserves resources of the implanted device. To this end, the neurostimulator retrieves extracted features from a region of the electrographic signal that occurred immediately prior to the detected first neurological event. The region may be a short window of time, e.g. 1 second.

At 2012, the neurostimulator monitors for a second neurological event, e.g., a seizure onset, and a type of the second neurological event based on the second set of extracted features. The neurostimulator may detect the neurological event and then classify it into a neurological event type based on the second set of extracted features by applying the second set of features to the classification module that is configured to associate sets of features with types of neurological event. In one example, the second set of extracted features includes a number of peaks per second of 4, a dominant frequency at seizure onset of 4, a mean amplitude at seizure onset of 5, a line length of 5 and an energy beta band/energy theta band of 0.45. Based on one or more of these extracted features, the analysis tool of the neurostimulator may detect a seizure onset, and the classification module of the neurostimulator may identify the seizure onset as a hypersynchronous onset type. The second set of extracted features may require higher computational complexity and may be computed from y seconds of ECoG stored in the rolling buffer. These features may be used to identify the seizure onset channel(s) and classify the seizure onset type on the seizure onset channel(s) into the several seizure onset categories.

At 2014, if the second neurological event is not detected, the process returns to 2002, where the neurostimulator continues to sense electrographic activity. If, however the second neurological event is detected and the classification module identifies the type of seizure onset, the process proceeds to 2016, where the mapping function module of the neurostimulator determines an effective stimulation parameter set corresponding to the type of the second neurological event. The stimulation parameter set defines an instance of stimulation therapy for treating the neurological disorder. The neurostimulator may determine a stimulation parameter set corresponding to the type of the second neurological event by applying the type of the second neurological event to a mapping function module that associates each of a plurality of different types of the second neurological events to a n effective stimulation parameter subspace and default stimulation parameter set. For example, based on an identification of a hypersynchronous seizure onset type, a mapping function module of the neurostimulator may determine a stimulation parameter subspace of: 0.8-1.5 mA amplitude, a 6-10 Hz interburst frequency, a 100-150 Hz intraburst frequency, a 75-150 μs pulse width and a 0.5-2 second burst duration. Within the stimulation parameter subspace the neurostimulator mapping function module may select a corresponding default stimulation parameter set.

Depending on the computational capability of the neurostimulator, a simplified classification algorithm that does not depend on any machine learning may be devised based on just a few important features. The mapping function programmed into the device is used to identify the most effective stimulation parameters.

While the stimulation parameter set corresponding to the type of the second neurological event is being determined, an instance of stimulation may be delivered using other values of the stimulation parameters. For example, the neurostimulator may obtain from memory and deliver one or more of the values for the stimulation parameters that comprise the last stimulation parameter set for the patient, a stimulation parameter set that has been most commonly used in the patient, or a default stimulation parameter set programmed in the neurostimulator. Upon determination of a stimulation parameter set corresponding to the type of the second neurological event, delivery of an instance of stimulation using any of these other stimulation parameter sets may be stopped, and the process proceeds to step 2018.

At 2018, the neurostimulator delivers the instance of stimulation to the brain. In one implementation, the electrographic signals are sensed over a sensing channel defined by a pair of electrodes, and the stimulation is delivered to same electrodes. The neurostimulator may be programmed to deliver electrical stimulation based on the determined stimulation parameter sets through more than one channel. Such delivery may occur synchronously or with a small delay in each channel. In the event where more than one channel is identified to be the seizure onset channel, an effective stimulation parameter set identified for each seizure onset type (on a seizure onset channel) will be delivered to the seizure onset channel and any other channels on the same lead that do not have a seizure onset.

Returning to 2002, in instances where optional steps 2004, 2006 and 2008 are not performed, the process proceeds directly to 2010, where the neurostimulator extracts a second set of features from the electrographic signal sensed in 2002. The second set of features may include one or more features employed by a neurological event type analysis tool to identify the type of seizure onset. In a first example, the second set of extracted features includes a number of peaks per second of 0, a dominant frequency at seizure onset of 1, a mean amplitude at seizure onset of 1, a line length of 1 and an energy beta band/energy theta band of 0.1. At 2012, based on one or more of these extracted features, the analysis tool of the neurostimulator may detect a seizure onset, and the classification process of the neurostimulator may determine that a neurological event has not been detected. Accordingly, the process returns to 2002.

In a second example, the second set of extracted features includes a number of peaks per second of 3, a dominant frequency at seizure onset of 4, a mean amplitude at seizure onset of 5, a line length of 5 and an energy beta band/energy theta band of 0.45. At 2012, based on one or more of these extracted features, the analysis tool of the neurostimulator may detect a seizure onset, and the classification module of the neurostimulator may detect an occurrence of a neurological event, e.g., seizure onset, and identify the seizure onset as a hypersynchronous onset type. In this case, the process would proceed to 2016 and 2018 as described above.

Integration Module

The integration module allows embodiments of the neurostimulator system to integrate a detected neurological event type with other information before the neurostimulator generates and delivers a stimulation parameter set selected from a stimulation parameter subspace or corresponding to the default stimulation parameter set proposed by the mapping function module. Put another way, the integration module allows the neurostimulation system to consider factors in addition to or other than the result of a mapping function before determining whether to adjust a stimulation for a patient when a particular neurological event, in these examples, a seizure onset neurological event type, is detected by the neurostimulator.

Figure 17:
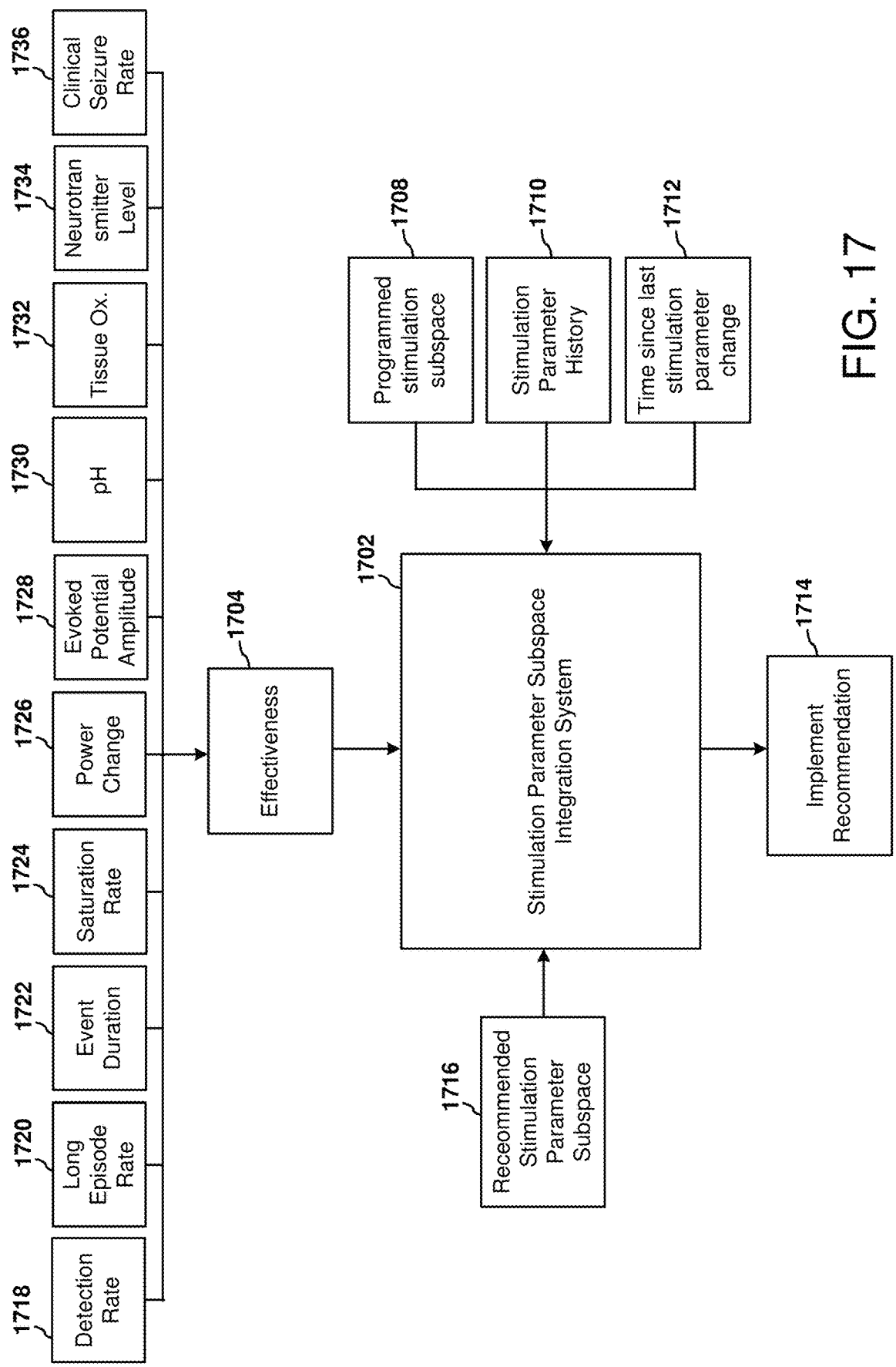
FIG. 17 is a block diagram illustrating a stimulation parameter subspace integration system.

More particularly, and referring now to the block diagram of FIG. 17, the integration module 1702 is configured to determine whether to: (1) narrow the stimulation parameter space available to the neurostimulator to the stimulation parameter subspace resulting from the mapping function (so that a clinician can select discrete values from within the subspace to define instances of stimulation); (2) change the stimulation parameter subspace available to the neurostimulator from a previously established stimulation parameter subspace (if there is one) to a different one (again, so that a clinician can select discrete values from within the (new) subspace to define instances of stimulation); or (3) have the neurostimulator use the default stimulation parameter set proposed by the mapping function for generating and delivering stimulation therapy.

One or more of data elements in addition to the detection of the seizure onset may be relevant to the determination of whether a neurostimulator should use the results of the mapping function 1716 ("recommended stimulation parameter subspace" or the default stimulation parameter set) to control or adjust the stimulation therapy it generates and delivers to a patient in response to detection of a particular seizure onset type. For example, and with reference to FIG. 17, the data elements may relate to or include: (1) the present stimulation parameter set with which the neurostimulator is programmed/configured 1708, and a comparison between it and either the default stimulation parameter set or the stimulation parameter subspace resulting from the mapping function; (2) the amount of time that has elapsed since the last time the stimulation parameter set was changed 1712; (3) a history of adjustments to the stimulation parameter sets and time between adjustments 1710; (4) a measure of the effectiveness of the present therapy the patient is receiving, such as derived from metrics such as: (a) the rate at which the neurostimulator has detected events according to the detection parameter set(s) 1718; (b) the duration of events detected according to the detected parameter set(s) 1722; (c) the number of times certain criteria has been satisfied that correlates to a clinical seizure, such as the number of times sensed electrographic activity comprises a "long episode" 1720 (continues to evidence abnormal activity for a predetermined length of time), or a "saturation" 1724 (causes amplifiers in the sensing circuitry of the neurostimulator to saturate or peg the rails of the amplifiers); (d) the rate of clinical seizures 1736 (e.g., as reported in a seizure diary, for example, by the patient or the patient's caregiver) changes in power in pre-specified frequency bands 1726; (e) evoked potential amplitude 1728; (f) any one of a number of physiological parameter values other than those associated with the detected neurological event, including but not limited to (i) pH; (ii) oxygenation of the neural tissue 1730; and (iii) the level of neurotransmitters in the neural tissue 1734.

It will be appreciated that the metrics used in the measure of effectiveness 1704 may be related to physiological activity that is electrophysiological and that which is not. In FIG. 17, the electrophysiological metrics include the detection rate (or count) 1718, the long episode rate 1720, the detected event duration 1722, the saturation rate 1724, the changes in power in specific frequency bands 1726, and the evoked potential amplitude 1728. The non-electrophysiological metrics in FIG. 17 include pH shifts 1730, tissue oxygenation 1732, neurotransmitter levels 1734, and clinical seizure rate (or count) 1736. Data corresponding to one or more of pH level, clinical seizure rate, seizure detection rate, long episode rate, saturation rate and neurochemical levels are processed to determine a measure of effectiveness of the present stimulation parameter set or the present stimulation parameter subspace (if there is one).

In some embodiments, the neurostimulator 110 may be configured to acquire the data elements for some of the metrics from one or more sensing elements that are situated in one or more locations in a patient. For example, a measure of a neurochemical level may include tissue oxygenation, and/or neurotransmitter levels. During periods of increased neural activity, energy utilization by neural tissue results in increased metabolism that lowers extracellular oxygen concentrations and pH. At the same time, chemical messengers are released by neural tissue that results in vasodilation and an increased supply of nutrients. This vasodilation increases blood flow, re-supplying oxygen and clearing carbon dioxide. Because vasodilation overcompensates for the metabolic effects, the net result is an increase in oxygen levels and an alkaline shift that occur following increased neuronal activity. Both chemical changes are transient and approximately simultaneous, occurring a few seconds after the electrical activity.

Oxygen and pH levels can be measured in the brain using fast-scan cyclic voltammetry. Extracellular oxygen levels can also be measured using optical recording of intrinsic signals (ORIS). ORIS relies on the differential absorption of oxygenated (Hb02) and deoxygenated hemoglobin (Hbr). At isobestic wavelengths (525, 545, 570.5 and 583 nm) Hb02 and Hbr reflect light equally and thus the resulting signal reflects total hemoglobin. Total hemoglobin is directly proportional to cerebral blood volume and cerebral blood flow giving a measure of tissue perfusion. At higher wavelengths (605-650 nm), the majority of the signal comes from Hbr since Hbr has a higher absorption coefficient than Hb02. Using ORIS may require using light emitting diodes to illuminate and an isolated photosensitive diode to detect the reflected light. Similar technology has been used to detect oxygen saturation in cardiac tissue. Alternative technologies for sensing oxygen include quench fluorescence and impedance plethsymography. Voltammetry can also be used to measure levels of specific neurotransmitters, such as dopamine, adenosine, serotonin, and norepinephrine or electrochemically active neuropeptides such as oxytocin and vasopressin. Other or additional neurotransmitters, including glutamate and GABA may be measured using methods including but not limited to fixed potential amperometry at enzyme-linked bio sensors.

If a particular neurological event type or types can be detected in or other feature of interest can be extracted from the monitored electrographic signals and then correlated to whether a given stimulation parameter subspace is effective in achieving a desired therapeutic result, then the neurostimulator 110 further can be configured to monitor a variable that reflects the correlation. For example, the number of detected events occurring in the signal(s) (ECoG(s)) acquired by the neurostimulator 110 over a particular period of time (e.g., 24 hours) may provide a measure of how effective the stimulation parameter subspace is for the particular patient. For example, if the rate (or count) of detected events exceeds a certain threshold, the recipient of this information, whether it be an external component of the neurostimulation system, the neurostimulator itself, or a physician viewing and interacting with data (e.g., using a database application (website) for an external component of the neurostimulation system), may infer or conclude that the stimulation parameter subspace or a stimulation parameter set should be adjusted in some respect in order to improve the therapeutic effect of stimulation. Such a change may include a change from a present stimulation parameter subspace (if there is one) to the stimulation parameter subspace as recommended by the mapping function.

The rate (or count) of detected events is just one example of a metric the neurostimulator 110 may be configured to track and/or store and/or record, in order to assess whether stimulation therapy delivered in accordance with the present stimulation parameter set (or within a present stimulation parameter set subspace) is effective for the patient. As noted above, other metrics of effectiveness may include duration of detected events, rate of detections over time, changes in power in specific frequency bands, pH shifts, tissue oxygenation, neurotransmitter levels, evoked potential "EP" amplitude, or clinical seizure rate (count of patient-identified events during a period of time).

In one embodiment, an overall effectiveness value for a given stimulation therapy, e.g., a given stimulation parameter set, within a given stimulation parameter subspace, may be calculated using a combination of the data and by multiplying the number of electrographic seizures detected per week by the neurostimulator 110 by the average duration of the electrographic seizures. This calculation yields a value that is descriptive of the total time per week spent in an electrographic seizure, and it will be apparent that relatively low values such as one minute per week may be associated with effectiveness of a given stimulation therapy whereas relatively high values such as 1000 minutes per week may be associated with lack of effectiveness of the stimulation therapy. The value yielded by this calculation may be compared against a criterion related to neurological events detected by the neurostimulator. In the case of detected neurological events corresponding to electrographic seizures, a criterion may be an accumulated duration of detected neurological events over a period of time, e.g., five total minutes per week of electrographic seizures. If the accumulated duration of detected neurological events within the specified time period exceeds the specified duration, the present stimulation parameter subspace may be determined to be ineffective. Conversely, if the accumulated duration of detected neurological events within the specified time period does not exceed the specified duration, the present stimulation parameter subspace may be determined to be effective.

It should be understood that a patient may experience different seizure onset type based on his or her sleep-wake cycle. For instance, a patient may have a hypersynchronous seizure onset during wakefulness and a low voltage fast (LVF) seizure onset during sleep, and both onsets may be sensed or detected on the same sensing channel. Overall, the patient may have more of the LVF seizure onset neurological events because the patient tends to have more seizures when sleeping. Thus, an integration module according to embodiments may also integrate a metric corresponding to the time of day of detected neurological events or the sleep-wake state of the patient.

It should also be understood that the anti-epileptic drug (AED) therapy a patient is receiving may be relevant to the determination of whether to make a change to a stimulation parameter subspace or to apply a default stimulation parameter set as recommended by the mapping function. Thus, identification of the current AED(s), information about past AEDs; changes to AED dosage (recent or historical) may also be beneficial inputs to the integration module. For instance, changing an AED from a sodium channel blocker to a γ-aminobutyric acid (GABA) A receptor positive modulator may influence the seizure onset type observed, so that the neurological event type classification on which the mapping function result is based may not be reliable. If metrics related to AEDs are included in the integration module, the integration module may be configured to prevent implementing a change to the stimulation parameter subspace or to the default stimulation parameter set recommended by the mapping function if the mapping function result is delivered less than a certain amount of time after a change to the patient's AED regimen, e.g., in the recent past or within the last 14 days.

The integration module function can be implemented in some embodiments: (1) in the neurostimulator, supplied with inputs originating internally or externally of the patient, or some combination of the two; (2) in one of the external components of the neurostimulation system, or (3) in both the neurostimulator and an external component of the neurostimulation system. The integration module function may be automatic, or based on input from a physician, or implemented with some combination of the two.

In embodiments in which input from a clinician is possible, the stimulation parameter subspace may be recommended by an external component directly to the clinician in a numerical or graphical display. The clinician may then use this information in combination with additional inputs from the external system, including but not limited to measures of effectiveness, the present stimulation parameter subspace, the stimulation parameter set history as well the time since the last stimulation parameter set change, in order to inform the decision to either adjust the neurostimulator to the stimulation parameter subspace or the default stimulation parameter set recommended by the mapping function. For instance, when a stimulation parameter subspace change is recommended by the mapping function, the clinician would look at the measures of effectiveness and determine if the patient had experienced a reduced rate of electrographic and/or clinical seizures since, for example, the last time the stimulation parameter subspace or a stimulation parameter set was adjusted. If the patient had not experienced a meaningful reduction in their seizure rate, the clinician may review the patient's stimulation parameter set history to determine if the patient had ever received stimulation therapy according to parameter values that fell within the stimulation parameter subspace recommended by the mapping function. If the patient's neurostimulator had never been programmed to deliver stimulation therapy within the recommended stimulation parameter subspace, the clinician may also consider when the last change to the stimulation parameter set was made. If the last change to the stimulation parameter set was, for instance, 28 days ago or longer, the clinician may decide to make the change to the stimulation parameter subspace recommended by the mapping function.

Optimization Module

The optimization module allows the neurostimulator to optimize the values of the parameters within a stimulation parameter subspace, to achieve the most effective stimulation parameter set and therefore the best therapeutic result for the patient.

Optimization may involve periodically checking the effectiveness of a present stimulation parameter set within a stimulation parameter subspace based on measures of effectiveness. If an effectiveness criterion is not satisfied, the optimization module can adjust the discrete value for one or more of the parameters within a stimulation parameter set to another value within the stimulation parameter subspace.

Figure 18:
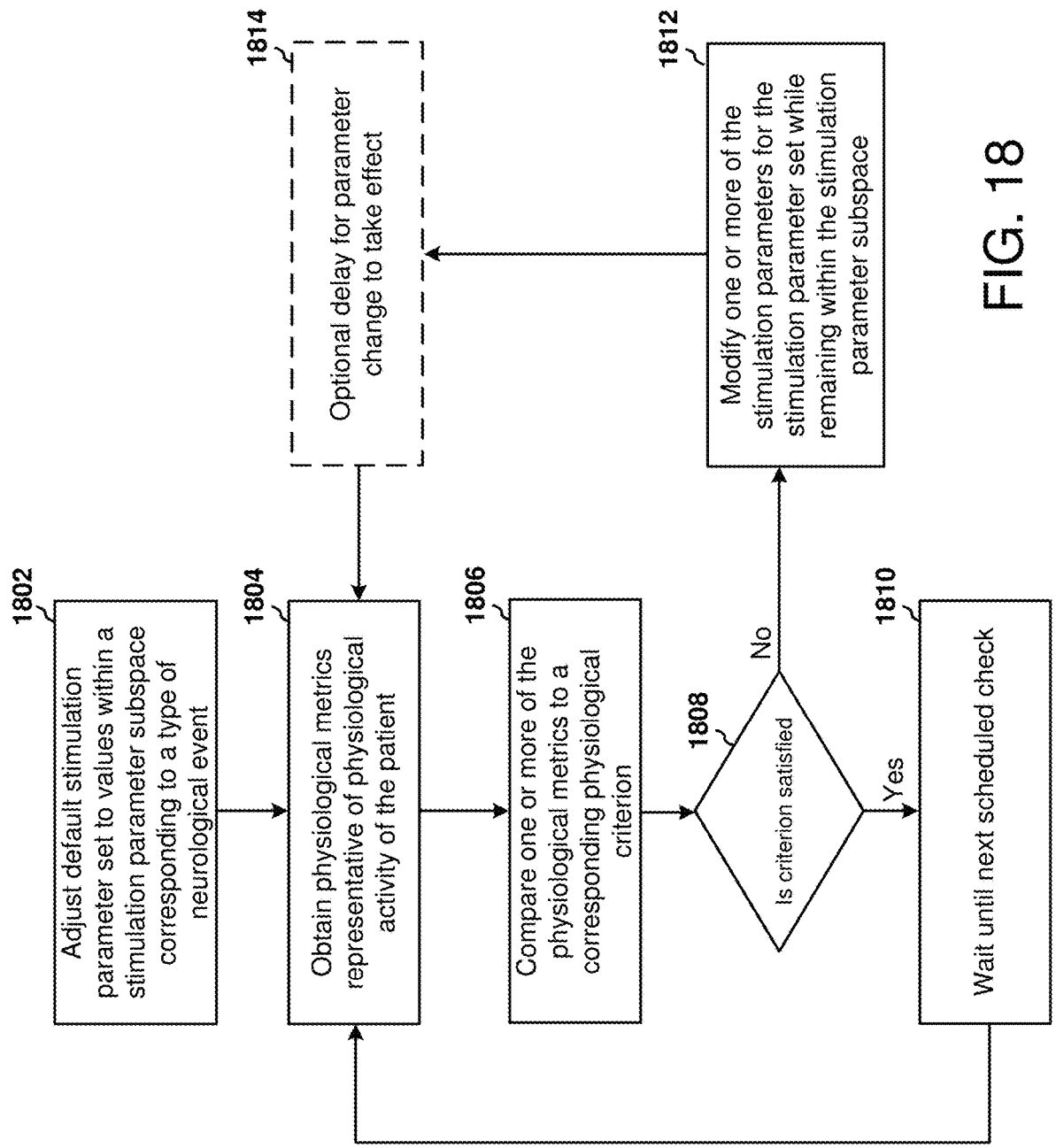
FIG. 18 is a flow chart of a method of optimizing stimulation parameters of a neurostimulator.

Referring now to FIG. 18, an embodiment implements an optimization module after a stimulation therapy is delivered in accordance with a default stimulation parameter set at 1802 in response to detection of a neurological event, for example, a neurological event classified as a type of seizure onset.

At 1804, the optimization module receives inputs corresponding to certain predetermined physiological activity of the patient and obtains (e.g., measures, stores, logs and records) physiological metrics representative of the physiological activity. The physiological activity may be one or more of electrophysiological activity and non-electrophysiological activity. The physiological metrics may include one or more of the metrics used to determine a measure of effectiveness of neurostimulation therapy as described above with reference to the integration module (FIG. 17). The inputs to the optimization module may originate from the neurostimulator itself, from other sensors located internally or externally of the patient, or otherwise from an external component of the neurostimulation system.

One or more of the physiological metrics is compared to a corresponding physiological criterion at 1806. The physiological criterion may be an electrophysiological criterion, such as a decrease in the duration of detected neurological events or a decrease in the rate of detected neurological events over a particular time as compared to a threshold, changes in ECoG power in specific frequency bands, and/or increases in entropy of the electrographic signal over time and above a threshold. For example, the effectiveness of a stimulation parameter set may be estimated to be inversely proportional to the count of detected events in 28 day periods. The physiological criterion would consist of a threshold below which the number of detected events for a single or multiple 28-day periods(s) would indicate that the therapy was effective and above which the number of detected events for a single or multiple 28-day period(s) would indicate a stimulation parameter change was warranted. The physiological criterion may also be a non-electrophysiological criterion, such as shifts in the pH of local brain tissue, changes in tissue oxygenation, neurotransmitter levels above or below a threshold, rate of clinical seizures in a patient above or below a threshold.

If the physiological criterion was satisfied at 1808, the stimulation parameters of the neurostimulator are unchanged at 1810, and the neurostimulator waits until a next scheduled check, at which time the process begins again at 1804.

If the physiological criterion was not satisfied at 1808, then the neurostimulator modifies either one or more of the discrete values of the stimulation parameters within the present stimulation parameter subspace creating a new stimulation parameter set for generation and delivery of an instance of stimulation at 1812. For example when the physiological criterion has not been met, a new combination of values for all of the stimulation parameters in a stimulation parameter set except for one may be chosen pseudo-randomly from within the stimulation parameter subspace, with the one exception being held constant. Which parameter is changed within the subspace may depend on the present stimulation parameter subspace. For example, with reference to Table 1, in the case of the high frequency stimulation parameter subspace for a low voltage fast seizure onset type, the pulse amplitude of the instance of stimulation may be held constant while combinations of different values for the other parameters are tested within the ranges for each parameter defined by the stimulation parameter subspace. In contrast, in the case of a theta stimulation parameter subspace, the value of the frequency parameter may be held constant while testing new combinations of values for the other parameters. The parameters are chosen pseudo-randomly since parameter value combinations that have already been used in a patient's stimulation parameter set history and did not produced the desired response will not be tried.

The optimization module may be configured with an optional delay, e.g., 28 days, at 1814. After the neurostimulator modifies one or more of the stimulation parameter values, a timer may be started for the specified delay. The delay allows time for the change to the value(s) to have a physiological effect or otherwise measurable therapeutic effect. After the delay, the neurostimulator resumes monitoring the physiological activity at 1804. Optimization may continue until either the physiological criterion has been satisfied or all possible combinations of values for the stimulation parameters (for example, all combinations of values possible for the relevant stimulation parameter subspace) have been tried.

The optimization module function can be implemented in some embodiments: (1) in the neurostimulator, supplied with inputs originating internally or externally of the patient, or some combination of the two; (2) in one of the external components of the neurostimulation system, or (3) in both the neurostimulator and an external component of the neurostimulation system. The optimization module function may be automatic, or based on input from a physician, or implemented with some combination of the two.

Offline Implementation of the Mapping Function, Integration and Optimization Modules An embodiment of a neurostimulation system comprising an integration module and an optimization module implemented in an external component will now be described with reference to the block diagram of FIG. 19. Details regarding the previous description of the mapping function module, the integration module, and the optimization module will not be repeated here in describing this embodiment. Rather the descriptions of the mapping function module, integration module, and optimization module are hereby incorporated by reference with respect to the description of this embodiment.

The external component 1902 may be a programmer 212 (see FIG. 2) used by a clinician to establish a communications link with the implanted neurostimulator 110. The external device 1902 includes a processing system 1926 that may be implemented with a bus architecture, represented generally by the bus 1904. The bus 1904 links together various modules, which may comprise circuits including one or more processors and/or other hardware, firmware, or software, represented by the configuration module 1906 configured to implement the mapping function module and the integration module, and an event detection module 1908 configured to implement step 1506, a feature extraction module 1910 configured to identify neurological event types in the electrographic activity sensed and analyzed by the neurostimulator 110, a probability/rank module 1912 configured to implement the mapping function (e.g., 1510 through 1518 of FIG. 15), and a subspace determination module 1914, configured to determine a stimulation parameter subspace and default stimulation parameter set for the neurological event type detected by the neurostimulator (1520 through 1526 of FIG. 15), a memory module 1916, an integration module 1922, an optimization module 1924, a processor 1918, and a computer-readable medium/memory 1920. The bus 1904 may also link various other circuits such as timing sources, peripherals, voltage regulators, and power management circuits, which are well known in the art, and therefore, will not be described any further here.

The configuration module 1906 is configured to implement 1502, 1504 and 1528 of FIG. 15, i.e., to configure a neurostimulator 110 to detect physiological activity (e.g., electrographic activity) and to record and store data associated with that activity; to download stored data from the neurostimulator; and to set, or recommend to set, the values of stimulation parameters to values within a top ranked stimulation parameter subspace as determined by the subspace determination module 1914. The configuration module 1916 is also configured to implement 1802, 1804 and 1812 of FIG. 18, i.e., to set default stimulation parameters to values within a stimulation parameter subspace corresponding to a type of neurological event; to obtain physiological metrics representative of physiological activity of the patient; and to modify one or more values of the stimulation parameters within the stimulation parameter subspace. To these ends, the configuration module 1906 may be configured to establish a wired or wireless communication link with the neurostimulator 110 through a communications module 1928 of the external component 1902. The memory module 1916 is configured to store the data obtained from the neurostimulator.

The event detection module 1908 is configured to implement 1506 of FIG. 15, i.e., to process the ECoG files stored in the memory module 1916 to identify those ECoG files containing a particular neurological event type, e.g., a type of seizure onset. The feature extraction module 1910 is also configured to implement 1508 of FIG. 15, i.e., to extract features from the ECoGs records identified by the event detection module 1908.

The probability/rank module 1912 is configured to implement 1510 and 1512 of FIG. 15, i.e., to group ECoG records based on channel, and to select a group of ECoG records for further processing. The probability/rank module 1912 is also configured to implement 1514, 1516 and 1518, i.e., to assign probabilities corresponding to seizure onset types, to each ECoG record in the selected group; to process the probabilities across all ECoG records in the selected group to obtain a set of probabilities for seizure onset types for the channel corresponding to the selected group; and to rank seizure onset types based on probabilities.

The subspace determination module 1914 is configured to implement 1520, 1522, 1524, and 1526 of FIG. 15, i.e., to determine stimulation parameter subspaces for one or more of the ranked seizure onset types; to compare present stimulation parameter sets for the channel to the top ranked determined stimulation parameter subspace for the channel; to maintain the present stimulation parameter set when the values for the present parameter set are within the top ranked stimulation parameter subspace; and to change, or recommend to change, the values for the stimulation parameters to values within the top ranked stimulation parameter subspace when the present stimulation parameter set is not within the top ranked stimulation parameter subspace. In this regard, the subspace determination module 1914 may command the configuration module 1906 to communicate with the neurostimulator to change either a stimulation parameter subspace or a stimulation parameter set. Alternatively, the subspace determination module 1914 may provide a recommended stimulation parameter set to the integration module 1922.

The integration module 1922 is configured to perform the integration function described in more detail above with reference to FIG. 17. To this end, the integration module 1922 may cause the configuration module 1906 to communicate with the neurostimulator to obtain any data corresponding to measures of effectiveness, the present stimulation=parameter subspace, the stimulation parameter subspace history or stimulation parameter set history, and the time since last change to either a stimulation parameter subspace or a stimulation parameter set. Based on this information, the integration module 1922 determines whether to implement the recommendation to change to the stimulation parameter subspace.

The optimization module 1924 is configured to implement 1806, 1808, and 1810 of FIG. 18, i.e., to compare one or more of the physiological metrics to a corresponding physiological criterion; to determine if the criterion is satisfied; to wait until a next schedule check if the criterion is satisfied; and to cause the configuration module 1906 to modify one or more values of the stimulation parameters within the stimulation parameter subspace when the criterion is not satisfied. The optimization module 1824 is also configured to implement 1814 of FIG. 18, i.e., an optional delay by the configuration module 1906 in modifying one or more values of the stimulation parameters within the stimulation parameter subspace.

The processor 1916 is responsible for general processing, including the execution of software stored on the computer-readable medium/memory 1918. The software, when executed by the processor 1916, causes the modules to perform the various functions described herein for any particular module. The configuration module 1906, event detection module 1908, feature extraction module 1910, a probability/rank module 1912, subspace determination module 1914, integration module 1922, and optimization module 1924, may be software modules running in the processor 1918, resident/stored in the computer readable medium/memory 1920, one or more hardware modules coupled to the processor 1918, or some combination thereof.

Online Implementation of the Mapping Function, Integration, and Optimization Modules FIG. 21 is a block diagram of a neurostimulator 2102 configured to implement the methods of FIGS. 17, 18 and 20 to thereby determine and adjust values for the stimulation parameter set for delivery of an instance of stimulation therapy. Details regarding the numerous steps in the method of FIGS. 17, 18 and 20 are not repeated below when describing the various modules of the neurostimulator 2102 that are configured to implement respective steps. The descriptions of the processes, configurations, and algorithms included above with respect to FIGS. 17, 18 and 20 are incorporated by reference to the descriptions of the modules that implement the respective steps identified in FIG. 21.

The neurostimulator 2102 includes a processor system 2124 that may be implemented with a bus architecture, represented generally by the bus 2104. The bus 2104 links together various circuits including one or more processors and/or hardware modules, represented by an ECoG sensing module 2106 configured to implement step 2002, a feature extraction module 2108 configured to implement steps 2004 and 2010, an event detection module 2110 configured to implement step 2006 and 2012, a mapping function module 2112 configured to implement step 2016, a stimulation module 2114 configured to implement step 2018, an integration module 2111, an optimization module 2117, a processor 2118, and a computer-readable medium/memory 2120. The bus 2104 may also link various other circuits such as timing sources, peripherals, voltage regulators, and power management circuits, which are well known in the art, and therefore, will not be described any further.

The ECoG sensing module 2106 is configured to implement 2002 of FIG. 20, i.e., to sense electrographic signals, e.g., ECoG. The feature extraction module 2108 is configured to implement 2004 and 2010 of FIG. 20, i.e., to extract features from the sensed ECoGs. The event detection module 2110 is configured to implement 2006 and 2012 of FIG. 20, i.e., to detect for a neurological event based on the set of extracted features. The ECoG sensing module 2106, feature extraction module 2108, and event detection module 2110 may correspond to one or more of the various components of the detection subsystem 326 described above with reference to FIG. 3 and FIG. 4.

The mapping function module 2112 is configured to implement 2016 of FIG. 20, i.e., to determine a stimulation parameter subspace and set corresponding to the type of the detected neurological event. To this end, the extracted features corresponding to the detected neurological event are applied to a mapping function module that identifies the type of neurological event and a set of stimulation parameters for use in treating the neurological condition associated with the detected event.

The stimulation module 2114 is configured to implement step 2018 of FIG. 20, i.e., to deliver electrical stimulation using the set of stimulation parameters. The stimulation module 2114 may correspond to one or more of the various components of the therapy subsystem described above with reference to FIG. 3 and FIG. 5.

The integration module 2111 is configured to implement steps 1702 and 1714 of FIG. 17, i.e. to integrate the measures of effectiveness with the stimulation parameter subspace and set from the mapping function module. Thus the integration module may prevent the stimulation module 2114 from delivering stimulation within a new stimulation parameter subspace determined by the mapping function module 2112 if the measures of effectiveness suggest that the present stimulation parameter set is effective. The online integration module will not take into account the stimulation parameter set history as described for the offline implementation above.

The optimization module 2117 is configured to implement steps 1802-1814 of FIG. 18, i.e. to optimize the discrete values of the stimulation parameter set within a stimulation parameter subspace recommended by the mapping function module 2112.

The processor 2116 is responsible for general processing, including the execution of software stored on the computer-readable medium/memory 2118. The software, when executed by the processor 2116, causes the modules to perform the various functions described herein for any particular module. The ECoG selection module 2106, event detection module 2108, feature extraction module 2110, mapping function module 2112, integration module 2111, integration module 2117, memory module 2114, and obtaining module 2116 may be software modules running in the processor 2118, resident/stored in the computer readable medium/memory 2120, one or more hardware modules coupled to the processor 2118, or some combination thereof.

In summary, and with reference to FIG. 20, embodiments described above relate to treating a neurological disorder or condition of a patient using an implanted neurostimulation system. An electrographic signal in the patient's brain is sensed 2002. A set of features are extracted from the electrographic signal 2004, 2010. A neurological event associated with the neurological disorder is detected based on the set of extracted features, along with a type of the neurological event 2012. A stimulation parameter set corresponding to the type of neurological event is determined 2016. The set of stimulation parameters define an electrical stimulation for treating the neurological condition. The electrical stimulation is delivered to the brain 2018.

It will be appreciated that the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A neurostimulation system comprising:
    at least one sensor and at least one stimulator configured to be implanted in or on a brain of a patient; and
    a neurostimulator coupled to the at least one sensor and at least one stimulator and comprising:
        a sensing module configured to sense electrical activity of the brain through the at least one sensor and to create a record of electrographic activity corresponding to the sensed electrical activity of the brain;
        a detection module;
        a feature extraction module configured to extract a set of features from the record of electrographic activity, wherein the detection module is configured to detect an electrographic seizure onset based on the set of features;
        a classification module configured to be applied to the set of features to identify a seizure onset type;
        a mapping function module configured to identify, based on the identified seizure onset type, a stimulation parameter subspace comprising a range of potential values for each of a plurality of stimulation parameters, and a discrete default value for each of the plurality of stimulation parameters;
        a control module configured to determine which value to set for one or more of the plurality of stimulation parameters of the identified stimulation parameter subspace; and
        a stimulation module configured to generate an instance of stimulation based on the determined values of the plurality of stimulation parameters, and to deliver the instance of stimulation through the at least one stimulator.

2. The neurostimulation system of claim 1, wherein the mapping function module comprises a lookup table stored in a memory in which each of a plurality of different seizure onset types is correlated to a different stimulation parameter subspace.

3. The neurostimulation system of claim 1, wherein the seizure onset type comprises one of: a low-voltage-fast seizure onset, a high-voltage-beta seizure onset, a hypersynchronous seizure onset, a spike-and-wave seizure onset, a multiple seizure onset, an attenuation seizure onset, and a seizure onset type identified by a clustering process.

4. The neurostimulation system of claim 1, wherein the stimulation parameter subspace comprises one of: a range of values comprising high frequencies for a frequency stimulation parameter, a range of values comprising very high frequencies for a frequency stimulation parameter, a theta burst stimulation parameter subspace, a voltage-controlled, low frequency stimulation parameter subspace, a high amplitude stimulation parameter subspace, and an alerting stimulation parameter subspace.

5. The neurostimulation system of claim 1, wherein the neurostimulator further comprises:
    an integration module configured to:
        analyze at least one data element other than a record of electrographic activity, which data element corresponds to one or more states of the patient in order to determine a measure of effectiveness of a course of stimulation therapy; and
        communicate the measure of effectiveness to the control module,
    wherein the control module is further configured to determine which value to set for each of the plurality of stimulation parameters based in part on the measure of effectiveness.

6. The neurostimulation system of claim 5, wherein the at least one data element other than a record of electrographic activity comprises one or both of an electrophysiological metric and a non-electrophysiological metric.

7. The neurostimulation system of claim 6, wherein the electrophysiological metric comprises one or more of: a detected event count, a detected event rate, a long episode rate, a detected event duration, a saturation rate, changes in power in specific frequency bands, and amplitude of evoked potentials.

8. The neurostimulation system of claim 6, wherein the non-electrophysiological metric comprises one or more of: oxygenation concentration, pH/alkaline shift, neurotransmitter levels.

9. The neurostimulation system of claim 5, wherein the neurostimulator further comprises:
    an optimization module configured to:
        receive the measure of effectiveness from the integration module;
        compare the measure of effectiveness to a criterion; and
        when the criterion has not been satisfied, send an instruction to the control module to set a new value for one or more of the plurality of stimulation parameters.

10. The system of claim 1, wherein the feature extraction module is further configured to:
    extract a first set of features from the record of electrographic activity, wherein the detection module is configured to detect an electrographic seizure based on the first set of features, and
    extract the set of features from the record of electrographic activity, responsive to a detection of an electrographic seizure based on the first set of features.

11. The system of claim 1, wherein the classification module comprises a machine-learned module trained on a dataset comprising sets of features extracted from records of electrographic activity.

12. A method of neurostimulation comprising:
sensing electrical activity of a brain through at least one sensor implanted in or on a brain of a patient;
creating a record of electrographic activity corresponding to the sensed electrical activity of the brain;
extracting a set of features from the record of electrographic activity;
detecting an electrographic seizure onset based on the set of features;
applying the set of features to a classification module to identify a seizure onset type;
identifying, based on the identified seizure onset type, a stimulation parameter subspace comprising a range of potential values for each of a plurality of stimulation parameters, and a discrete default value for each of the plurality of stimulation parameters;
determining which value to set for one or more of the plurality of stimulation parameters of the identified stimulation parameter subspace;
generating an instance of stimulation based on the determined values of the plurality of stimulation parameters; and
delivering the instance of stimulation through at least one stimulator implanted in or on a brain of a patient.

13. The method of claim 12, wherein each of a plurality of different seizure onset types is correlated to a different stimulation parameter subspace.

14. The method of claim 12, wherein the seizure onset type comprises one of: a low-voltage-fast seizure onset, a high-voltage-beta seizure onset, a hypersynchronous seizure onset, a spike-and-wave seizure onset, a multiple seizure onset, an attenuation seizure onset, and a seizure onset type identified by a clustering process.

15. The method of claim 12, wherein the stimulation parameter subspace comprises one of: a range of values comprising high frequencies for a frequency stimulation parameter, a range of values comprising very high frequencies for a frequency stimulation parameter, a theta burst stimulation parameter subspace, a voltage-controlled, low frequency stimulation parameter subspace, a high amplitude stimulation parameter subspace, and an alerting stimulation parameter subspace.

16. The method of claim 12, further comprising:
analyzing at least one data element other than a record of electrographic activity, which data element corresponds to one or more states of the patient in order to determine a measure of effectiveness of a course of stimulation therapy; and
wherein the determining is based in part on the measure of effectiveness.

17. The method of claim 16, wherein the at least one data element other than a record of electrographic activity comprises one or both of an electrophysiological metric and a non-electrophysiological metric.

18. The method of claim 17, wherein the electrophysiological metric comprises one or more of: a detected event count, a detected event rate, a long episode rate, a detected event duration, a saturation rate, changes in power in specific frequency bands, and amplitude of evoked potentials.

19. The method of claim 17, wherein the non-electrophysiological metric comprises one or more of: oxygenation concentration, pH/alkaline shift, neurotransmitter levels.

20. The method of claim 16, further comprising:
comparing the measure of effectiveness to a criterion; and
setting a new value for one or more of the plurality of stimulation parameters when the criterion has not been satisfied.

21. The method of claim 12, further comprising:
extracting a first set of features from the record of electrographic activity; and
detecting an electrographic seizure based on the first set of features,
wherein the extracting the set of features from the record of electrographic activity occurs in response to a detection of an electrographic seizure based on the first set of features.

* * * * *